US010251928B2

(12) United States Patent
van Tol et al.

(10) Patent No.: US 10,251,928 B2
(45) Date of Patent: *Apr. 9, 2019

(54) NUTRITIONAL SUPPLEMENTS CONTAINING A PEPTIDE COMPONENT AND USES THEREOF

(71) Applicant: Mead Johnson Nutrition Company, Glenview, IL (US)

(72) Inventors: Eric A. F. van Tol, Arnhem (NL); Marieke H. Schoemaker, Rhenen (NL); Gabriele Gross, Nijmegen (NL); Teartse Tim Lambers, Nijmegen (NL); Peter Wielinga, Delft (NL); Robert Kleemann, Delft (NL)

(73) Assignee: MEAD JOHNSON NUTRITION COMPANY, Evansville, IN (US)

( * ) Notice: Subject to any disclaimer, the term of this patent is extended or adjusted under 35 U.S.C. 154(b) by 668 days.

This patent is subject to a terminal disclaimer.

(21) Appl. No.: 14/535,241

(22) Filed: Nov. 6, 2014

(65) Prior Publication Data

US 2016/0129071 A1 May 12, 2016

(51) Int. Cl.
A61K 38/08 (2019.01)
A61K 31/202 (2006.01)
A61K 35/747 (2015.01)
A61K 38/06 (2006.01)
A23L 33/115 (2016.01)
A23L 33/12 (2016.01)
A23L 33/135 (2016.01)
A23L 33/18 (2016.01)
A61K 35/00 (2006.01)

(52) U.S. Cl.
CPC ............ A61K 38/08 (2013.01); A23L 33/115 (2016.08); A23L 33/12 (2016.08); A23L 33/135 (2016.08); A23L 33/18 (2016.08); A61K 31/202 (2013.01); A61K 35/747 (2013.01); A61K 38/06 (2013.01); A23V 2002/00 (2013.01); A23Y 2220/73 (2013.01); A61K 2035/115 (2013.01)

(58) Field of Classification Search
CPC .................................................. A61K 35/747
See application file for complete search history.

(56) References Cited

U.S. PATENT DOCUMENTS

| 6,495,344 B1 * | 12/2002 | Carr .................. C07K 14/4732 435/252.3 |
| 2002/0150679 A1 | 10/2002 | Bell |
| 2004/0132819 A1 | 7/2004 | Auestad et al. |
| 2007/0026049 A1 | 2/2007 | Auestad et al. |
| 2007/0203237 A1 | 8/2007 | Brenna et al. |
| 2007/0203238 A1 | 8/2007 | Jouni et al. |
| 2014/0271553 A1 | 9/2014 | Hondmann et al. |
| 2014/0271586 A1 | 9/2014 | Hondmann et al. |
| 2014/0274892 A1 | 9/2014 | Hondman et al. |

FOREIGN PATENT DOCUMENTS

| EP | 1599215 | 8/2010 |
| EP | 1898724 | 8/2010 |
| EP | 2353595 | 10/2011 |
| EP | 2420244 | 2/2012 |
| WO | 2004012727 | 2/2004 |
| WO | 2007100566 | 9/2004 |
| WO | 2007004878 | 1/2007 |
| WO | 2007073192 | 6/2007 |
| WO | 2007100561 | 9/2007 |
| WO | 2007116091 | 10/2007 |
| WO | 2008054208 | 5/2008 |

OTHER PUBLICATIONS

Scalabrin et al. Clinical Pediatrics, 2009, 48(7):734-744.*
Flachs, P., et al., "Synergistic induction of lipid catabolism and anti-inflammatory lipids in white fat of dietary obese mice in response to calorie restriction and n-3 fatty acids," Diabetologia, DOI 10.1007/s00125-011-2233-2 published online Jul. 21, 2011.
Geerts, B., et al., "Hydrolyzed Casein Decreases Postprandial Glucose Concentrations in T2DM Patients Irrespective of Leucine Content," Journal of Dietary Supplements, 8(3):280-292, 2011.
Goto, T., et al., "Soluble soy protein peptic hydrolysate stimulates adipocyte differentiation in 3T3-L1 cells," Mol. Nutr. Food Res. 2013,00, 1-11.
Gray, B., et al., "Omega-3 fatty acids: a review of the effects on adiponectin and leptin and potential implications for obesity management," European Journal of Clinical Nutrition (2013) 67, 1234-1242.
Holmer-Jensen, J., et al., "Acute differential effects of milk-derived dietary proteins on postprandial lipaemia in obese non-diabetic subjects," European Journal of Clinical Nutrition (2012) 66, 32-38.
Jonker, J.T., et al., "Effects of low doses of casein hydrolysate on post-challenge glucose and insulin levels," European Journal of Internal Medicine 22 (2011) 245-248.
Jung, E., et al., "Effects of Yeast Hydrolysate on Hepatic Lipid Metabolism in High-Fat-Diet-Induced Obese Mice: Yeast Hydrolysate Suppresses Body Fat Accumulation by Attenuating Fatty Acid Synthesis," Ann Nutr Metab 2012;61:89-94.

(Continued)

Primary Examiner — Bin Shen
(74) Attorney, Agent, or Firm — Troutman Sanders LLP; Ryan Schneider; Chris Davis

(57) ABSTRACT

The present disclosure relates to nutritional supplement including a peptide component. The nutritional supplement further includes a source of long-chain polyunsaturated fatty acids and *Lactobacillus rhamnosus* GG. The disclosure further relates to methods of protecting against obesity and its related metabolic disorders and inflammatory diseases in a target subject by providing the nutritional supplement(s) disclosed herein to a target subject, which includes a pediatric subject.

10 Claims, 38 Drawing Sheets
Specification includes a Sequence Listing.

(56) References Cited

OTHER PUBLICATIONS

Kalupahana, N., et al., "(n-3) Fatty Acids Alleviate Adipose Tissue Inflammation and Insulin Resistance: Mechanistic Insights1,2," Adv. Nutr. 2: 304-316, 2011.

Lefils, J., et al., Dietary DHA: time course of tissue uptake and effects on cytokine secretion in mice, British Journal of Nutrition (2010), 104, 1304-1312.

Liaset, B., et al., "Fish protein hydrolysate elevates plasma bile acids and reduces visceral adipose tissue mass in rats," Biochimica et Biophysica Acta 1791 (2009) 254-262.

Liaset, B., et al., "Nutritional Regulation of Bile Acid Metabolism Is Associated with Improved Pathological Characteristics of the Metabolic Syndrom," The Journal of Biological Chemistry vol. 286, No. 32, pp. 28382-28395, Aug. 12, 2011.

Lillefosse, H., et al., "Hydrolyzed Casein Reduces Diet-Induced Obesity in Male C57BL/6J Mice1-3," J. Nutr. doi: 10.3945/jn.112.170415.

Manders, R., et al., "Protein hydrolysate co-ingestion does not modulate 24h glycemic control in long-standing type 2 diabetes patients," European Journal of Clinical Nutrition (2009) 63, 121-126.

Martinez-Villaluenga, C., et al., "B-Conglycinin Embeds Active Peptides That Inhibit Lipid Accumulation in 3T3-L1 Adipocytes in Vitro," J. Agric. Food Chem. 2008, 56, 10533-10543.

Nongonierma, A., et al., "Dipeptidyl peptidase IV inhibitory and antioxidative properties of milk protein-derived dipeptides and hydrolysates," Peptides 39 (2013) 157-163.

Oosting, A., et al., "N-3 Long-Chain Polyunsaturated Fatty Acids Prevent Excessive Fat Deposition in Adulthood in a Mouse Model of Postnatal Nutritional Programming," Pediatric Research, Accepted Manuscript, Jul. 17, 2010.

Oster, R., et al., "Docosahexaenoic acid increases cellular adiponectin mRNA and secreted adiponectin protein, as well as PPARg mRNA, in 3T3-L1 adipocytes," Appl. Physiol. Nutr. Metab. 35: 783-789 (2010).

Rzehak, P., et al., "Short- and long-term effects of feeding hydrolyzed protein infant formulas on growth at greater than or equal to 6 y of age: results from the German Infant Nutritional Intervention Study1-3," Am J Clin Nutr 2009;89:1846-56.

Sipola, M., et al., "Effect of long-term intake of milk products on blood pressure in hypertensive rats," Journal of Dairy Research (2002) 69 103-111.

Vaughn, N, et al, "Intracerebroventricular Administration of Soy Protein Hydrolysates Reduces Body Weight without Affecting Food Intake in Rats," Plant Food Hum Nutr (2008) 63:41-46.

Ventura, A., et al., "Infant regulation of intake: the effect of free glutamate content in infant formulas1-4," Am J Clin Nutr 2012;95:875-81.

Xu, S., et al., "Ameliorating effects of casein glycomacropeptide on obesity induced by high-fat diet in mal Sprague-Dawley rats," Food and Chemical Toxicology 56 (2013) 1-7.

Yang, H., et al., "Soy protein retards the progression of non-alcoholic steatohepatitis via improvement of insulin resistance and steatosis," Nutrition 27 (2011) 943-948.

\* cited by examiner

FIG. 3A, 3B, 3C, and 3D
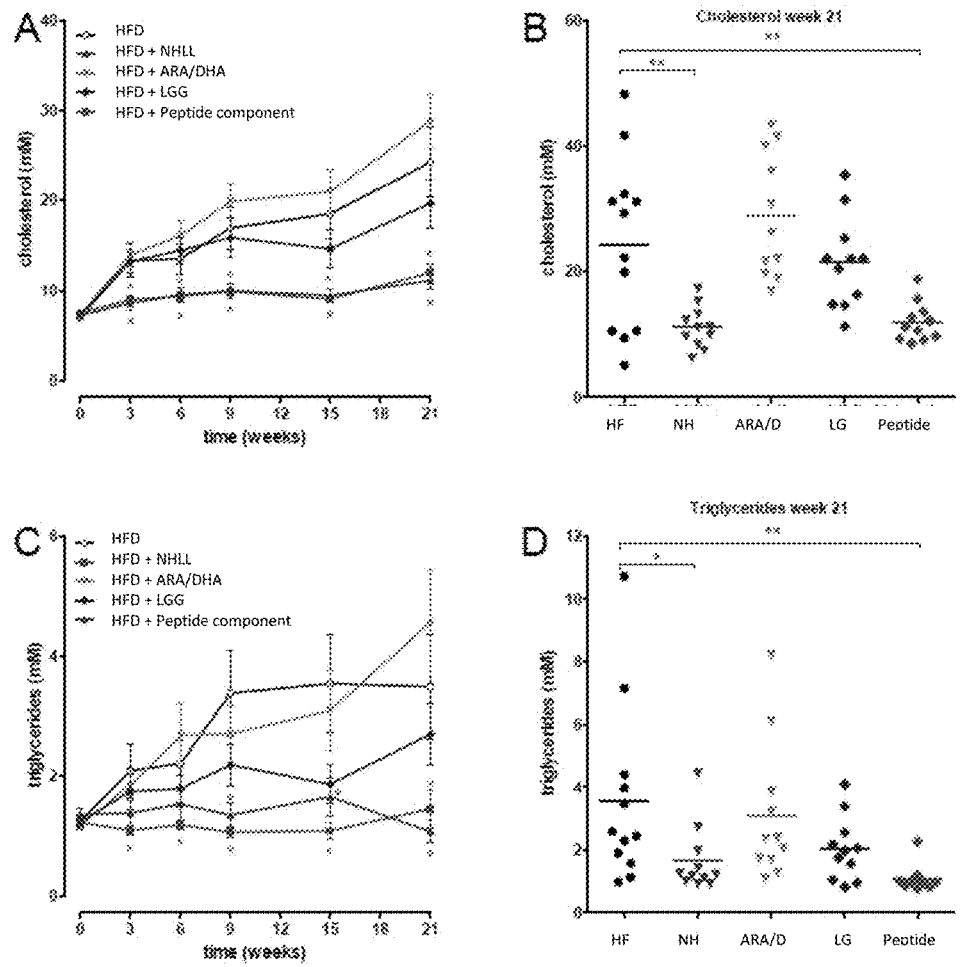

SEQUENCE LISTING

<160> NUMBER OF SEQ ID NOS: 64

<210> SEQ ID NO 1
<211> LENGTH: 8
<212> TYPE: PRT
<213> ORGANISM: Bovine

<400> SEQUENCE: 1

Ala Ile Asn Pro Ser Lys Glu Asn

```
1               5

<210> SEQ ID NO 2
<211> LENGTH: 5
<212> TYPE: PRT
<213> ORGANISM: BOVINE

<400> SEQUENCE: 2

Ala Pro Phe Pro Glu
1               5

<210> SEQ ID NO 3
<211> LENGTH: 6
<212> TYPE: PRT
<213> ORGANISM: BOVINE

<400> SEQUENCE: 3

Asp Ile Gly Ser Glu Ser
1               5

<210> SEQ ID NO 4
<211> LENGTH: 7
<212> TYPE: PRT
<213> ORGANISM: BOVINE

<400> SEQUENCE: 4

Asp Lys Thr Glu Ile Pro Thr
1               5

<210> SEQ ID NO 5
<211> LENGTH: 5
<212> TYPE: PRT
<213> ORGANISM: BOVINE

<400> SEQUENCE: 5

Asp Met Glu Ser Thr
1               5

<210> SEQ ID NO 6
<211> LENGTH: 4
<212> TYPE: PRT
<213> ORGANISM: BOVINE

<400> SEQUENCE: 6

Asp Met Pro Ile
1

<210> SEQ ID NO 7
<211> LENGTH: 4
<212> TYPE: PRT
<213> ORGANISM: BOVINE

<400> SEQUENCE: 7

Asp Val Pro Ser
1

<210> SEQ ID NO 8
<211> LENGTH: 7
<212> TYPE: PRT
<213> ORGANISM: BOVINE

<400> SEQUENCE: 8

Glu Thr Ala Pro Val Pro Leu
1               5
```

```
<210> SEQ ID NO 9
<211> LENGTH: 6
<212> TYPE: PRT
<213> ORGANISM: BOVINE

<400> SEQUENCE: 9

Phe Pro Gly Pro Ile Pro
1               5

<210> SEQ ID NO 10
<211> LENGTH: 7
<212> TYPE: PRT
<213> ORGANISM: BOVINE

<400> SEQUENCE: 10

Phe Pro Gly Pro Ile Pro Asn
1               5

<210> SEQ ID NO 11
<211> LENGTH: 4
<212> TYPE: PRT
<213> ORGANISM: BOVINE

<400> SEQUENCE: 11

Gly Pro Phe Pro
1

<210> SEQ ID NO 12
<211> LENGTH: 4
<212> TYPE: PRT
<213> ORGANISM: BOVINE

<400> SEQUENCE: 12

Gly Pro Ile Val
1

<210> SEQ ID NO 13
<211> LENGTH: 9
<212> TYPE: PRT
<213> ORGANISM: BOVINE

<400> SEQUENCE: 13

Ile Gly Ser Glu Ser Thr Glu Asp Gln
1               5

<210> SEQ ID NO 14
<211> LENGTH: 8
<212> TYPE: PRT
<213> ORGANISM: BOVINE

<400> SEQUENCE: 14

Ile Gly Ser Ser Ser Glu Glu Ser
1               5

<210> SEQ ID NO 15
<211> LENGTH: 9
<212> TYPE: PRT
<213> ORGANISM: BOVINE

<400> SEQUENCE: 15

Ile Gly Ser Ser Ser Glu Glu Ser Ala
1               5

<210> SEQ ID NO 16
```

```
<211> LENGTH: 6
<212> TYPE: PRT
<213> ORGANISM: BOVINE

<400> SEQUENCE: 16

Ile Asn Pro Ser Lys Glu
1               5

<210> SEQ ID NO 17
<211> LENGTH: 5
<212> TYPE: PRT
<213> ORGANISM: BOVINE

<400> SEQUENCE: 17

Ile Pro Asn Pro Ile
1               5

<210> SEQ ID NO 18
<211> LENGTH: 6
<212> TYPE: PRT
<213> ORGANISM: BOVINE

<400> SEQUENCE: 18

Ile Pro Asn Pro Ile Gly
1               5

<210> SEQ ID NO 19
<211> LENGTH: 9
<212> TYPE: PRT
<213> ORGANISM: BOVINE

<400> SEQUENCE: 19

Ile Pro Pro Leu Thr Gln Thr Pro Val
1               5

<210> SEQ ID NO 20
<211> LENGTH: 4
<212> TYPE: PRT
<213> ORGANISM: BOVINE

<400> SEQUENCE: 20

Ile Thr Ala Pro
1

<210> SEQ ID NO 21
<211> LENGTH: 4
<212> TYPE: PRT
<213> ORGANISM: BOVINE

<400> SEQUENCE: 21

Ile Val Pro Asn
1

<210> SEQ ID NO 22
<211> LENGTH: 7
<212> TYPE: PRT
<213> ORGANISM: BOVINE

<400> SEQUENCE: 22

Lys His Gln Gly Leu Pro Gln
1               5

<210> SEQ ID NO 23
<211> LENGTH: 5
<212> TYPE: PRT
```

<213> ORGANISM: BOVINE

<400> SEQUENCE: 23

Leu Asp Val Thr Pro
1               5

<210> SEQ ID NO 24
<211> LENGTH: 6
<212> TYPE: PRT
<213> ORGANISM: BOVINE

<400> SEQUENCE: 24

Leu Glu Asp Ser Pro Glu
1               5

<210> SEQ ID NO 25
<211> LENGTH: 5
<212> TYPE: PRT
<213> ORGANISM: BOVINE

<400> SEQUENCE: 25

Leu Pro Leu Pro Leu
1               5

<210> SEQ ID NO 26
<211> LENGTH: 6
<212> TYPE: PRT
<213> ORGANISM: BOVINE

<400> SEQUENCE: 26

Met Glu Ser Thr Glu Val
1               5

<210> SEQ ID NO 27
<211> LENGTH: 11
<212> TYPE: PRT
<213> ORGANISM: BOVINE

<400> SEQUENCE: 27

Met His Gln Pro His Gln Pro Leu Pro Pro Thr
1               5                   10

<210> SEQ ID NO 28
<211> LENGTH: 5
<212> TYPE: PRT
<213> ORGANISM: BOVINE

<400> SEQUENCE: 28

Asn Ala Val Pro Ile
1               5

<210> SEQ ID NO 29
<211> LENGTH: 5
<212> TYPE: PRT
<213> ORGANISM: BOVINE

<400> SEQUENCE: 29

Asn Glu Val Glu Ala
1               5

<210> SEQ ID NO 30
<211> LENGTH: 6
<212> TYPE: PRT
<213> ORGANISM: BOVINE

<400> SEQUENCE: 30

Asn Gln Glu Gln Pro Ile
1               5

<210> SEQ ID NO 31
<211> LENGTH: 5
<212> TYPE: PRT
<213> ORGANISM: BOVINE

<400> SEQUENCE: 31

Asn Val Pro Gly Glu
1               5

<210> SEQ ID NO 32
<211> LENGTH: 6
<212> TYPE: PRT
<213> ORGANISM: BOVINE

<400> SEQUENCE: 32

Pro Phe Pro Gly Pro Ile
1               5

<210> SEQ ID NO 33
<211> LENGTH: 6
<212> TYPE: PRT
<213> ORGANISM: BOVINE

<400> SEQUENCE: 33

Pro Gly Pro Ile Pro Asn
1               5

<210> SEQ ID NO 34
<211> LENGTH: 8
<212> TYPE: PRT
<213> ORGANISM: BOVINE

<400> SEQUENCE: 34

Pro His Gln Pro Leu Pro Pro Thr
1               5

<210> SEQ ID NO 35
<211> LENGTH: 5
<212> TYPE: PRT
<213> ORGANISM: BOVINE

<400> SEQUENCE: 35

Pro Ile Thr Pro Thr
1               5

<210> SEQ ID NO 36
<211> LENGTH: 4
<212> TYPE: PRT
<213> ORGANISM: BOVINE

<400> SEQUENCE: 36

Pro Asn Pro Ile
1

<210> SEQ ID NO 37
<211> LENGTH: 6
<212> TYPE: PRT
<213> ORGANISM: BOVINE

<400> SEQUENCE: 37

Pro Asn Ser Leu Pro Gln
1               5

<210> SEQ ID NO 38
<211> LENGTH: 8
<212> TYPE: PRT
<213> ORGANISM: BOVINE

<400> SEQUENCE: 38

Pro Gln Leu Glu Ile Val Pro Asn
1               5

<210> SEQ ID NO 39
<211> LENGTH: 7
<212> TYPE: PRT
<213> ORGANISM: BOVINE

<400> SEQUENCE: 39

Pro Gln Asn Ile Pro Pro Leu
1               5

<210> SEQ ID NO 40
<211> LENGTH: 6
<212> TYPE: PRT
<213> ORGANISM: BOVINE

<400> SEQUENCE: 40

Pro Val Leu Gly Pro Val
1               5

<210> SEQ ID NO 41
<211> LENGTH: 4
<212> TYPE: PRT
<213> ORGANISM: BOVINE

<400> SEQUENCE: 41

Pro Val Pro Gln
1

<210> SEQ ID NO 42
<211> LENGTH: 5
<212> TYPE: PRT
<213> ORGANISM: BOVINE

<400> SEQUENCE: 42

Pro Val Val Val Pro
1               5

<210> SEQ ID NO 43
<211> LENGTH: 6
<212> TYPE: PRT
<213> ORGANISM: BOVINE

<400> SEQUENCE: 43

Pro Val Val Val Pro Pro
1               5

<210> SEQ ID NO 44
<211> LENGTH: 11
<212> TYPE: PRT
<213> ORGANISM: BOVINE

<400> SEQUENCE: 44

Ser Ile Gly Ser Ser Ser Glu Glu Ser Ala Glu
1               5                   10

```
<210> SEQ ID NO 45
<211> LENGTH: 7
<212> TYPE: PRT
<213> ORGANISM: BOVINE

<400> SEQUENCE: 45

Ser Ile Ser Ser Ser Glu Glu
1               5

<210> SEQ ID NO 46
<211> LENGTH: 11
<212> TYPE: PRT
<213> ORGANISM: BOVINE

<400> SEQUENCE: 46

Ser Ile Ser Ser Ser Glu Glu Ile Val Pro Asn
1               5                   10

<210> SEQ ID NO 47
<211> LENGTH: 7
<212> TYPE: PRT
<213> ORGANISM: BOVINE

<400> SEQUENCE: 47

Ser Lys Asp Ile Gly Ser Glu
1               5

<210> SEQ ID NO 48
<211> LENGTH: 6
<212> TYPE: PRT
<213> ORGANISM: BOVINE

<400> SEQUENCE: 48

Ser Pro Pro Glu Ile Asn
1               5

<210> SEQ ID NO 49
<211> LENGTH: 7
<212> TYPE: PRT
<213> ORGANISM: BOVINE

<400> SEQUENCE: 49

Ser Pro Pro Glu Ile Asn Thr
1               5

<210> SEQ ID NO 50
<211> LENGTH: 7
<212> TYPE: PRT
<213> ORGANISM: BOVINE

<400> SEQUENCE: 50

Thr Asp Ala Pro Ser Phe Ser
1               5

<210> SEQ ID NO 51
<211> LENGTH: 5
<212> TYPE: PRT
<213> ORGANISM: BOVINE

<400> SEQUENCE: 51

Thr Glu Asp Glu Leu
1               5
```

<210> SEQ ID NO 52
<211> LENGTH: 6
<212> TYPE: PRT
<213> ORGANISM: BOVINE

<400> SEQUENCE: 52

Val Ala Thr Glu Glu Val
1               5

<210> SEQ ID NO 53
<211> LENGTH: 5
<212> TYPE: PRT
<213> ORGANISM: BOVINE

<400> SEQUENCE: 53

Val Leu Pro Val Pro
1               5

<210> SEQ ID NO 54
<211> LENGTH: 4
<212> TYPE: PRT
<213> ORGANISM: BOVINE

<400> SEQUENCE: 54

Val Pro Gly Glu
1

<210> SEQ ID NO 55
<211> LENGTH: 6
<212> TYPE: PRT
<213> ORGANISM: BOVINE

<400> SEQUENCE: 55

Val Pro Gly Glu Ile Val
1               5

<210> SEQ ID NO 56
<211> LENGTH: 6
<212> TYPE: PRT
<213> ORGANISM: BOVINE

<400> SEQUENCE: 56

Val Pro Ile Thr Pro Thr
1               5

<210> SEQ ID NO 57
<211> LENGTH: 4
<212> TYPE: PRT
<213> ORGANISM: BOVINE

<400> SEQUENCE: 57

Val Pro Ser Glu
1

<210> SEQ ID NO 58
<211> LENGTH: 9
<212> TYPE: PRT
<213> ORGANISM: BOVINE

<400> SEQUENCE: 58

Val Val Pro Pro Phe Leu Gln Pro Glu
1               5

<210> SEQ ID NO 59
<211> LENGTH: 5

```
<212> TYPE: PRT
<213> ORGANISM: BOVINE

<400> SEQUENCE: 59

Val Val Val Pro Pro
1               5

<210> SEQ ID NO 60
<211> LENGTH: 6
<212> TYPE: PRT
<213> ORGANISM: BOVINE

<400> SEQUENCE: 60

Tyr Pro Phe Pro Gly Pro
1               5

<210> SEQ ID NO 61
<211> LENGTH: 8
<212> TYPE: PRT
<213> ORGANISM: BOVINE

<400> SEQUENCE: 61

Tyr Pro Phe Pro Gly Pro Ile Pro
1               5

<210> SEQ ID NO 62
<211> LENGTH: 9
<212> TYPE: PRT
<213> ORGANISM: BOVINE

<400> SEQUENCE: 62

Tyr Pro Phe Pro Gly Pro Ile Pro Asn
1               5

<210> SEQ ID NO 63
<211> LENGTH: 5
<212> TYPE: PRT
<213> ORGANISM: BOVINE

<400> SEQUENCE: 63

Tyr Pro Ser Gly Ala
1               5

<210> SEQ ID NO 64
<211> LENGTH: 5
<212> TYPE: PRT
<213> ORGANISM: BOVINE

<400> SEQUENCE: 64

Tyr Pro Val Glu Pro
1               5
```

NUTRITIONAL SUPPLEMENTS CONTAINING A PEPTIDE COMPONENT AND USES THEREOF

RELATED APPLICATION

The present application is a continuation-in-part of co-pending and commonly assigned U.S. patent application Ser. No. 13/832,958 entitled "Nutritional Compositions Containing a Peptide Component with Adiponectin Stimulating Properties and Uses Thereof", filed Mar. 15, 2013; a continuation-in-part of co-pending commonly assigned U.S. patent application Ser. No. 13/839,488 entitled "Activating Adiponectin by Casein Hydrolysate", filed Mar. 15, 2013; a continuation-in-part of co-pending and commonly assigned U.S. patent application Ser. No. 13/832,958 entitled "Nutritional Compositions Containing a Peptide Component and Uses Thereof", filed Mar. 15, 2013; and a continuation-in-part of co-pending and commonly assigned U.S. Patent Application Serial No. "Reducing the Risk of Autoimmune Disease", filed Mar. 15, 2013, the disclosures of each are incorporated herein by reference in their entirety.

TECHNICAL FIELD

The present disclosure relates to nutritional supplements that include a peptide component, a source of long chain polyunsaturated fatty acid ("LCPUFA"), including docosahexaenoic acid ("DHA") and arachidonic acid ("ARA"), and *Lactobacillus rhamnosus* GG ("LGG") for preventing or protecting against the development of obesity, type 2 diabetes, cardiovascular disease, hepatosteatosis, impaired cognition, and/or kidney function.

In some embodiments, the nutritional supplement disclosed herein may reduce the main risk factors for metabolic syndrome including reduction in body fat mass, cholesterol, insulin resistance, and vascular and chronic inflammation. The nutritional supplement(s) described herein is suitable for administration to adult and pediatric subjects.

Additionally, the present disclosure provides methods for reducing the main risk factors for metabolic syndrome comprising providing the nutritional supplement including a peptide component, LCPUFA, and LGG to a target subject. Further disclosed herein are methods for protecting against obesity and its related disorders by providing the nutritional supplement including the peptide component, LCPUFA, and LGG described herein to a target subject.

BACKGROUND

Obesity is the hallmark of metabolic syndrome and represents a major global health problem that frequently associates with the development of chronic diseases, including type 2 diabetes. Childhood obesity has increased substantially in the past two decades and complications of metabolic syndrome, cardiovascular, muscle/skeletal and endocrine complications can start in early childhood. Also there are increasing incidence rates of non-alcoholic fatty liver disease and cognitive impairment in children. It is thought that increased low-grade/chronic inflammation is a driving force for disease development.

Thus, it would be useful to provide nutritional supplements or medical foods that are able to protect against obesity, metabolic disorders and associated chronic inflammatory diseases in a subject. In particular, it may be useful to protect against obesity and associated metabolic disorders in early life in order to reduce or prevent adult metabolic diseases.

Accordingly, the present disclosure provides a nutritional supplement including a peptide component comprising selected individual peptides as described herein. In some embodiments, the peptide component comprises the following peptides: SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63. In some embodiments, the peptide component comprises at least 10 additional peptides selected from Table 1.

In some embodiments the peptide component may include a peptide component that comprises at least 5 peptides selected from Table 1 and at least 3 additional peptides selected from Table 2. In still other embodiments, the peptide component may comprise at least 10 additional peptides selected from Table 1.

Without being bound by any particular theory, it is believed that the combination of the peptide component, a source of LCPUFA, and LGG as described herein may have favorable effects on adiponectin levels, body weight, fat deposits, kidney and liver function, plasma levels of risk factors associated with metabolic syndrome, adipocyte function, and cognition when consumed by individuals. Moreover, the present disclosure includes methods for protecting against obesity, cardiovascular disease, and other metabolic disorders and complications by providing a nutritional supplement including the peptide component, a source of LCPUFA, and LGG as disclosed herein.

BRIEF SUMMARY

Briefly, the present disclosure is directed, in an embodiment, to a nutritional supplement comprising a peptide component including the following peptides: SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63. In some embodiments, the peptide component may comprise at least 10 additional peptides selected from Table 1.

In some embodiments the peptide component may comprise at least 5 peptides selected from Table 1 and at least 3 peptides selected from Table 2. In still other embodiments, the peptide component may comprise at least 10 additional peptides selected from Table 1.

In some embodiments the nutritional supplement includes a peptide component wherein 5% to 100% of the peptide component comprises selected peptides from Tables 1 and/or Table 2 and 5% to 100% of the peptide component comprises peptides present in a hydrolyzed protein source such as extensively hydrolyzed protein, partially hydrolyzed protein, and combinations thereof.

The nutritional supplement(s) of the present disclosure may further comprise a source of LCPUFA, LGG, and combinations thereof. In some embodiments, the nutritional supplement may be provided in or with a pediatric nutritional composition, infant formula, nutritional additive or adult nutritional composition.

In some embodiments the disclosure is directed to a method for protecting against obesity by providing the nutritional supplement including the peptide component, a source of LCPUFA, and LGG as disclosed herein. Further the disclosure provides method(s) for reducing body weight, total body fat mass, and/or subcutaneous fat mass in a target subject, the method includes providing a nutritional supplement including a peptide component, a source of LCPUFA, and LGG as disclosed herein.

In some embodiments the present disclosure provides methods for promoting proper kidney and/or liver function, the method includes providing a nutritional supplement including a peptide component, a source of LCPUFA, and LGG as disclosed herein.

In some embodiments the present disclosure provides methods for reducing the plasma levels of risk factors of metabolic syndrome, the method includes providing a nutritional supplement including a peptide component, a source of LCPUFA, and LGG as disclosed herein. In some embodiments, providing the nutritional supplement disclose herein strongly reduces cholesterol and plasma triglycerides levels, fasting insulin levels, systemic and vascular inflammation, C-Peptide levels, GIP levels, and Leptin levels.

In some embodiments the present disclosure provides methods for inducing white adipogenesis and/or promoting the formation of functional fat by providing a nutritional supplement including a peptide component, a source of LCPUFA, and LGG as disclosed herein.

In some embodiments, the present disclosure is directed to dietary management of reducing and or preventing metabolic disturbances and reducing metabolic disease risk factor reduction in a target subject by providing the nutritional supplement disclosed herein.

Still, in some embodiments the present disclosure provides methods for protecting against cognitive degeneration, brain inflammation, and/or preventing impaired cognition by providing a nutritional supplement including a peptide component, a source of LCPUFA, and LGG as disclosed herein.

Without being bound by any particular theory, the combination of the peptide component, LCPUFA, and LGG, as described herein may provide synergistic and/or additive health benefits not observed by the individual administration of each compound. For example, the combination of the peptide component, LCPUFA, and LGG may provide synergistic effects regarding obesity and metabolic risk factors. The disclosed nutritional supplements may provide additive and or/synergistic beneficial health effects.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

BRIEF DESCRIPTION OF THE DRAWINGS

FIG. 3A illustrates fasting plasma cholesterol over 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.

FIG. 3B illustrates fasting plasma cholesterol after 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.

FIG. 3C illustrates fasting plasma triglycerides over 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.

FIG. 3D illustrates fasting plasma triglycerides after 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.

DETAILED DESCRIPTION

Figure 1A:
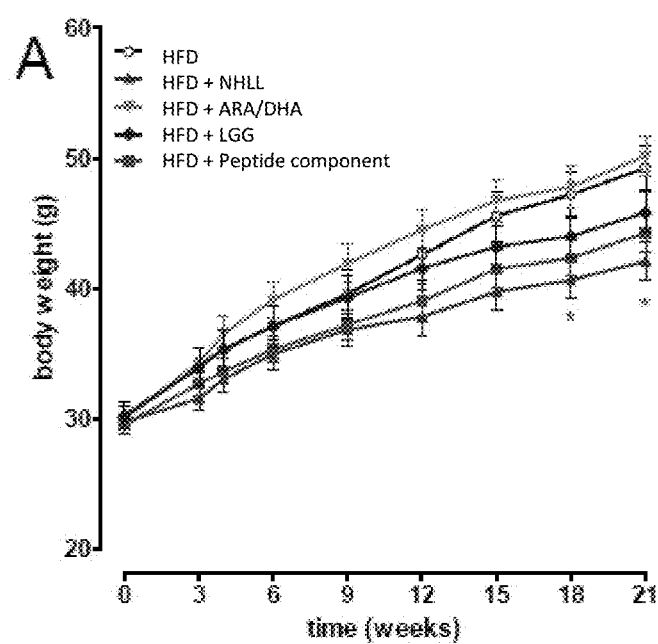
FIG. 1A illustrates body weight over 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.

Reference now will be made in detail to the embodiments of the present disclosure, one or more examples of which are set forth hereinbelow. Each example is provided by way of explanation of the nutritional supplement of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are apparent from the following detailed description. It is to be understood by one of ordinary skill in the art that the present discussion is a description of exemplary embodiments only and is not intended as limiting the broader aspects of the present disclosure.

The present disclosure relates generally to nutritional supplements comprising a peptide component. In some embodiments, the peptide component may comprise to following peptides: SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63. In some embodiments, the peptide component may comprise at least 10 additional peptides disclosed in Table 1.

When administered to individuals, the nutritional supplement including the peptide component, LCPUFA, and LGG has advantageous effects on metabolism, the inflammatory response, and cognition. For example, in some embodiments, the nutritional supplement reduces total cholesterol levels. In certain embodiments, the nutritional supplement reduces triglycerides.

"Nutritional composition" means a substance or formulation that satisfies at least a portion of a subject's nutrient requirements. The terms "nutritional(s)", "nutritional formula(s)", "enteral nutritional(s)", and "nutritional supplement(s)" are used as non-limiting examples of nutritional composition(s) throughout the present disclosure. Moreover, "nutritional composition(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults.

The term "enteral" means deliverable through or within the gastrointestinal, or digestive, tract. "Enteral administration" includes oral feeding, intragastric feeding, transpyloric administration, or any other administration into the digestive tract. "Administration" is broader than "enteral administration" and includes parenteral administration or any other route of administration by which a substance is taken into a subject's body.

The term "medical food" refers enteral compositions that are formulated or intended for the dietary management of a disease or disorder. A medical food may be a food for oral ingestion or tube feeding (nasogastric tube), may be labeled for the dietary management of a specific medical disorder, disease or condition for which there are distinctive nutritional requirements, and may be intended to be used under medical supervision.

The term "peptide" as used herein describes linear molecular chains of amino acids, including single chain molecules or their fragments. The peptides described herein, may include from about 2 total amino acids to about 50 total amino acids. In some embodiments, the peptides may include from about 2 total amino acids to about 75 amino acids. Still in some embodiments, the peptides may include from about 2 amino acids to about 100 amino acids. Further, in some embodiments, the peptide component may include peptides that have at least 2 total amino acids and no more than 50 total amino acids. Peptides may further form oligomers or multimers consisting of at least two identical or different molecules.

The term "peptide" may also refer to naturally modified peptides where the modification is effected, for example, by glycosylation, acetylation, phosphorylation and similar modification which are well known in the art. In some embodiments, the peptide component is distinguished from a protein source also disclosed herein. Further, peptides may, for example, be produced recombinantly, semi-synthetically, synthetically, or obtained from natural sources such as after hydrolysation of proteins, including but not limited to casein, all according to methods known in the art. Furthermore, peptidomimetics of such peptides where amino acid(s) and/or peptide bond(s) have been replaced by functional analogs are also encompassed by the term "peptide". Such functional analogues may include, but are not limited to, all known amino acids other than the 20 gene-encoded amino acids such as selenocysteine.

The term "peptide component" refers to at least one individual peptide, a plurality of individual peptides, and combinations thereof. For example, in some embodiments, the peptide component may comprise selected peptides from extensively hydrolyzed casein. In certain embodiments, the peptide component may comprise specific peptides identified by amino acid sequences, specific peptides selected from hydrolyzed protein, including extensively hydrolyzed protein and partially hydrolyzed protein, and combinations thereof.

The term "degree of hydrolysis" refers to the extent to which peptide bonds are broken by a hydrolysis method. For example, the protein equivalent source of the present disclosure may, in some embodiments comprise a protein having a degree of hydrolysis of no greater than 40%.

The term "partially hydrolyzed" means having a degree of hydrolysis which is greater than 0% but less than 50%.

The term "extensively hydrolyzed" means having a degree of hydrolysis which is greater than or equal to 50%.

The term "molar mass distribution" when used in reference to a hydrolyzed protein or protein hydrolysate pertains to the molar mass of each peptide present in the protein hydrolysate. For example, a protein hydrolysate having a molar mass distribution of greater than 500 Daltons means that each peptide included in the protein hydrolysate has a molar mass of at least 500 Daltons. Accordingly, in some embodiments, the peptides disclosed in Table 1 and Table 2 are derived from a protein hydrolysate having a molar mass distribution of greater than 500 Daltons. To produce a protein hydrolysate having a molar mass distribution of greater than 500 Daltons, a protein hydrolysate may be subjected to certain filtering procedures or any other procedure known in the art for removing peptides, amino acids, and/or other proteinaceous material having a molar mass of less than 500 Daltons. For the purposes of this disclosure, any method known in the art may be used to produce the protein hydrolysate having a molar mass distribution of greater than 500 Dalton.

The term "protein equivalent" or "protein equivalent source" includes any protein source, such as soy, egg, whey, or casein, as well as non-protein sources, such as peptides or amino acids. Further, the protein equivalent source can be any used in the art, e.g., nonfat milk, whey protein, casein, soy protein, hydrolyzed protein, amino acids, and the like.

Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate), soy bean proteins, and any combinations thereof. The protein equivalent source can, in some embodiments comprise hydrolyzed protein, including partially hydrolyzed protein and extensively hydrolyzed protein. The protein equivalent source may, in some embodiments, include intact protein.

The term "protein equivalent source" also encompasses free amino acids. In some embodiments, the amino acids may comprise, but are not limited to, histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof. In some embodiments, the amino acids may be branched chain amino acids. In certain other embodiments, small amino acid peptides may be included as the protein component of the nutritional supplement. Such small amino acid peptides may be naturally occurring or synthesized.

"Pediatric subject" means a human less than 13 years of age. In some embodiments, a pediatric subject refers to a human subject that is between birth and 8 years old. In other embodiments, a pediatric subject refers to a human subject between 1 and 6 years of age. In still further embodiments, a pediatric subject refers to a human subject between 6 and 12 years of age. The term "pediatric subject" may refer to infants (preterm or fullterm) and/or children, as described below.

"Infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. The term infant includes low birth weight infants, very low birth weight infants, and preterm infants. "Preterm" means an infant born before the end of the 37th week of gestation. "Full term" means an infant born after the end of the 37th week of gestation.

"Child" means a subject ranging in age from 12 months to about 13 years. In some embodiments, a child is a subject between the ages of 1 and 12 years old. In other embodiments, the terms "children" or "child" refer to subjects that are between one and about six years old, or between about seven and about 12 years old. In other embodiments, the terms "children" or "child" refer to any range of ages between 12 months and about 13 years.

"Children's nutritional product" refers to a composition that satisfies at least a portion of the nutrient requirements of a child. A growing-up milk is an example of a children's nutritional product.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

"Prebiotic" means a non-digestible food ingredient that beneficially affects the host by selectively stimulating the growth and/or activity of one or a limited number of bacteria in the digestive tract that can improve the health of the host.

"Probiotic" means a microorganism with low or no pathogenicity that exerts at least one beneficial effect on the health of the host.

The term "inactivated probiotic" means a probiotic wherein the metabolic activity or reproductive ability of the referenced probiotic organism has been reduced or destroyed. The "inactivated probiotic" does, however, still retain, at the cellular level, at least a portion its biological glycol-protein and DNA/RNA structure. As used herein, the term "inactivated" is synonymous with "non-viable". More specifically, a non-limiting example of an inactivated probiotic is inactivated *Lactobacillus rhamnosus* GG ("LGG") or "inactivated LGG".

All percentages, parts and ratios as used herein are by weight of the total formulation, unless otherwise specified.

The nutritional supplement of the present disclosure may be substantially free of any optional or selected ingredients described herein, provided that the remaining nutritional supplement still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods, supplements, and compositions of the present disclosure, including components thereof, can comprise, consist of, or consist essentially of the essential elements and limitations of the embodiments described herein, as well as any additional or optional ingredients, components or limitations described herein or otherwise useful in nutritional supplements.

As used herein, the term "about" should be construed to refer to both of the numbers specified as the endpoint(s) of any range. Any reference to a range should be considered as providing support for any subset within that range.

In some embodiments, the selected ingredients for incorporation in the nutritional supplement may be from a suitable non-human organism. Indeed, the selected ingredients disclosed herein may be synthetically produced, purified, modified, and/or fortified by well-known methods. Indeed, ingredients and additives incorporated into the nutritional supplement may be man-made and possess certain characteristics not observed in naturally occurring substances. In some embodiments, the ingredients and nutrients disclosed herein may possess certain physical and/or chemical characteristics distinct from any naturally occurring substance.

Obesity is a medical condition in which excess body fat has accumulated to such an extent that it causes an adverse effect on health. For example, obesity can lead to reduced life expectancy, heart disease, type 2 diabetes mellitus, obstructive sleep apnea, osteoarthritis, non-alcoholic fatty liver, and cognitive impairment. Experts hypothesize that obesity is one of the leading preventable causes of death worldwide, and has increasing prevalence in adults and children.

Metabolic syndrome is a term that generally describes a group of risk factors that raises the risk for certain diseases and health problems, for example heart disease, diabetes and strike. Generally, the risk for certain metabolic and cardiovascular diseases increases with the number of risk factors. Other metabolic risk factors include insulin resistance, which may increase the risk for metabolic syndrome.

Accordingly, the present disclosure relates generally to nutritional supplements comprising a peptide component that comprises SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, SEQ ID NO 63, and combinations thereof. In some embodiments, the peptide component may comprise additional peptides disclosed in Table 1. For example, the composition may include at least 10 additional peptides disclosed in Table 1. In some embodiments, 20% to 80% of the peptide component may include selected proteins from Table 1 and/or Table 2, and 20% to 80% of the peptide component may comprise a partially hydrolyzed protein, extensively hydrolyzed protein and combinations thereof. In some embodiments, the term "additional" means selecting different peptides than those enumerated.

In another embodiment 20% to 80% of the peptide component comprises at least 3 peptides selected from the group consisting of SEQ ID NO 4, SEQ ID NO 13, SEQ ID NO 17, SEQ ID NO 21, SEQ ID NO 24, SEQ ID NO 30, SEQ ID NO 31, SEQ ID NO 32, SEQ ID NO 51, SEQ ID NO 57, SEQ ID NO 60, and SEQ ID NO 63, and at least 5 additional peptides selected from Table 1; and wherein 20% to 80% of the peptide component comprises an a partially hydrolyzed protein, extensively hydrolyzed protein, or combinations thereof.

Table 1 below identifies the specific amino acid sequences that may be included in the peptide component of the nutritional supplement.

TABLE 1

| Seq ID | Amino Acid Sequence | (aa) |
|---|---|---|
| 1 | Ala Ile Asn Pro Ser Lys Glu Asn | 8 |
| 2 | Ala Pro Phe Pro Glu | 5 |
| 3 | Asp Ile Gly Ser Glu Ser | 6 |
| 4 | Asp Lys Thr Glu Ile Pro Thr | 7 |
| 5 | Asp Met Glu Ser Thr | 5 |
| 6 | Asp Met Pro Ile | 4 |
| 7 | Asp Val Pro Ser | 4 |
| n/a | Glu Asp Ile | 3 |
| n/a | Glu Leu Phe | 3 |
| n/a | Glu Met Pro | 3 |
| 8 | Glu Thr Ala Pro Val Pro Leu | 7 |
| 9 | Phe Pro Gly Pro Ile Pro | 6 |
| 10 | Phe Pro Gly Pro Ile Pro Asn | 7 |
| 11 | Gly Pro Phe Pro | 4 |
| 12 | Gly Pro Ile Val | 4 |
| 13 | Ile Gly Ser Glu Ser Thr Glu Asp Gln | 9 |
| 14 | Ile Gly Ser Ser Ser Glu Glu Ser | 8 |
| 15 | Ile Gly Ser Ser Ser Glu Glu Ser Ala | 9 |
| 16 | Ile Asn Pro Ser Lys Glu | 6 |
| 17 | Ile Pro Asn Pro Ile | 5 |
| 18 | Ile Pro Asn Pro Ile Gly | 6 |
| 19 | Ile Pro Pro Leu Thr Gln Thr Pro Val | 9 |
| 20 | Ile Thr Ala Pro | 4 |
| 21 | Ile Val Pro Asn | 4 |
| 22 | Lys His Gln Gly Leu Pro Gln | 7 |
| 23 | Leu Asp Val Thr Pro | 5 |
| 24 | Leu Glu Asp Ser Pro Glu | 6 |
| 25 | Leu Pro Leu Pro Leu | 5 |
| 26 | Met Glu Ser Thr Glu Val | 6 |
| 27 | Met His Gln Pro His Gln Pro Leu Pro Pro Thr | 11 |
| 28 | Asn Ala Val Pro Ile | 5 |
| 29 | Asn Glu Val Glu Ala | 5 |
| n/a | Asn Leu Leu | 3 |
| 30 | Asn Gln Glu Gln Pro Ile | 6 |
| 31 | Asn Val Pro Gly Glu | 5 |
| 32 | Pro Phe Pro gly Pro Ile | 6 |
| 33 | Pro Gly Pro Ile Pro Asn | 6 |
| 34 | Pro His Gln Pro Leu Pro Pro Thr | 8 |
| 35 | Pro Ile Thr Pro Thr | 5 |
| 36 | Pro Asn Pro Ile | 4 |
| 37 | Pro Asn Ser Leu Pro Gln | 6 |
| 38 | Pro Gln Leu Glu Ile Val Pro Asn | 8 |
| 39 | Pro Gln Asn Ile Pro Pro Leu | 7 |
| 40 | Pro Val Leu Gly Pro Val | 6 |
| 41 | Pro Val Pro Gln | 4 |
| 42 | Pro Val Val Val Pro | 5 |
| 43 | Pro Val Val Val Pro Pro | 6 |
| 44 | Ser Ile Gly Ser Ser Ser Glu Glu Ser Ala Glu | 11 |
| 45 | Ser Ile Ser Ser Ser Glu Glu | 7 |
| 46 | Ser Ile Ser Ser Ser Glu Glu Ile Val Pro Asn | 11 |
| 47 | Ser Lys Asp Ile Gly Ser Glu | 7 |
| 48 | Ser Pro Pro Glu Ile Asn | 6 |
| 49 | Ser Pro Pro Glu Ile Asn Thr | 7 |
| 50 | Thr Asp Ala Pro Ser Phe Ser | 7 |
| 51 | Thr Glu Asp Glu Leu | 5 |
| 52 | Val Ala Thr Glu Glu Val | 6 |
| 53 | Val Leu Pro Val Pro | 5 |
| 54 | Val Pro Gly Glu | 4 |
| 55 | Val Pro Gly Glu Ile Val | 6 |
| 56 | Val Pro Ile Thr Pro Thr | 6 |
| 57 | Val Pro Ser Glu | 4 |
| 58 | Val Val Pro Pro Phe Leu Gln Pro Glu | 9 |
| 59 | Val Val Val Pro Pro | 5 |
| 60 | Tyr Pro Phe Pro Gly Pro | 6 |
| 61 | Tyr Pro Phe Pro Gly Pro Ile Pro | 8 |
| 62 | Tyr Pro Phe Pro Gly Pro Ile Pro Asn | 9 |
| 63 | Tyr Pro Ser Gly Ala | 5 |
| 64 | Tyr Pro Val Glu Pro | 5 |

Table 2 below further identifies a subset of amino acid sequences from Table 1 that may be included and/or comprise the peptide component disclosed herein.

TABLE 2

| Seq ID | Amino Acid Sequence | (aa) |
|---|---|---|
| 4 | Asp Lys Thr Glu Ile Pro Thr | 7 |
| 13 | Ile Gly Ser Glu Ser Thr Glu Asp Gln | 9 |
| 17 | Ile Pro Asn Pro Ile Gly | 6 |
| 21 | Ile Val Pro Asn | 4 |
| 24 | Leu Glu Asp Ser Pro Glu | 6 |
| 30 | Asn Gln Glu Gln Pro Ile | 6 |
| 31 | Asn Val Pro Gly Glu | 5 |
| 32 | Pro Phe Pro Gly Pro Ile | 6 |
| 51 | Thr Glu Asp Glu Leu | 5 |
| 57 | Val Pro Ser Glu | 4 |
| 60 | Tyr Pro Phe Pro Gly Pro | 6 |
| 63 | Tyr Pro Ser Gly Ala | 5 |

In some embodiments, the peptides identified in Tables 1 and 2, may be provided by a protein equivalent source obtained from cow's milk proteins, including but not limited to bovine casein and bovine whey. In some embodiments, the protein equivalent source comprises hydrolyzed bovine casein or hydrolyzed bovine whey. Accordingly, in some embodiments, the peptides identified in Table 1 and Table 2 may be provided by a casein hydrolysate. Such peptides may be obtained by hydrolysis or may be synthesized in vitro by methods know to the skilled person. A nonlimiting example of a method of hydrolysis utilizing a proteolytic enzyme is disclosed in U.S. Pat. No. 7,618,669 to Rangavajla et al., which is hereby incorporated by reference in its entirety. However, other methods of hydrolysis may be used in practice of the present disclosure.

In some embodiments, the peptide component may comprise from about 5% to about 100% of selected peptides identified in Tables 1 and 2. Still in some embodiments, the peptide component may comprise from about 10% to about 90% of selected peptides identified in Tables 1 and 2. In some embodiments, the peptide component may comprise from about 15% to about 80% of selected peptides identified in Tables 1 and 2. In some embodiments, the peptide component may comprise from about 25% to about 65% of selected peptides identified in Tables 1 and 2.

The peptide component may, in some embodiments, include peptides present in extensively hydrolyzed protein, partially hydrolyzed protein, and combinations thereof. In some embodiments, the peptide component may comprise from about 5% to about 100% of peptides from extensively hydrolyzed protein, partially hydrolyzed protein, or combinations thereof. In some embodiments, the peptide component may comprise from about 10% to about 90% of peptides from extensively hydrolyzed protein, partially hydrolyzed protein, or combinations thereof. In some embodiments, the peptide component may comprise from about 15% to about 80% of peptides from extensively hydrolyzed protein, partially hydrolyzed protein, or combinations thereof. In some embodiments, the peptide component may comprise from about 25% to about 65% of peptides from extensively hydrolyzed protein, partially hydrolyzed protein, or combinations thereof. In some embodiments, the extensively hydrolyzed protein is extensively hydrolyzed casein. In some embodiments, the partially hydrolyzed protein is casein.

In some embodiments, the peptide component comprises a hydrolyzed protein, which includes partially hydrolyzed protein and extensively hydrolyzed protein. In other embodiments, the peptide component comprises a hydrolyzed protein including peptides having a molar mass distribution of greater than 500 Daltons. In certain embodiments, the hydrolyzed protein comprises peptides having a molar mass distribution in the range of from about 100 Daltons to about 3,000 Daltons. Still, in some embodiments the hydrolyzed protein may comprise peptides having a molar mass distribution range of from about 500 Daltons to about 2,500 Daltons.

In some embodiments the peptide component comprises partially hydrolyzed protein having a degree of hydrolysis of less than 40%. In still other embodiments, the peptide component may comprise partially hydrolyzed protein having a degree of hydrolysis of less than 25%, or less than 15%.

In some embodiments, the peptide component may be formulated in the nutritional supplement to be provided in certain amounts per day depending on the target subject. For example, in some embodiments, the peptide component may be formulated to provide from about 5 grams/day to about 15 grams per day to a target subject. In certain embodiments, the peptide component may be formulated to provide from about 5 grams/day to about 15 grams per day to a target subject that is an infant (between 0-1 years of age). In some embodiments, the peptide component is formulated to provide from about 7 grams/day to about 11 grams/day to a target subject. Still in other embodiments, the peptide component may be formulated to provide from about 8 grams/day to about 10 grams/day.

In embodiments where the target subject is a child between the ages of 1-3 years, the peptide component may be formulated in the nutritional supplement to be provided at an amount of from about 10 grams/day to about 20 grams/day. Still in some embodiments where the target subject is a child between the age of 1-3 years, the peptide component may be formulated in the nutritional supplement to be provided at an amount of from about 13 grams/day to about 18 grams/day.

In embodiments where the target subject is a child between the ages of 4-8 years, the peptide component may be formulated in the nutritional supplement to be provided at an amount of from about 10 grams/day to about 25 grams/day. Still in some embodiments where the target subject is a child between the ages of 4-8 years, the peptide component may be formulated in the nutritional supplement to be provided at an amount of from about 13 grams/day to about 19 grams/day.

In embodiments where the target subject is between the ages of 9-13 years, the peptide component may be formulated in the nutritional supplement to be provided at an amount of from about 15 grams/day to about 40 grams/day. Still in some embodiments where the target is between the ages of 1-3 years, the peptide component may be formulated in the nutritional supplement to be provided at an amount of from about 20 grams/day to about 35 grams/day.

In embodiments where the target subject is between the ages of 14-18 years, the peptide component may be formulated in the nutritional supplement to be provided at an amount of from about 30 grams/day to about 60 grams/day. Still in some embodiments where the target subject is between the ages of 14-18 years, the peptide component may be formulated in the nutritional supplement to be provided at an amount of from about 35 grams/day to about 52 grams/day.

In embodiments where the target subject is over 18 years of age, the peptide component may be formulated in the nutritional supplement to be provided at an amount of from about 45 grams/day to about 65 grams/day. Still in some embodiments where the target subject is over 18 years of age, the peptide component may be formulated in the nutritional supplement to be provided at an amount of from about 50 grams/day to about 60 grams/day.

In some embodiments, the peptide component may provide the sole source of protein nutrition to the target subject. In some embodiments, the nutritional supplement is formulated such that 10-35% of the total daily calories are provided from the peptide component. In some embodiments, the peptide component may be formulated to provide from about 5% to about 15% of the total daily calories.

In some embodiments, the nutritional supplement may include the peptide component in an amount of from about 0.2 g/100 kcal to about 5.6 g/100 kcal. In other embodiments the peptide component may be present in the nutritional supplement in an amount from about 1 g/100 kcal to about 4 g/100 kcal. In still other embodiments, the peptide component may be present in the nutritional supplement in an amount from about 2 g/100 kcal to about 3 g/100 kcal.

In some embodiments, the peptide component may be included in a nutritional supplement or composition as the sole source of proteinaceous material. In still other embodiments, the peptide component may be included in a nutritional supplement or composition that further comprises intact protein, amino acids, and combinations thereof.

In certain embodiments, the nutritional supplement may include a protein equivalent source. In certain embodiments, the protein equivalent source may comprise the peptide component described herein. In some embodiments, the protein equivalent source may comprise free amino acids. In certain other embodiments, small amino acid peptides may be included in the protein equivalent source. Such small amino acid peptides may be naturally occurring or synthesized. The amount of free amino acids in the nutritional supplement may vary from about 1 g/100 kcal to about 5 g/100 kcal.

In some embodiments, the protein equivalent source may include hydrolyzed protein. For example, in some embodiments the protein equivalent source may include the peptide component as described herein and further comprise extensively hydrolyzed protein, partially hydrolyzed protein, and combinations thereof. In some embodiments from about 5% to about 95% of the protein equivalent source may be comprised of the peptide component described herein and 5% to about 95% of the protein equivalent source may comprise extensively hydrolyzed protein, partially hydrolyzed protein, amino acids, and/or combinations thereof. In some embodiments from about 20% to about 80% of the protein equivalent source may be comprised of the peptide component described herein and 20% to about 80% of the protein equivalent source may comprise extensively hydrolyzed protein, partially hydrolyzed protein, amino acids, and/or combinations thereof.

In some embodiments, the nutritional supplement comprises between about 1 g and about 7 g of a protein equivalent source per 100 kcal. In other embodiments, the nutritional supplement comprises between about 3.5 g and about 4.5 g of protein equivalent source per 100 kcal.

In some embodiments, where the peptide component is provided as part of a protein equivalent source, the protein equivalent source may be present in the nutritional supplement in an amount of from about 0.2 g/100 kcal to about 5.6 g/100 kcal. In some other embodiments, where the peptide component is provided as part of a protein equivalent source, the protein equivalent source may be present in the nutritional supplement in an amount of from about 1 g/100 kcal to about 4 g/100 kcal. In still other embodiments, where the peptide component is provided as part of a protein equivalent source, the protein equivalent source may be present in the nutritional supplement in an amount of from about 2 g/100 kcal to about 3 g/100 kcal.

The nutritional supplement of the present disclosure may also contain a source of long chain polyunsaturated fatty acids ("LCPUFAs"). Suitable LCPUFAs include, but are not limited to DHA, eicosapentaenoic acid ("EPA"), ARA, linoleic (18:2 n-6), γ-linolenic (18:3 n-6), dihomo-γ-linolenic (20:3 n-6) acids in the n-6 pathway, α-linolenic (18:3 n-3), stearidonic (18:4 n-3), eicosatetraenoic (20:4 n-3), eicosapentaenoic (20:5 n-3), and docosapentaenoic (22:6 n-3).

The amount of LCPUFA in the nutritional supplement is at least about 5 mg/100 kcal, and may vary from about 5 mg/100 kcal to about 100 mg/100 kcal, more preferably from about 10 mg/100 kcal to about 50 mg/100 kcal.

Sources of LCPUFAs include dairy products like eggs and butterfat; marine oils, such as cod, menhaden, sardine, tuna and many other fish; certain animal fats, lard, tallow and microbial oils such as fungal and algal oils, or from any other resource fortified or not, form which LCPUFAs could be obtained and used in a nutritional supplement. The LCPUFA could be part of a complex mixture obtained by separation technology known in the art aimed at enrichment of LCPUFAs and the derivatives or precursors of LCPUFAs in such mixtures.

The LCPUFAs may be provided in the nutritional supplement in the form of esters of free fatty acids; mono-, di- and tri-glycerides; phosphoglycerides, including lecithins; and/or mixtures thereof. Additionally, LCPUFA may be provided in the nutritional supplement in the form of phospholipids, especially phosphatidylcholine.

In an embodiment the nutritional supplement comprises both DHA and ARA. In this embodiment, the weight ratio of ARA:DHA may be between about 1:3 and about 9:1. In a particular embodiment, the weight ratio of ARA:DHA is from about 1:2 to about 4:1.

DHA is advantageously present in the nutritional supplement, in some embodiments, from at least about 17 mg/100 kcal, and may vary from about 5 mg/100 kcal to about 75 mg/100 kcal. In some embodiments, DHA is present from about 10 mg/100 kcal to about 50 mg/100 kcal.

The nutritional supplement may comprise oils containing DHA and/or ARA using standard techniques known in the art. If utilized, the source of DHA and/or ARA may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the target subject. Alternatively, the DHA and ARA can be used in refined form.

In an embodiment, sources of DHA and ARA are single cell oils as taught in U.S. Pat. Nos. 5,374,567; 5,550,156; and 5,397,591, the disclosures of which are incorporated herein in their entirety by reference. However, the present disclosure is not limited to only such oils.

Furthermore, especially where the nutritional supplement is incorporated into an infant formula, the nutritional supplement may comprise a higher amount of some nutritional components than does human milk. For example, the nutritional supplement may comprise a greater amount of DHA than does human breast milk. The enhanced level of DHA of the nutritional supplement may compensate for an existing nutritional DHA deficit.

The nutritional supplement also includes *Lactobacillus rhamnosus* GG (LGG)(ATCC number 53101). In some embodiments, the nutritional supplement may also contain one or more additional probiotics. Any probiotic known in the art may be acceptable in this embodiment. In a particular embodiment, the probiotic may be selected from another *Lactobacillus* species, *Bifidobacterium* species, *Bifidobacterium longum* BB536 (BL999, ATCC: BAA-999), *Bifidobacterium longum* AH1206 (NCIMB: 41382), *Bifidobacterium breve* AH1205 (NCIMB: 41387), *Bifidobacterium infantis* 35624 (NCIMB: 41003), and *Bifidobacterium animalis* subsp. *lactis* BB-12 (DSM No. 10140) or any combination thereof.

In some embodiments, the amount of the probiotic in the nutritional supplement may vary from about $1 \times 10^4$ to about $1.5 \times 10^{10}$ cfu of probiotics per 100 kcal, more preferably from about $1 \times 10^6$ to about $1 \times 10^9$ cfu of probiotics per 100 kcal. In certain other embodiments the amount of probiotics may vary from about $1 \times 10^7$ cfu/100 kcal to about $1 \times 10^8$ cfu/100 kcal.

In some embodiments, the probiotics may be formulated in the nutritional supplement to provide from about $0.1 \times 10^9$ to about $1.7 \times 10^9$ cfu per day to a target subject. In some embodiments, the probiotics may be formulated in the nutritional supplement to provide from about $0.4 \times 10^9$ to about $1 \times 10^9$ cfu per day to a target subject. In still other embodiments, the probiotics may be formulated in the nutritional supplement to provide from about $0.6 \times 10^9$ to about $0.8 \times 10^9$ cfu per day to a target subject.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such source is now known or later developed.

Surprisingly, when the peptide component described herein was tested in conjunction with LGG, ARA and DHA supplementation, a reduction in weight gain in an experimental animal model of obesity and type 2 diabetes was observed. Additionally, the administration of the peptide component described herein, with LGG, ARA and DHA exhibited a beneficial effect on body mass composition. For example, a reduction in overall fat mass, lower fasting insulin and lower cholesterol levels were observed.

Accordingly, in some embodiments, the nutritional supplements include a peptide component, LGG, and at least one long chain polyunsaturated fatty acid, selected from ARA, DHA, and combinations thereof. Without being bound by any particular theory, it is believed that a combination of these elements provides synergistic health benefits, such as promoting fat loss and lowering cholesterol and triglyceride levels.

Moreover, in some embodiments, the nutritional supplement including the peptide component, LCPUFA, and LGG may be used in the dietary management of obesity to reduce existing obesity and metabolic conditions, reduce existing metabolic risk factors, and/or prevent additional metabolic conditions. Additionally, the nutritional supplement disclosed herein including the peptide component, may be provided to a target subject to mitigate current risk factors for obesity and underlying metabolic conditions and/or to allow the target subject to manage ongoing metabolic risk factors. In some embodiments, the nutritional supplement, including the peptide component, LCPUFA and LGG, may be provided to a target subject to help manage and promote metabolic diseases risk factor reduction.

The nutritional supplement(s) of the present disclosure including the peptide component, LCPUFA, and LGG, may be administered in one or more doses daily. Any orally acceptable dosage form is contemplated by the present disclosure. Examples of such dosage forms include, but are not limited to pills, tablets, capsules, soft-gels, liquids, liquid concentrates, powders, elixirs, solutions, suspensions, emulsions, lozenges, beads, cachets, and combinations thereof.

In some embodiments, the nutritional supplement comprising the peptide component, LCPUFA, and LGG may be added to a more complete nutritional product. In this embodiment, the nutritional product may contain additional, fat, protein and carbohydrate sources or components and may be used to supplement the diet or may be used as the sole source of nutrition.

Additionally, the nutritional supplement may be added or incorporated into a nutritional composition by any method well known in the art. In some embodiments, the nutritional supplement disclosed herein may be added to a nutritional composition to supplement the nutritional composition. For example, in one embodiment, the nutritional supplement of the present disclosure may be added to a commercially available infant formula. For example, Enfalac, Enfamil®, Enfamil® Premature Formula, Enfamil® with Iron, Enfamil® LCPUFA®, Lactofree®, Nutramigen®, Pregestimil®, and ProSobee® (available from Mead Johnson & Company, Evansville, Ind., U.S.A.) may be supplemented with a suitable amount of the nutritional supplement, and used in practice of the present disclosure.

In some embodiments, the nutritional supplement comprises at least one carbohydrate source. The carbohydrate source can be any used in the art, e.g., lactose, glucose, fructose, corn syrup solids, maltodextrins, sucrose, starch, rice syrup solids, and the like. The amount of the carbohydrate component in the nutritional supplement typically can vary from between about 5 g/100 kcal and about 25 g/100 kcal. In some embodiments, the amount of carbohydrate is between about 6 g/100 kcal and about 22 g/100 kcal. In other embodiments, the amount of carbohydrate is between about 12 g/100 kcal and about 14 g/100 kcal. In some embodiments, corn syrup solids are preferred. Moreover, hydrolyzed, partially hydrolyzed, and/or extensively hydrolyzed carbohydrates may be desirable for inclusion in the nutritional supplement due to their easy digestibility. Specifically, hydrolyzed carbohydrates are less likely to contain allergenic epitopes.

Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

The nutritional supplement may also comprise a fat or lipid source. Suitable fat or lipid sources for the nutritional supplement of the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

In some embodiment the nutritional supplement comprises between about 1.3 g/100 kcal to about 7.2 g/100 kcal of a fat or lipid source. In other embodiments the fat or lipid source may be present in an amount from about 2.5 g/100 kcal to about 6.0 g/100 kcal. In still other embodiments, the fat of lipid source may be present in the nutritional supplement in an amount from about 3.0 g/100 kcal to about 4.0 g/100 kcal.

The nutritional supplement may also contain one or more prebiotics (also referred to as a prebiotic source) in certain embodiments. Prebiotics can stimulate the growth and/or activity of ingested probiotic microorganisms, selectively reduce pathogens found in the gut, and favorably influence the short chain fatty acid profile of the gut. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide, and gentio-oligosaccharides.

In some embodiments, the total amount of prebiotics present in the nutritional supplement may be from about 0.1 g/100 kcal to about 1 g/100 kcal. In certain embodiments, the total amount of prebiotics present in the nutritional supplement may be from about 0.3 g/100 kcal to about 0.7 g/100 kcal.

Moreover, the nutritional supplement may comprise a prebiotic component comprising polydextrose ("PDX") and/or galacto-oligosaccharide ("GOS"). In some embodiments, the prebiotic component comprises at least 20% GOS, PDX or a mixture thereof. If PDX is used in the prebiotic composition, the amount of PDX in the nutritional supplement may, in an embodiment, be within the range of from about 0.1 g/100 kcal to about 1 g/100 kcal. In another embodiment, the amount of polydextrose is within the range of from about 0.2 g/100 kcal to about 0.6 g/100 kcal. And in still other embodiments, the amount of PDX in the nutritional supplement may be from about 0.1 mg/100 kcal to about 0.5 mg/100 kcal.

If GOS is used in the prebiotic composition, the amount of GOS in the nutritional supplement may, in an embodiment, be from about 0.1 g/100 kcal to about 1 g/100 kcal. In another embodiment, the amount of GOS in the nutritional supplement may be from about 0.2 g/100 kcal to about 0.5 g/100 kcal. In other embodiments, the amount of GOS in the nutritional supplement may be from about 0.1 mg/100 kcal to about 1.0 mg/100 kcal or from about 0.1 mg/100 kcal to about 0.5 mg/100 kcal.

In some embodiments, the nutritional supplement(s) of the present disclosure may comprise a culture supernatant from a late-exponential growth phase of a probiotic batch-cultivation process (hereinafter referred to as the "culture supernatant"); in specific embodiments, the probiotic is LGG and can be incorporated as the LGG component. Batch cultivation culture supernatant (which can also be referred to as "spent medium") may possess protection against pathogen infection, including infection by $C.\ sakazakii$. Specifically the harvested culture supernatant may prevent the invasion of $C.\ sakazakii$ to organs such as the brain and reduce mortality associated with $C.\ sakazakii$.

In some embodiments, the nutritional supplement comprises a culture supernatant from a late-exponential growth phase of a probiotic batch-cultivation process, for use in the treatment or prevention of pathogen infection. In certain embodiments, the probiotic is LGG, and the pathogen is $C.\ sakazakii$.

Without wishing to be bound by theory, it is believed that the activity of the culture supernatant can be attributed to the mixture of components (including proteinaceous materials, and possibly including (exo)polysaccharide materials) as found released into the culture medium at a late stage of the exponential (or "log") phase of batch cultivation of LGG. The chemical composition of the culture supernatant is believed to be a mixture of a plurality of amino acids, oligo- and polypeptides, and proteins, of various molecular weights. The culture supernatant may further comprise polysaccharide structures and/or nucleotides. In some embodiments the culture supernatant pertains to the entire, i.e. unfractionated culture supernatant. Further, in some embodiments the culture supernatant pertains to the entire, i.e. unfractionated culture supernatant.

In some embodiments, a composition according to the disclosure and/or embodiments thereof is obtainable by a process comprising the steps of (a) subjecting a probiotic such as LGG to cultivation in a suitable culture medium using a batch process; (b) harvesting the culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5 kiloDaltons (kDa) or even above 6 kDa; (d) removing liquid contents from the culture supernatant so as to obtain the composition.

In addition to the foregoing, it should be noted that the batch cultivation of lactobacilli, including LGG, is common general knowledge available to the person skilled in the art. These methods thus do not require further elucidation here. The culture supernatant of the present disclosure can be harvested by any known technique for the separation of culture supernatant from a bacterial culture. Such techniques are well-known in the art and include, e.g., centrifugation, filtration, sedimentation, and the like.

In some embodiments the nutritional supplement may comprise biofunctional peptides. Without being bound by any particular theory, it is believed that the combination of biofunctional peptides with the nutritional supplement including a peptide component, LCPUFA, and LGG, may provide synergistic health benefits. These synergistic benefits may influence body weight development, lipid metabolism, insulin resistance or other obesity or inflammatory related outcomes.

The disclosed nutritional supplement(s) may be provided in any form known in the art, such as a powder, a gel, a suspension, a paste, a solid, a liquid, a liquid concentrate, a reconstituteable powdered milk substitute or a ready-to-use product. The nutritional supplement may, in certain embodiments, be added or incorporated into a children's nutritional product, infant formula, human milk fortifier, growing-up milk or any other nutritional composition designed for an infant or a pediatric subject. The nutritional supplement of the present disclosure may be included, for example, in any orally-ingestible, health-promoting substances including, for example, foods, beverages, tablets, capsules and powders. Moreover, the nutritional supplement of the present disclosure may be standardized to a specific caloric content, it may be provided as a ready-to-use product, or it may be provided in a concentrated form. In some embodiments, the nutritional supplement is in powder form with a particle size in the range of 5 μm to 1500 μm, more preferably in the range of 10 μm to 300 μm.

If the nutritional supplement is in the form of a ready-to-use product, the osmolality of the nutritional supplement may be between about 100 and about 1100 mOsm/kg water, more typically about 200 to about 700 mOsm/kg water.

In certain embodiments, the nutritional supplement is hypoallergenic. In other embodiments, the nutritional supplement is kosher and/or halal. In still further embodiments, the nutritional supplement contains non-genetically modified ingredients. In an embodiment, the nutritional supplement is sucrose-free. The nutritional supplement may also be lactose-free. In other embodiments, the nutritional supplement does not contain any medium-chain triglyceride oil. In some embodiments, no carrageenan is present in the supplement. In other embodiments, the nutritional supplement is free of all gums.

The nutritional supplement of the present disclosure is not limited to compositions comprising nutrients specifically listed herein. Any nutrients may be delivered as part of the supplement for the purpose of meeting nutritional needs and/or in order to optimize the nutritional status in a subject.

Moreover, in some embodiments, the nutritional supplement may optionally include any number of proteins, peptides, amino acids, fatty acids, probiotics and/or their metabolic by-products, prebiotics, carbohydrates and any other nutrient or other compound that may provide many nutritional and physiological benefits to a subject. Further, the nutritional supplement of the present disclosure may comprise flavors, flavor enhancers, sweeteners, pigments, vitamins, minerals, therapeutic ingredients, functional food ingredients, food ingredients, processing ingredients or combinations thereof.

In some embodiments, the nutritional supplement of the present disclosure may be added to a growing-up milk. Growing-up milks are fortified milk-based beverages intended for children over 1 year of age (typically from 1-3 years of age, from 4-6 years of age or from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of a nutritional supplement according to the present disclosure can vary from market-to-market, depending on local regulations and dietary intake information of the population of interest. In some embodiments, nutritional supplements according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

One or more vitamins and/or minerals may also be added in to the nutritional supplement in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional supplement to a particular age group but, rather, to provide a range of acceptable vitamin and mineral components.

In embodiments providing a nutritional supplement for a child, the nutritional supplement may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E (α-tocopherol, α-tocopherol acetate, α-tocopherol succinate, α-tocopherol nicotinate, α-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, β-carotene and any combinations thereof.

In embodiments providing a children's nutritional product having the nutritional supplement of the present disclosure incorporated therein, such as a growing-up milk, the children's nutritional product may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolinate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to growing-up milks or to other children's nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the children's nutritional composition may contain between about 10 and about 50% of the maximum dietary recommendation for any given country, or between about 10 and about 50% of the average dietary recommendation for a group of countries, per serving, of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The nutritional supplement(s) of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, grape and or grape seed extracts, apple extract, bilberry extract or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional supplements of the present disclosure may optionally include one or more emulsifiers that may be added for stability of the final product. Examples of suitable emulsifiers include, but are not limited to, lecithin (e.g., from egg or soy or any other plant and animal sources), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional supplements of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional supplements of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, CITREM, and mixtures thereof.

The present disclosure further provides a method for promoting and/or maintaining a healthy body weight by providing a nutritional supplement comprising a peptide component, LCPFUA, and LGG as disclosed herein to a target subject.

Further provided are methods for preventing or protecting against the development of obesity, type 2 diabetes, cardiovascular disease, hepatosteatosis, impaired cognition, and/or kidney function in a target subject by providing a nutritional supplement including a peptide component, LGG, and LCPUFA to the target subject. Additionally, provided are method(s) for reducing the main risks for metabolic syndrome in a target subject by providing a nutritional supplement including a peptide component, LGG, and LCPUFA to the target subject.

In some embodiments, when the nutritional supplement disclosed herein is provided or administered to the target subject, the target subject may experience a reduction in body fat mass, cholesterol, insulin resistance, and vascular and chronic inflammation, and combinations thereof. The administration of the nutritional supplement disclosed herein may provide the following health benefits: lower body weight despite similar food intake, lower fasting insulin, lower plasma cholesterol, lower plasma triglycerides, lower Serum Amyloid A ("SAA"; a systemic inflammation marker), lower microalcuminurea, lower mesenteric fat, lower inguinal fat, lower epididymal fat, lower liver mass, lower circulating ALT levels, and combinations thereof. Without being bound by any particular theory, administration of the nutritional supplement including the combination of the peptide component, LGG and LCPUFA may provide synergistic and/or additive health benefits.

Further, the present disclosure may be directed to methods of dietary management for target subjects who have underlying metabolic risk factors or are obese. For example, provided herein are methods for the dietary management of metabolic risk factors comprising providing the nutritional supplement disclosed herein to a target subject. Still further, some embodiments provided herein are methods for disease risk factor reduction in a target subject by providing the nutritional supplement comprising the peptide component, LGG, ARA, and DHA to the target subject.

Additionally, provided herein are methods for improving cognition and/or protecting against impaired cognition in a target subject via providing the nutritional supplement including a peptide component, LGG, and LCPUFA to the target subject. Administration of the nutritional supplement including the peptide component, LGG, and LCPUFA may beneficially influence brain function, including providing regulated levels of gene expression related to brain inflammation, blood brain barrier, and brain function. Further provided herein are methods for increasing brain-derived neurotrophic factor (BDNF) gene expression in a target subject by providing a nutritional supplement comprising the peptide component, LCPUFA, and LGG as disclosed herein. Further, disclosed here in are methods for promoting the survival of neurons and/or promoting growth and differentiation of new neurons in a target subject by providing the nutritional supplement disclosed herein to the target subject. In some embodiments, the disclosure is directed to methods of enhancing synapse formation and promoting long term memory in a target subject by providing the nutritional supplement disclosed herein to the target subject.

In certain embodiments, the present disclosure is directed to promoting vascular integrity in the blood vessel walls within the brain of a target subject by providing the nutritional supplement comprising a peptide component, LGG, and LCPUFA to the target subject. Still in some embodiments, the present disclosure is directed to methods of reducing brain inflammation in a target subject by providing the nutritional supplement comprising a peptide component, LGG, and LCPUFA to the target subject.

In some embodiments the target subject may be a pediatric subject. Further, in one embodiment, the nutritional supplement provided to the pediatric subject may be incorporated in an infant formula or growing-up milk. The nutritional supplement identified herein and added to the infant formula may include a peptide component, LCPUFA, and LGG each selected from a specific source and concentrations of each may be adjusted to maximize health benefits. In another embodiment of this method, the nutritional supplement disclosed herein may be added to a growing up milk.

In embodiments when the nutritional supplement is added to an infant formula, the composition may advantageously protect against the development of obesity, type 2 diabetes, cardiovascular disease, hepatosteatosis, impaired cognition, and kidney function. More particularly, in some embodiments, an infant who consumes the aforementioned infant formula may, in some embodiments, experience these beneficial effects throughout childhood and into adulthood. Similarly, when the nutritional supplement is added to a growing-up milk, a child who ingests the growing-up milk may experience these beneficial effects into adulthood, as well as during childhood.

EXAMPLES

Studies were performed using a study design as summarized in Table 3 below. In short, these mice received for 21 weeks, starting at the age of 12 weeks (which is considered comparable to human adolescence), a high fat diet (45 Kcal % from lard) plus or minus the combination of a peptide component, LCPUFA, and LGG. Both the high fat diet and the tested diets with the peptide component, LCPUFA, and LGG were isocaloric. A control diet (low fat, 10% kcal by fat) served as a reference group.

The first study, indicated as Study 1 in Table 3 below, compared the mice on the high fat diet, to mice on a high fat diet supplemented with a combination of the peptide component, LCPUFA, and LGG. Whereas, the second study, indicated as Study 2 in Table 3 below, examined the effects on the mice of the individual ingredients.

TABLE 3

Table 3. Study Arms of Two Independent studies in LDLr KO mouse model

| Study 1 | Study 2 |
|---|---|
| Low Fat Diet (LFD) | |
| High Fat Diet (HFD) | High Fat Diet (HFD) |
| High fat Diet (+gavage PBS) | High fat Diet + Peptide component (casein in HFD replaced) |
| Combined Intervention: High fat diet + Peptide component, LCPUFA, and LGG. Protein in the HFG was replaced by Peptide component, Lard was corrected for 0.158% w/w ARA and 0.079% w/w DHA; LGG was provided by gavage (3x per week) | Combined Intervention: High fat diet + Peptide component, LCPUFA, and LGG. Protein in the HFG was replaced by Peptide component, Lard was corrected for 0.158% w/w ARA and 0.079% w/w DHA; LGG was provided by gavage (3x per week) |
| | High fat diet + 0.158% w/w ARA and 0.079% w/w DHA (lard corrected) |
| | High fat diet + LGG (gavage) |
| | High Fat Diet + >500 Da fraction of Peptide component (casein replaced in HFD) |

Further results demonstrate that food intake was comparable between all groups and comparable over the course of each study.

Example 1

Example 1 describes the experimental procedures for evaluating metabolic, and cardiovascular risk factors in LDLr knockout mice fed and HFD and supplemented with a peptide component, LCPUFA, and LGG.

The mice used were LDLr knockout mice, which phenotypically express the main risk factors that are characteristic for metabolic syndrome and that are hallmarks of human disease. Experiments were performed to conform to the rules and regulations set forward by the Netherlands Law on Animal Experiments and were approved by a Committee on Animal Experiments (DEC; approval number 3486).

Sixty-seven male LDLr−/− mice (11-18 weeks of age at the start of the experiment) obtained from the breeding facility at TNO were used. Animals were housed in macrolon cages (3-5 mice per cage) during the experiment at TNO Gaubius Building Leiden in clean-conventional animal rooms (relative humidity 50-60%, temperature ~21° C., light cycle 7 am to 7 μm). Mice were supplied with food and acidified tap water ad lib. Mice were fed standard lab chow (Ssniff R/M diet V1530, Uden, The Netherlands) until the start of the study.

Experimental Set-Up

The experimental setup is shown in Table 4. At t=0 mice were matched into experimental groups based on blood glucose (primary matching parameter) and body weight (secondary matching parameter). The control group received a lard based high fat diet (HFD 45 kcal % from lard; diet D12451 Research Diets, New Brunswick, USA) containing 23.7% w/w protein, 41.4% w/w carbohydrates and 23.6% w/w fat.

TABLE 4

Schematic overview of experimental set-up

| week of treatment | 0 | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|---|
| 1) HFD | x | | | | | | | | | | | | | | | | | | | | →  | x |
| 2) HFD + Nutramigen hydrolysate | x | | | | | | | | | | | | | | | | | | | | → | x |
| 3) HFD + Lipil | x | | | | | | | | | | | | | | | | | | | | → | x |
| 4) HFD + LGG (gavage) | x | | | | | | | | | | | | | | | | | | | | → | x |
| 5) HFD + Nutramigen hydrolysate + Lipil + LGG | x | | | | | | | | | | | | | | | | | | | | → | x |
| 6) HFD + peptide fraction Nutramigen | x | | | | | | | | | | | | | | | | | | | | → | x |
| Body weight and food intake | x | | x | | | x | | | x | | | x | | | x | | | x | | | | x |
| Matching on body weight | x | | | | | | | | | | | | | | | | | | | | | |
| Plasma cholesterol and triglycerides | x | | x | | | x | | | x | | | | | | x | | | | | | | x |
| Blood glucose and plasma insuline | x | | x | | | x | | | x | | | | | | x | | | | | | | x |
| Plasma ALAT (Alanine transaminase) analysis (pool) | x | | | | | | | | | x | | | | | | | | | | | | x |
| 48 h feaces collection | x | | | | | | | | | x | | | | | | | | | | | | x |
| Sacrifice | | | | | | | | | | | | | | | | | | | | | | x |

The diet specification are provided in Table 5 below.

TABLE 5

Rodent Diet with 45 kcal % Fat and Same with 208.5 gm Investigational Product, 0.079% gm DHA, EthylEster and 0.158R ARA, EthylEster

| | | Product # | |
|---|---|---|---|
| | Ingredient | D12451 Grams | D12050703 Grams |
| | Casein, 3D Mesh | 200 | 0 |
| | L-Cystine | 3 | 3 |
| | Investigational Product | 0 | 208.5 |
| | Corn Starch | 72.8 | 58.2 |
| | Maltodextrin 10 | 100 | 100 |
| | Sucrose | 172.8 | 172.8 |
| | Cellulose, BW200 | 50 | 50 |
| | DHA, EthylEster | 0 | 0.87 |
| | ARA, EthylEster | 0 | 0.35 |
| | Soybean Oil | 25 | 25 |
| | Lard | 177.5 | 175.64 |
| | Mineral Mix, S10026 | 10 | 10 |
| | DiCalcium Phosphate | 13 | 13 |
| | Calcium Carbonate | 5.5 | 5.5 |
| | Potassium Citrate, 1 H$_2$O | 16.5 | 16.5 |
| | Vitamin Mix V10001 | 10 | 10 |
| | Choline Bitartrate | 2 | 2 |
| | FD&C Yellow Dye #5 | 0 | 0 |
| | FD&C Red Dye #40 | 0.05 | 0 |
| | FD&C Blue Dye #1 | 0 | 0.05 |
| | TOTAL | 858.15 | 852.21 |
| Gram | Protein | 179 | 179 |
| Gram | Carbohydrate | 355.6 | 355.6 |
| Gram | Fat | 202.5 | 202.5 |
| Gram | Fiber | 50 | 50 |
| Kcal | Protein | 716 | 715.9 |
| Kcal | Carbohydrate | 1422.4 | 1422.4 |
| Kcal | Fat | 1822.5 | 1822.5 |
| | TOTAL | 3960.9 | 3961 |
| Kcal % | Protein | 18.1 | 18.1 |
| Kcal % | Carbohydrate | 35.9 | 35.9 |
| Kcal % | Fat | 46.0 | 46.0 |

The first treatment arm received HFD+Peptide component. All the casein from the HFD was replaced by Peptide component and carbohydrates were adjusted accordingly.

The second treatment arm received HFD+LCPUFA (0.079% w/w docosahexaenoic acid (DHA) and 0.158% w/w arachidonic acid (ARA). The lard concentration was slightly reduced (0.07% w/w) to compensate for the addition of the ARA/DHA.

The third treatment arm received HFD and was treated with *Lactobacillus rhamnosus* GG (LGG) by gavage three times per week (on Monday, Wednesday, and Friday).

The fourth arm (abbreviated in this report with 'NHLL') received HFD plus the combination treatment of Peptide component, DHA, ARA, and LGG. This arm served as reference to verify the effect found in Study 1 (included herein as Example 3). Again in this arm all the casein from the HFD was replaced with Peptide component, and carbohydrates were adjusted accordingly. LGG was provided by gavage. The lard concentration was slightly reduced (0.07% w/w) to compensate for the addition of the ARA/DHA.

The fifth treatment arm received HFD plus the greater than 500 Da fraction of the Peptide component. All casein from the HFD was replaced with this peptide fraction. All dietary compositions were adjusted to be isocaloric.

Measurements

Blood samples were takes in week 0, 3, 6, 9, 15 and 21 after 5 hours of fasting. Blood glucose was measured using hand-held glucometer immediately. Plasma cholesterol and plasma triglyceride levels were assayed immediately in fresh EDTA-plasma. The remainder of the plasma was stored at −80° C. for analysis of insulin and ALAT, and for possible other additional follow-up analysis. Faecal samples were collected over a 48 hour period at cage level in week 0, 9, and 21. Additionally, individual faecal samples were collected in week 21 to allow individual faecal analysis.

Total body fat and lean body mass were assessed non-invasively by EchoMRI in week 0, 9, 15, and 21. Mice were placed in a constraint tube which was then inserted into the EchoMRI for a period of approximately 30 seconds. During that time, total body fat and lean body mass were calculated and recorded and the mouse was removed from the apparatus.

The mice were sacrificed (un-fasted) in week 21. After sacrifice, the following samples were isolated:
  Serum Sample by heart puncture
  Heart including aortic root (for atherosclerosis analysis)
  Aortic arch (thoracic) in −80° C.
  Total liver weight, 2 pieces of sinister and caudate lobe in −80° C., medial lobe formalin
  Adipose tissue Sub cutaneous (inguinal): weight, right in −80° C., left in formalin Epididymal: weight, right in −80° C., left in formalin Visceral (omental): weight, part in −80° C., part in formalin Brown adipose tissue weight part in −80° C., part in formalin Pancreas in −80° C.

Spleen (in formalin)

Kidneys (right in −80° C., left in formalin)

Ileum (last 8 cm before caecum) in −80° C.

Colon (including faeces) in −80° C.

Eyes: left in Davidson formalin, right in −80° C.

Brain (right in −80° C., left in 4% paraformaldehyde

Blood glucose was measured immediately using a hand-held glucometer. Total plasma cholesterol and triglyceride levels were measured using kits No. 11489437 and 11488872 (Roche Diagnostics, Almere, The Netherlands), respectively. The plasma levels of insulin (Ultrasensitive mouse insulin ELISA, Merdocia, Uppsala, Sweden) were determined by ELISA.

Body Weight Results

Figure 1B:
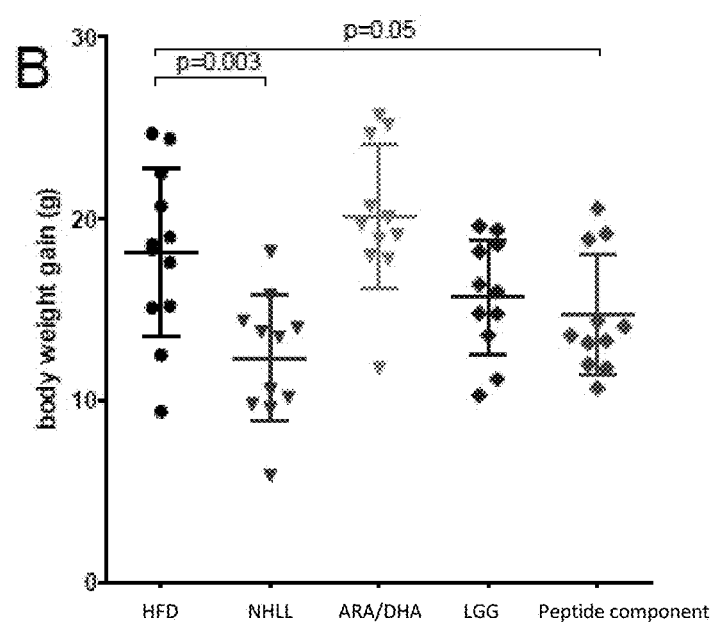
FIG. 1B illustrates weight gain after 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.

Twenty-one weeks of HFD feeding resulted in an average body weight of 48.2±6.3 g, which is a body weight gain of approximately 18 g relative to the start (t=0). For reference, chow control mice gain approximately 10 g. Body weight in the NHLL group (42.1±4.8 g) was significantly lower compared to HFD. NHLL-treated mice gained approximately 12 g relative to t=0. Body weight of the LCPUFA group (50.2±5.4 g) was comparable to HFD. Body weight from the LGG group (45.8±5.3 g) was slightly, but not significantly lower compared to HFD. Body weight of the Peptide component group (44.3±5.0 g) was almost comparable to NHLL, although not reaching statistical significance relative to HFD, while body weight gain (14.7±3.3 g) was borderline significantly lower compared to HFD (P=0.05). See FIGS. 1A and 1B.

Figure 1C:
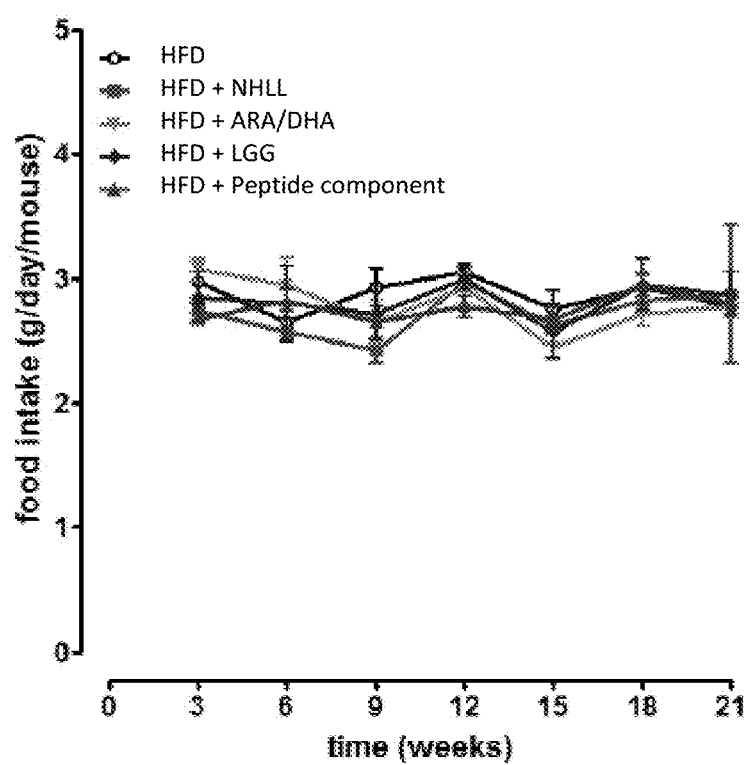
FIG. 1C illustrates food intake per gram per day per mouse for mice fed a high fat diet (HFD) (control group), mice fed a HFD supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.

Food intake was comparable between all groups and comparable over time. The highest average food intake was 2.9±0.2 g/mouse/day for the HFD group and the lowest average food intake was 2.7±0.2 g/mouse/day for the HFD+Peptide component group. (See FIG. 1C)

Blood Glucose, Plasma Insulin and HOMA-IR Results

Figures 2A, 2B:
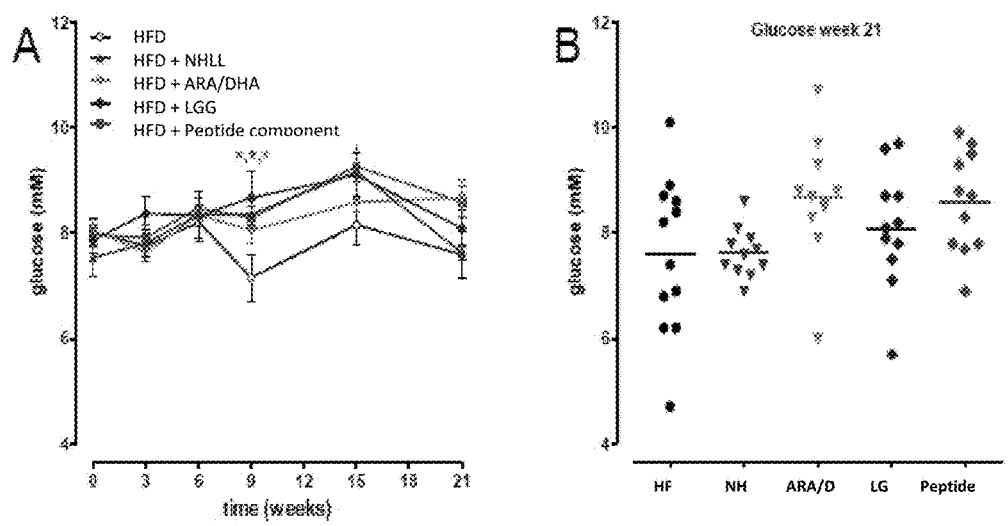
FIG. 2A illustrates fasting blood glucose over 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD supplemented with a peptide component only.
FIG. 2B illustrates fasting blood glucose after 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.

Blood glucose remained relatively stable in the HFD group throughout the entire study period (on average 7.8 mM), although the level at t=9 weeks was slightly lower compared to the other time points. This temporary drop in glucose as absent in the other groups and resulted in significant differences between HFD control and the HFD+NHLL, HFD+LGG, and HFD+Peptide groups. (See FIGS. 2A and 2B).

Figures 2C, 2D:
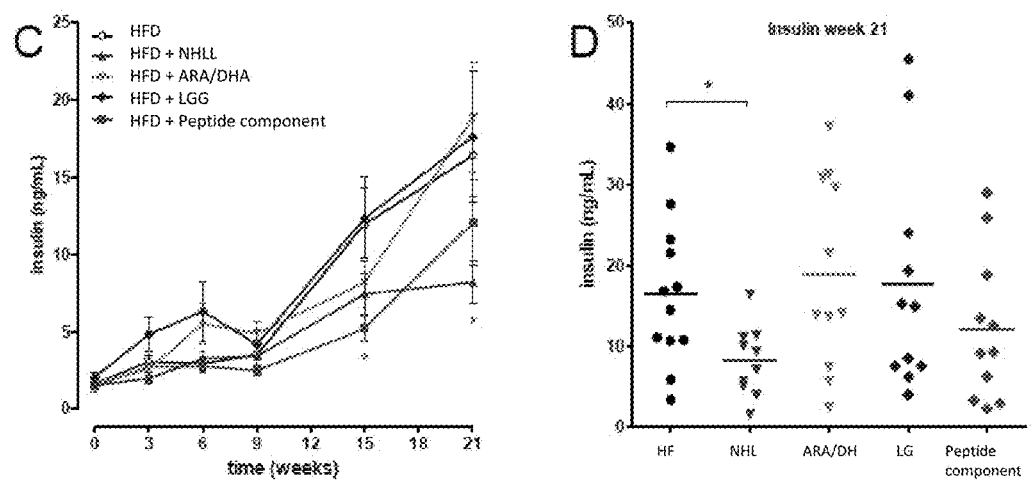
FIG. 2C illustrates fasting plasma insulin over 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.
FIG. 2D illustrates fasting plasma insulin after 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.

Fasting plasma insulin levels increased modestly (until week 9) and then strongly and gradually over time in the HFD control group reaching 16.4±9.1 ng/mL in week 21. See FIGS. 2C and 2D. The increase in insulin levels in the NHLL group was slower and in week 21 (8.2±4.3 ng/mL) the levels were significantly lower compared to HFD control. See FIGS. 2C and 2D. With respect to the separate components, the Peptide component group also showed lower insulin levels compared to HFD in week 15, but the insulin-lowering effect in week 21 did not reach significance. Insulin levels in the HFD+LCPUFA and in the HFD+LGG group were comparable to the HFD control group.

Figure 2E:
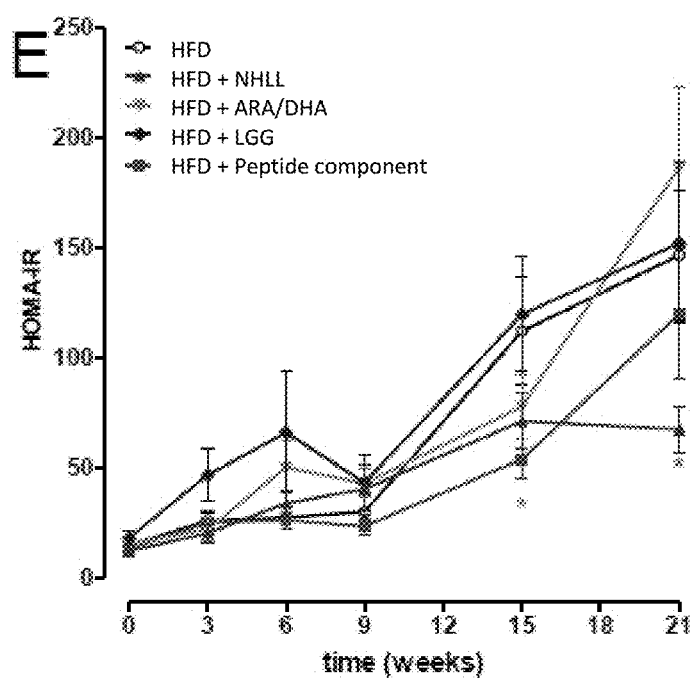
FIG. 2E illustrates HOMA-IR over 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.

HOMA-IR (FIG. 2E), which is a measure of insulin resistance and calculated from fasting glucose and fasting insulin, shows a very similar patter as the insulin levels. This suggests that the NHLL group and the Peptide component group were less insulin resistant than the HFD control group. Thus, the combination of individual components (represented by the NHLL group) resulted in the most pronounced effects on fasting insulin and HOMA-IR. This effect is homogenous and characterized by a small inter-individual variation among animals. Furthermore, the effect cannot be attributed to a specific component of NHLL and thus seems to be the net effect of the combination of components.

Plasma Cholesterol and Triglycerides

Plasma cholesterol increase gradually over time in the HFD group (See FIG. 3A) reaching 24.3±13.7 mM in week 21. See FIG. 3B. The NHLL group showed remarkably lower levels of plasma cholesterol compared to HFD control and remained almost at baseline levels throughout the study and comparable to plasma values in chow fed mice (not included in current study). In week 21, cholesterol levels of the NHLL group were 11.1±3.3 mM. Plasma cholesterol levels in Peptide component group were comparable to the NHLL group and also remained low throughout the study, with average levels of 11.9±3.1 mM in week 21. The other two components of NHLL, LCPUFA and LGG, had no significant effects on plasma cholesterol and were comparable to HFD.

Plasma triglycerides also gradually increased over time in the HFD control group (FIG. 3C) to 3.5±3.0 mM in week 21. See. FIG. 3D. The plasma triglyceride levels in the NHLL group remained at baseline levels during the total study with significantly lower levels form week 9 until week 21 (1.1±0.6 mM). For comparison, triglycerides in chow mice typically slightly increase over time to approximately 2.5 mM. The levels in the Peptide component group also remained at baseline levels and were significantly lower at all time points analysed (1.5±1.0 mM in week 21) when compared with the HFD control. LCPUFA feeding had no effects on plasma triglycerides and plasma concentrations were comparable to HFD. Triglyceride levels in the LGG group were slightly, but not significantly lower compared with HFD control, reaching 2.0±1.0 mM at week 21.

Together, NHLL treated mice showed very low total cholesterol and plasma triglyceride levels despite relatively high HFD consumption suggesting that either intestinal food uptake is reduced or more energy (lipids) is absorbed by the metabolically active organs and utilized. These effects seem to be mainly driven by the Peptide component in NHLL.

Liver Function Market ALAT

ALAT levels were measured at baseline, week 9 and week 21 in pooled plasma. Baseline levels were low (11 U/L). Upon HFD feeding, ALAT levels increased to 58 U/L in week 9 and further increased to 187 U/L in week 21 in the HFD group. For comparison, ALAT levels in chow fed mice reached levels of approximately 52 U/L in week 21 (data from other study). The NHLL group showed only a moderate increase in ALAT (45 U/L in week 9 and 54 U/L in week 21). ALAT levels of the Peptide component group were very comparable to NHLL (45 U/L in week 9 and 67 U/L in week 21). LCPUFA treatment transiently increased ALAT to 106 U/L in week 9 followed by a slight decrease reaching 81 U/L in week 21, which is substantially lower when compared with HFD control. Also ALAT level in LGG treated mice were lower compared to HFD (66 U/L in week 9 and 124 U/L in week 21).

Body Composition Analysis

Figures 4A, 4B:
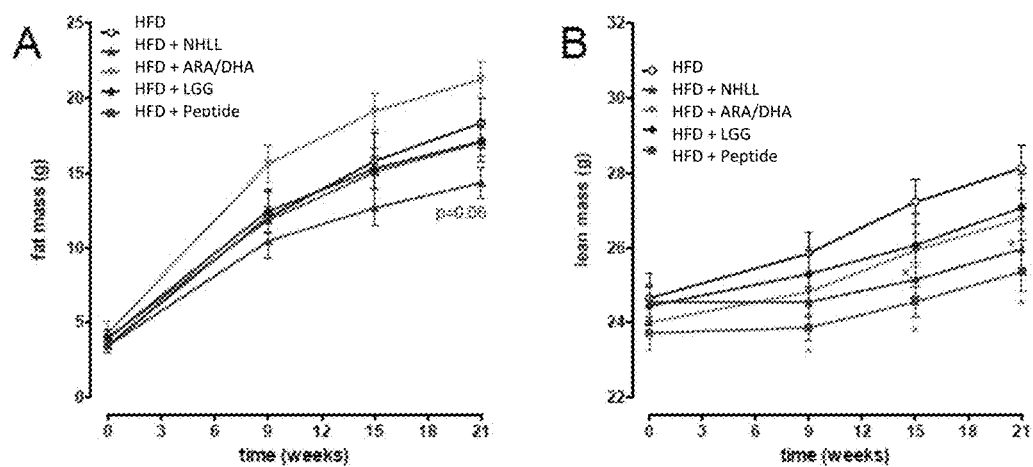
FIG. 4A illustrates total body fat over 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.
FIG. 4B illustrates lean body mass over 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.

Body composition was analysed non-invasively using the EchoMRI. The HFD fed control mice showed a clear increase in total body fat from 3.5±1.7 g at t=0 to 18.4±5.7 g in week 21. See FIG. 4A. Absolute total body fat values tended to be lower in the NHLL group in week 21 (14.4±3.4 g). The increase (expressed as delta change) in total body fat was significantly less in the NHLL group compared to HFD control. Total body fat in the LCPUFA group was slightly but not significantly higher than HFD and also the delta increase in total body fat was not significantly different. No effects on total body fat were observed with LGG and Peptide component.

Lean mass slightly increased during HFD feeding in the HFD group (delta: 3.5±1.1 g) (See FIG. 4B), with the strongest increase from week 9 onwards. This increase in lean mass was less pronounced for all treatment groups and significantly lower in case of the NHLL and the Peptide component groups.

Tissue Weights at Sacrifice

Figure 5A:
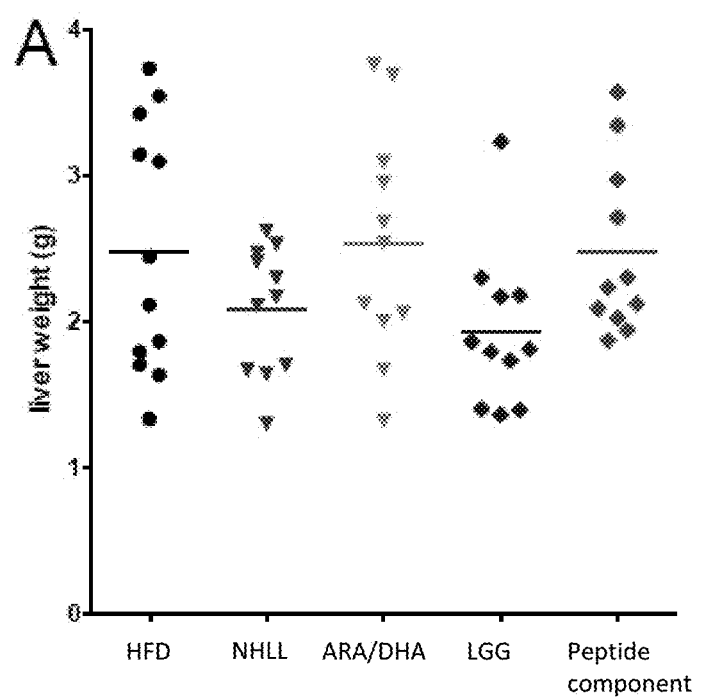
FIG. 5A illustrates tissue weights of the livers at sacrifice after 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.
Figure 5B:
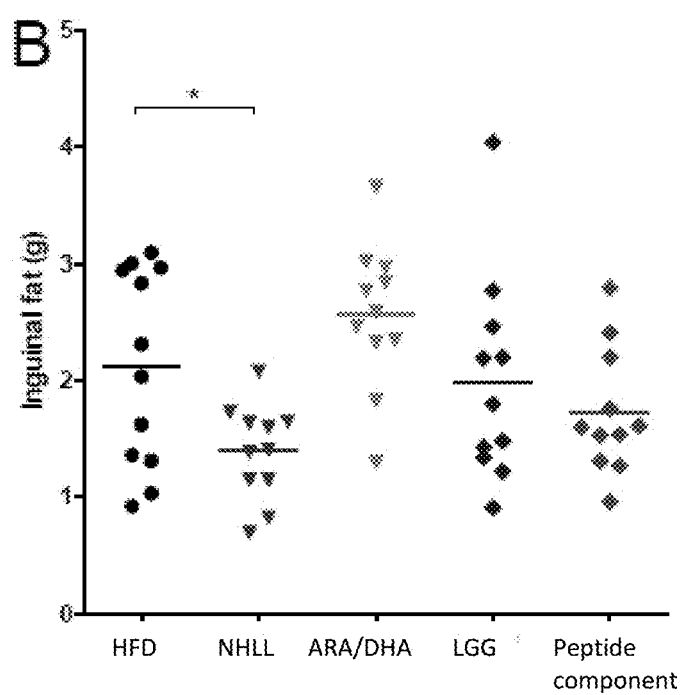
FIG. 5B illustrates tissue weights of inguinal fat at sacrifice after 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.
Figure 5C:
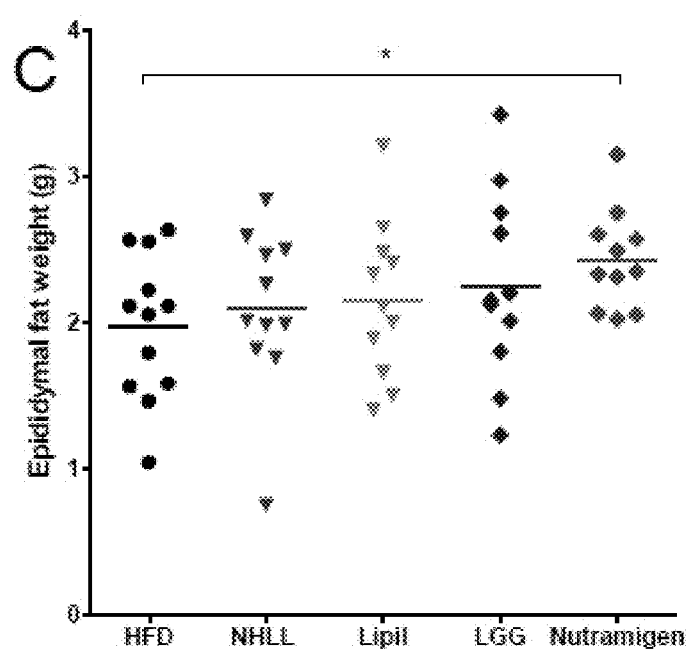
FIG. 5C illustrates tissue weight of the epididymal fat at sacrifice after 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.
Figure 5D:
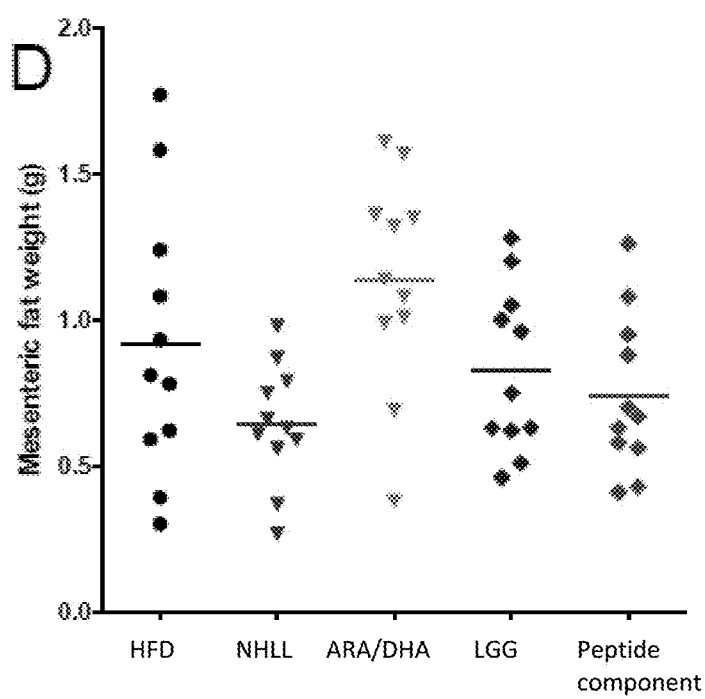
FIG. 5D illustrates tissue weight of the mesenteric fat at sacrifice after 21 weeks for mice fed a high fat diet (HFD) (control group), mice fed a HFD and supplemented with a peptide component, LGG, ARA and DHA (NHLL), mice fed a HFD and supplemented with ARA and DHA only, mice fed a HFD and supplemented with LGG only, and mice fed a HFD and supplemented with a peptide component only.

After 21 weeks of dietary treatment, the mice were sacrificed. Tissues were isolated and weighed. See FIGS. 5A-5D. Liver weight of the NHLL and LGG groups tended to be lower compared to the HFD and both treatments diminished the variation between mice. By contrast, LCPUFA and Peptide component had no effects on liver weight (See FIG. 5A) and showed a similar variation as HFD control group.

Three adipose tissue depots were collected and weighed. The inguinal fat depot was significantly lower in the NHLL group compared to HFD and tended to be lower in the Peptide component group. A similar pattern was observed for the mesenteric fat depot (yet no significance for NHLL and Nutramigen hydrolysate). The epididymal fat depot mass was significantly higher in the Peptide component group suggesting that preferred storage of fat in this depot may underlie the effects seen in the other depots. Adipose tissue weights in the LCPUFA and in the LGG groups were comparable to HFD. Since NHLL group did not show a redistribution of fat (no increase of epididymal fat mass), it is unclear how the animals handle the energy consumed and the data suggest that combination treatment (Peptide component, LCPUFA and LGG) allows to adjust overall metabolism/energy handling in a way that cannot be achieved with a single component. See FIGS. 5B, 5C, and 5D.

Example 2

Example 2 describes the experimental procedures for evaluating metabolic, and cardiovascular risk factors in LDLr knockout mice fed a HFD supplemented with a >500 Da peptide fraction of the Peptide component. The same experimental procedures and methodologies as employed in Example 1 were used in Example 2.

Body Weight and Food Intake

Figure 6A:
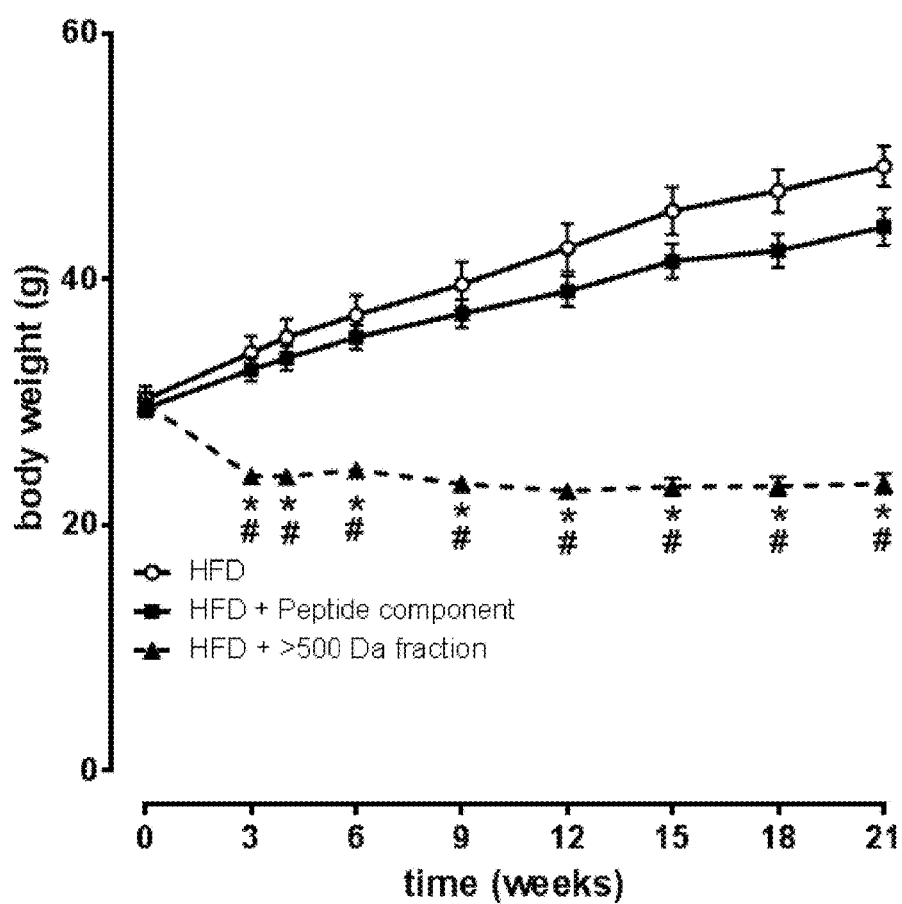
FIG. 6A illustrates body weight over 21 weeks for mice fed a high fat diet (HFD) (control group), mice fed a HFD and supplemented with a peptide component, and mice fed a HFD and supplemented with a >500 Da fraction of the peptide component.
Figure 6B:
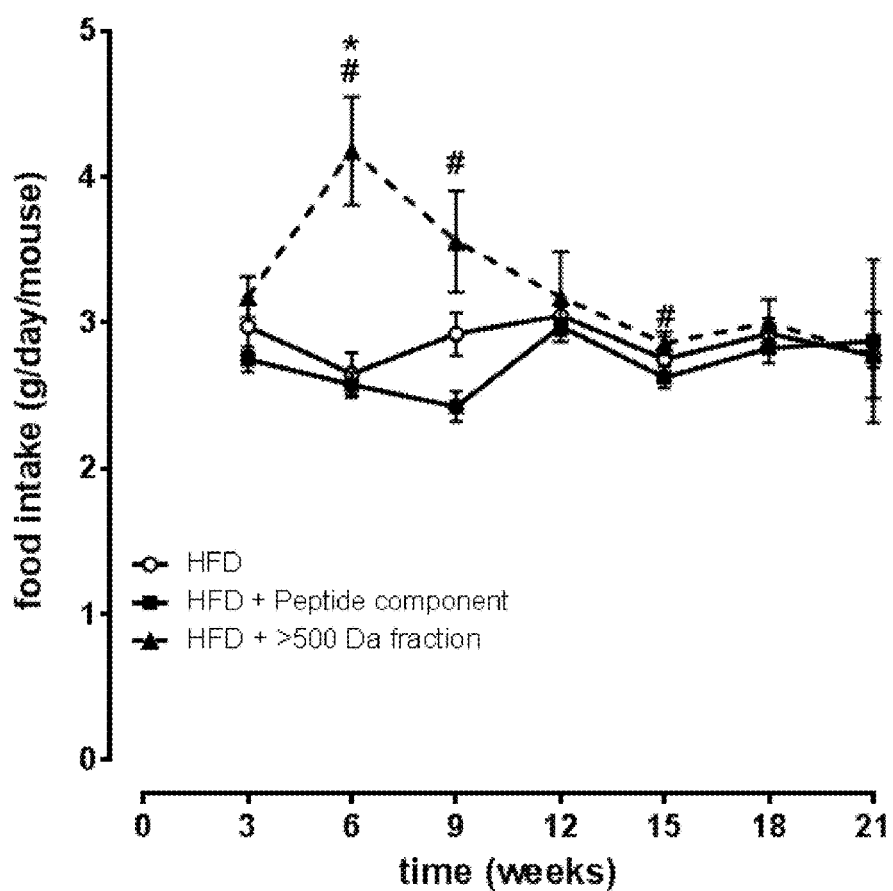
FIG. 6B illustrates weight gain after 21 weeks for mice fed a high fat diet (HFD) (control group), mice fed a HFD and supplemented with a peptide component, and mice fed a HFD and supplemented with a >500 Da fraction of the peptide component.

Body weight in the peptide fraction group showed an initial drop in body weight at t=3 weeks (FIG. 6A). After this adaptation, body weight remained stable until the end of the study. At all time points, body weight was significantly lower compared to HFD. Except for increased food intake at t=6 weeks (FIG. 6B), there was no difference in food intake between the Peptide group and the HFD control group. When compared to the Peptide component group, food intake in the >500 Da Peptide fraction group was higher at t=6, 9 and 15 weeks. These data suggest that the mice needed to adapt to the new diet during the first weeks and subsequently reached a steady state in which body weight and food intake remained stable.

Blood Glucose and Plasma Insulin

Figure 7A:
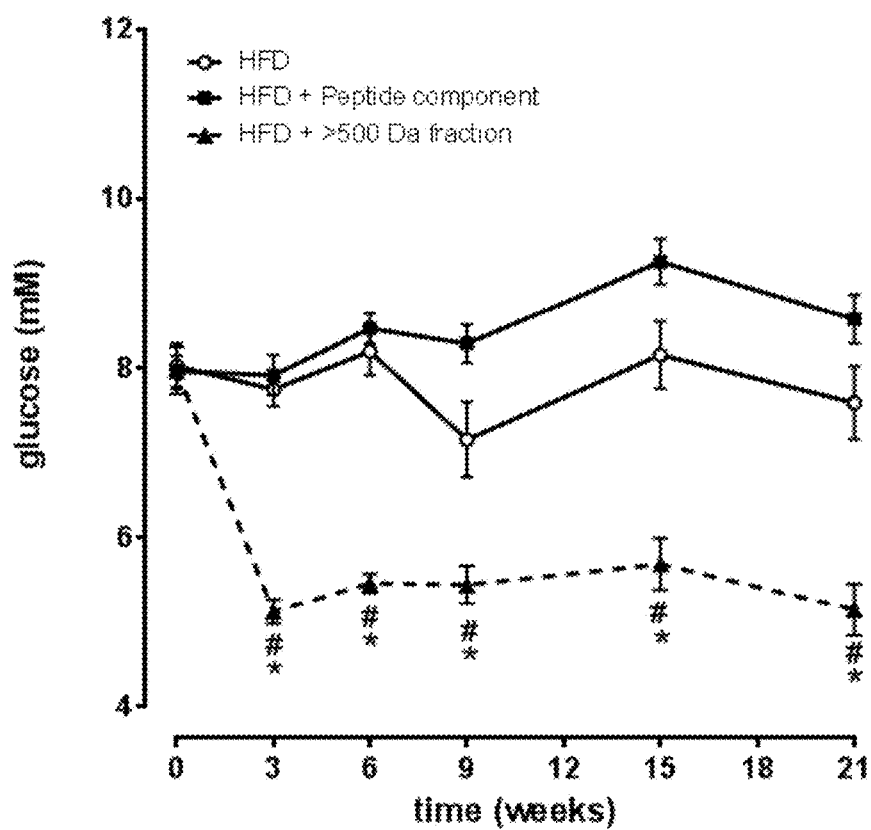
FIG. 7A illustrates fasting blood glucose over 21 weeks for mice fed a high fat diet (HFD) (control group), mice fed a HFD and supplemented with a peptide component, and mice fed a HFD and supplemented with a >500 Da fraction of the peptide component.

Fasting blood glucose levels in the >500 Da peptide fraction group dropped from baseline levels of 8.0±0.9 mM to 5.1±0.5 mM (within normal range of fasting glucose) and remained low and stable until the end of the study (FIG. 7A). All time points were significantly lower compared to HFD and also when compared to Peptide component.

Figure 7B:
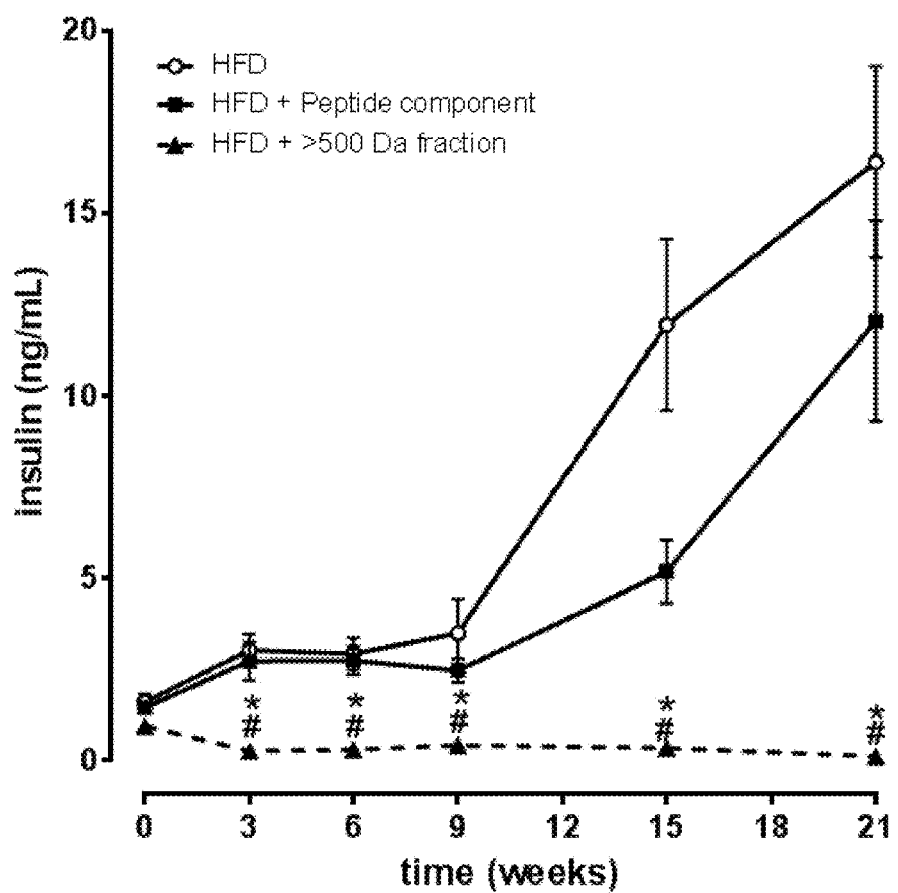
FIG. 7B illustrates fasting plasma insulin over 21 weeks for mice fed a high fat diet (HFD) (control group), mice fed a HFD and supplemented with peptide component, and mice fed a HFD and supplemented with a >500 Da fraction of the peptide component.

Also, fasting insulin levels decreased when fed the >500 Da peptide fraction diet (0.3±0.4 ng/ml in week 3) and remained low during the entire study. The insulin-lowering effect was very pronounced and significant compared with HFD and Peptide component at all time points (FIG. 7B). These low levels of insulin suggest high insulin sensitivity. These levels are comparable to a healthy chow fed mouse.

Plasma Cholesterol and Triglycerides

Figure 8A:
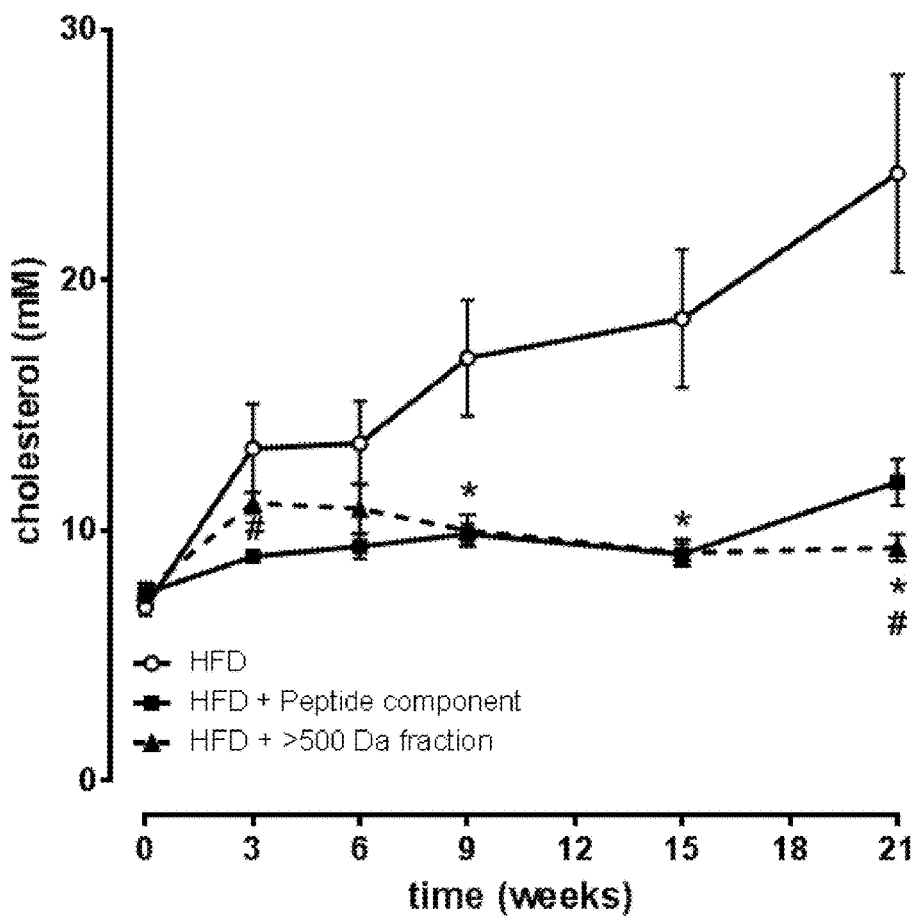
FIG. 8A illustrates fasting plasma cholesterol over 21 weeks for mice fed a high fat diet (HFD) (control group), mice fed a HFD and supplemented with a peptide component, and mice fed a HFD and supplemented with a >500 Da fraction of the peptide component.
Figure 8B:
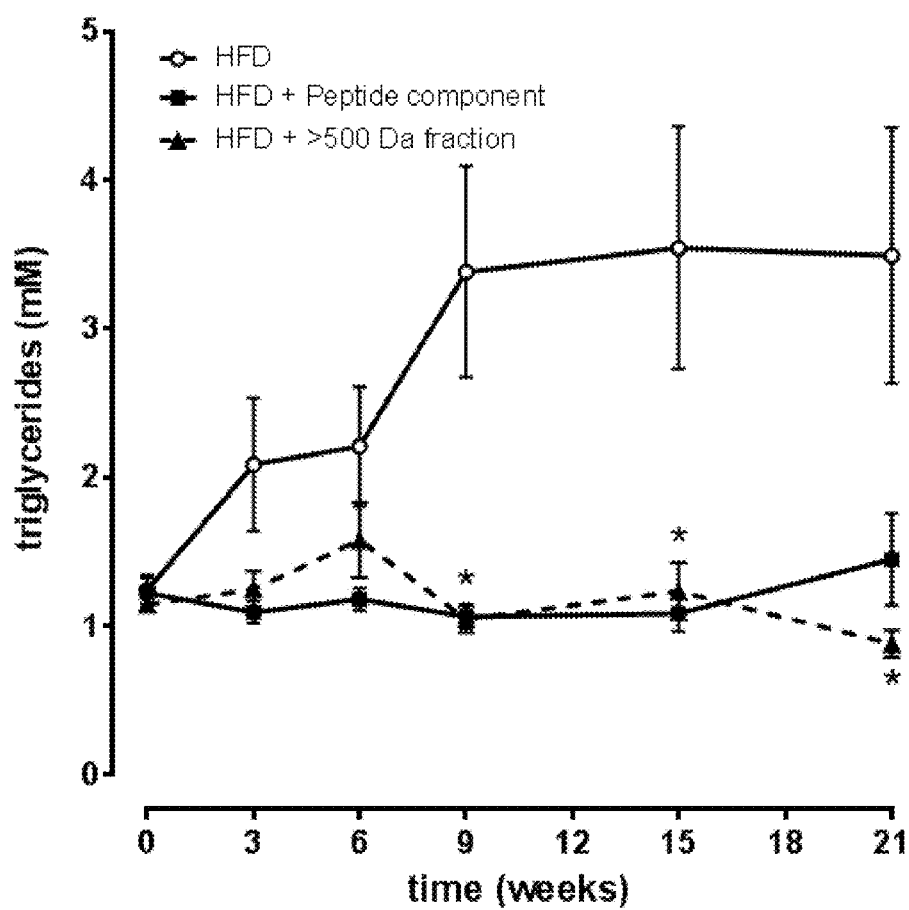
FIG. 8B illustrates fasting plasma triglycerides over 21 weeks for mice fed a high fat diet (HFD) (control group), mice fed a HFD and supplemented with a peptide component, and mice fed a HFD and supplemented with a >500 Da fraction of the peptide component.

Plasma cholesterol levels in the >500 Da peptide fraction group showed a slight transient increase in week 3 followed by a decrease (FIG. 8A). From week 9 onward, plasma cholesterol levels were significantly lower compared to HFD. Plasma triglycerides remained relatively stable in the peptide fraction group and not different compared to Peptide component (FIG. 8B). From week 9 onward, plasma triglyceride levels were significantly lower compared to HFD.

Body Composition Analysis

Figure 9A:
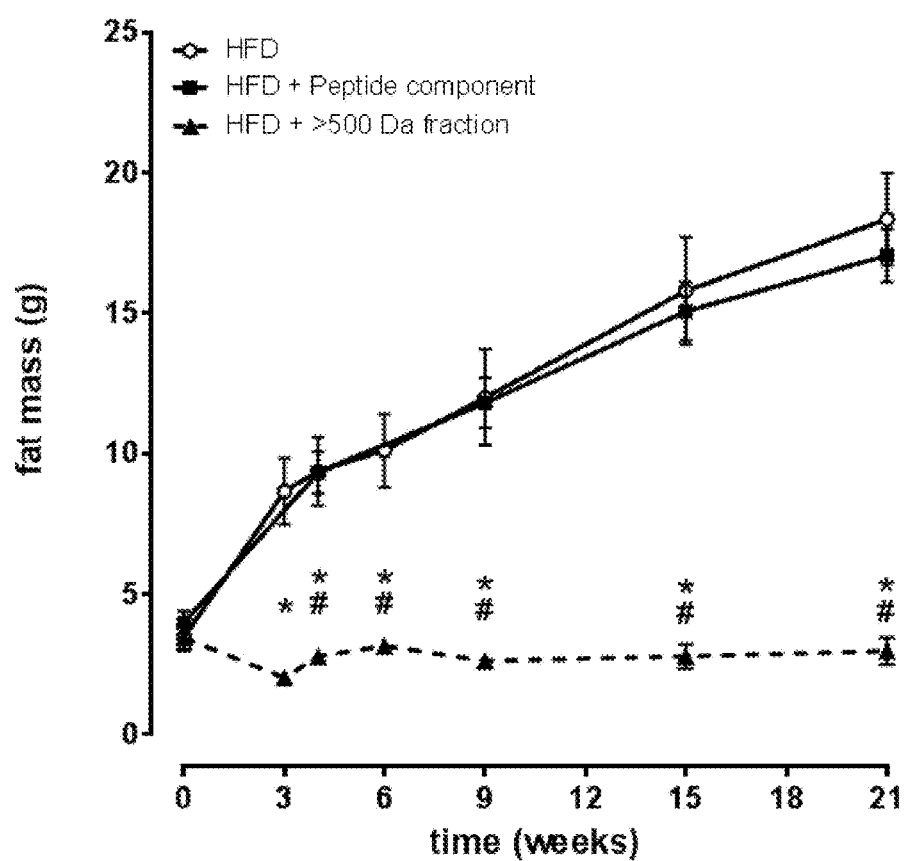
FIG. 9A illustrates total body fat over 21 weeks for mice fed a high fat diet (HFD) (control group), mice fed a HFD and supplemented with a peptide component, and mice fed a HFD and supplemented with a >500 Da fraction of the peptide component.
Figure 9B:
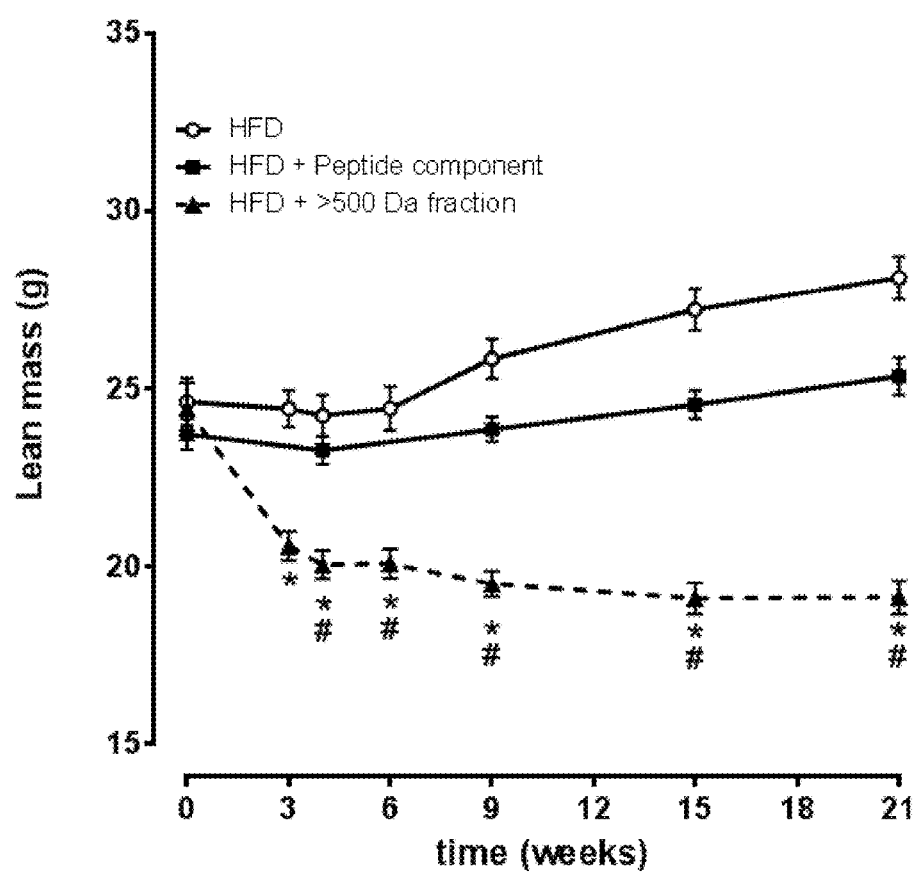
FIG. 9B illustrates lean body mass over 21 weeks for mice fed a high fat diet (HFD) (control group), mice fed a HFD and supplemented with a peptide component, and mice fed a HFD and supplemented with a >500 Da fraction of the peptide component.
Figure 10A:
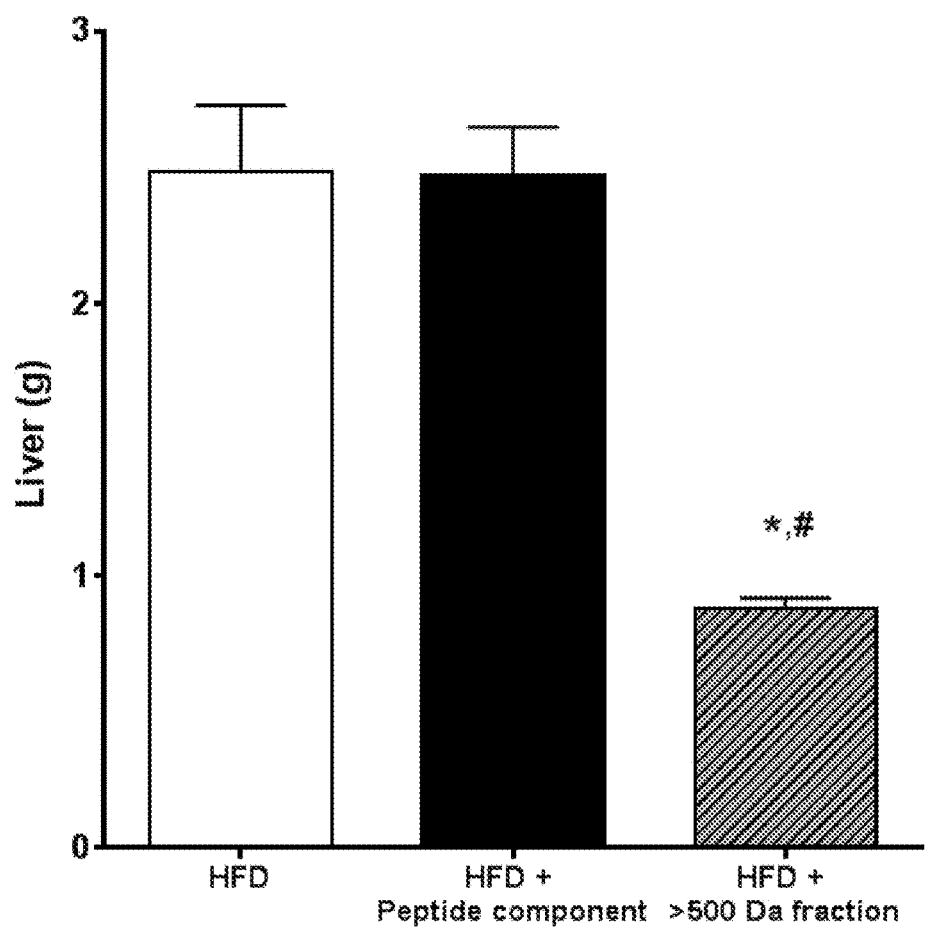
FIG. 10A illustrates tissue weights of the liver at sacrifice (t=week 21) after 21 weeks for mice fed a high fat diet (HFD) (control group), mice fed a HFD and supplemented with a peptide component, and mice fed a HFD and supplemented with a >500 Da fraction of the peptide component.
Figure 10B:
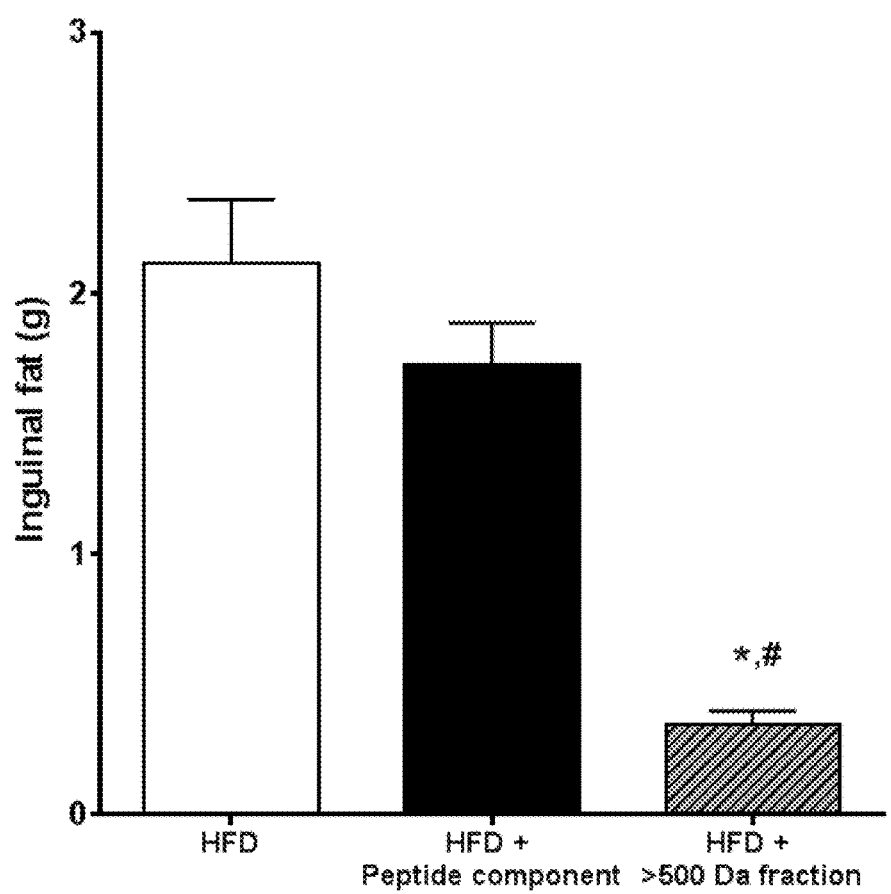
FIG. 10B illustrates tissue weights of inguinal fat at sacrifice (t=week 21) after 21 weeks for mice fed a high fat diet (HFD) (control group), mice fed a HFD and supplemented with a peptide component, and mice fed a HFD and supplemented with a >500 Da fraction of the peptide component.
Figure 10:
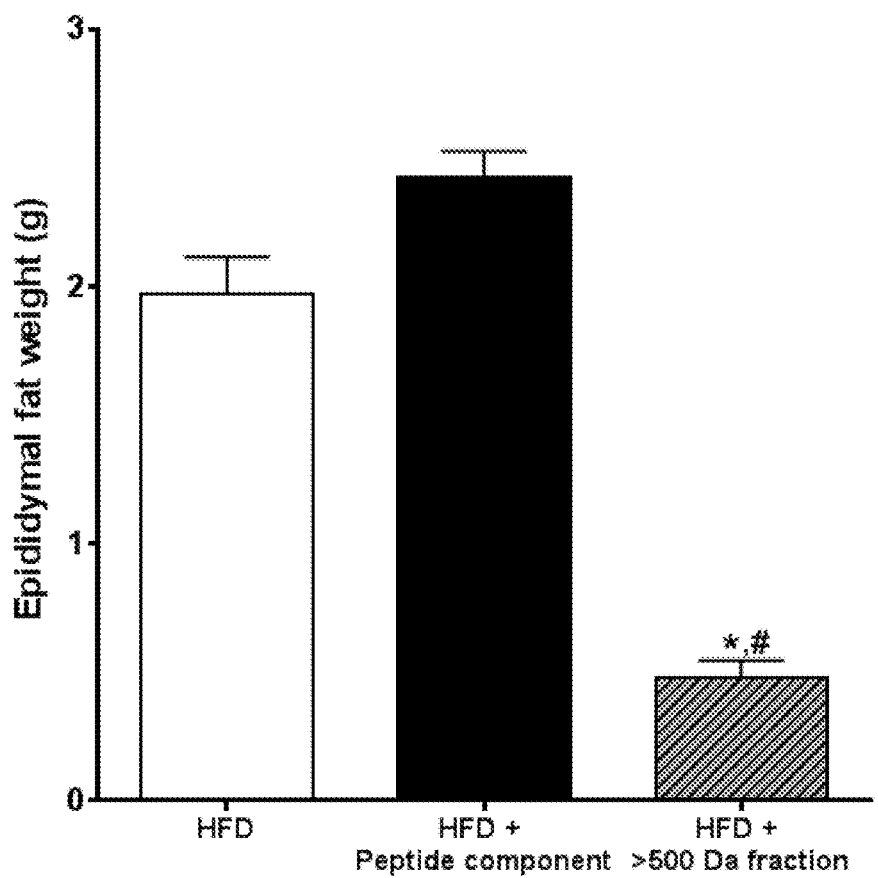
FIG. 10C illustrates tissue weights of epididymal fat at sacrifice (t=week 21) after 21 weeks for mice fed a high fat diet (HFD) (control group), mice fed a HFD and supplemented with a peptide component, and mice fed a HFD and supplemented with a >500 Da fraction of the peptide component.
FIG. 10D illustrates tissue weights of mesenteric fat at sacrifice (t=week 21) after 21 weeks for mice fed a high fat diet (HFD) (control group), mice fed a HFD and supplemented with a peptide component, and mice fed a HFD and supplemented with a >500 Da fraction of the peptide component.
Figure 10D:
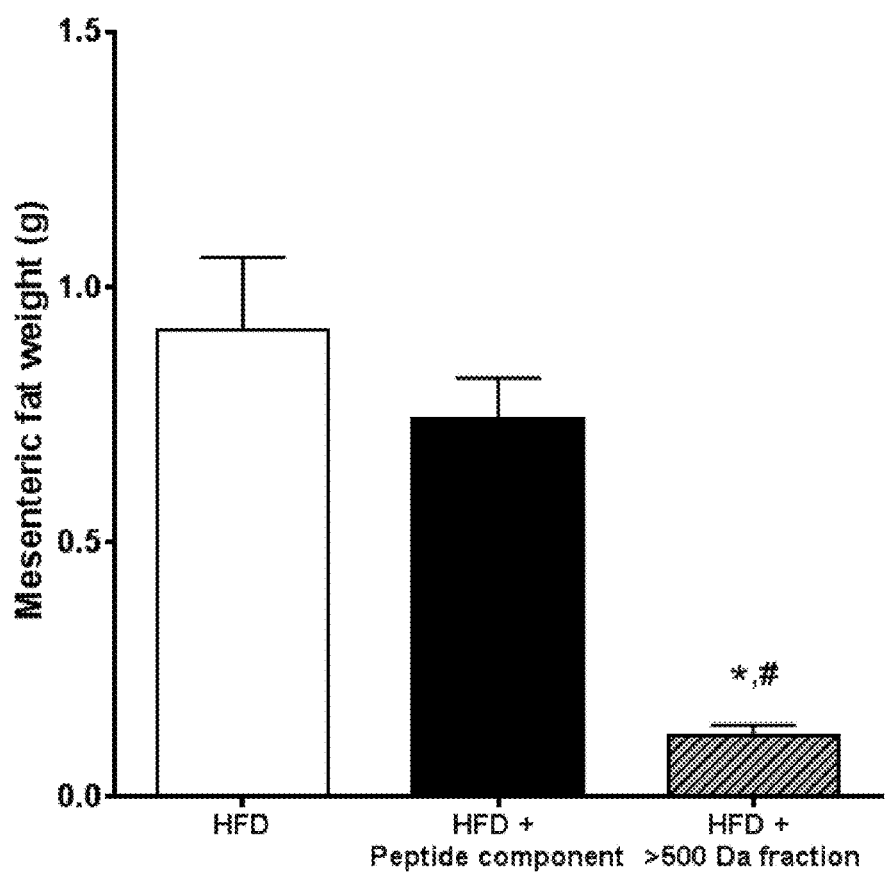

Due to the initial drop in body weight, it was decided to add additional EchoMRI measurements to more closely monitor the mice. Body fat slightly decreased compared to baseline (−1.0±1.8 g), while the HFD and Peptide component groups clearly and substantially gained total body fat. Body fat values were significantly lower in the >500 Da peptide fraction group compared to the other groups, at all time points analyzed. Of note, the initial drop in body weight observed in the >500 Da peptide fraction-treated group can mainly be attributed to a loss of lean mass (−3.9±1.2 g). Lean mass decreased slightly further and reached 19.1±1.5 g at the end of the study, which is loss of 5.6±2.6 g compared to baseline. Lean mass values were significantly lower compared to the HFD and Peptide component groups. (FIGS. 9A and 9B).

Liver Function Marker ALAT

ALAT levels were measured in pooled plasma. Levels remained low throughout the study (37 U/L in week 9 and 30 U/L in week 21), and ALAT levels were thus markedly lower than in HFD control (58 U/L in week 9 and 187 U/L in week 21) and slightly lower than in the Peptide component group (45 U/L in week 9 and 67 U/L in week 21).

Tissue Weights at Sacrifice

After 21 weeks of dietary treatment, the mice were sacrificed. Tissues were isolated and weighed (FIGS. 10A, 10B, 10C and 10D). In line with the low body weight levels, all organs (liver, inguinal, epididymal and mesenteric fat) weighed markedly and significantly less in the >500 Da peptide fraction group as compared with the HFD and peptide component groups. These data are comparable to a lean chow fed mouse.

Example 3

Sixty-four male LDLr−/− mice obtained from the breeding facility at TNO were used. Animals were housed in macrolon cages (3-5 mice per cage) during the experiment at TNO Gabius Building Leiden in clean conventional animal rooms (relative humidity 50-60%, temperature ~21° C., light cycle 7 am to 7 μm). Mice were supplied with food and acidified tap water ad lib. Mice were fed standard lab chow (Ssniff R/M diet V1530, Uden, The Netherlands), until the start of the study.

Experimental Set-Up

At t=0 mice were matched into experimental groups based on blood glucose (primary matching parameter) and body weight (secondary matching parameter). Table 6 shows the schematic overview of the experimental set-up.

TABLE 6

Schematic overview of experimental set-up.

| week of treatment | 0 | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|---|
| 1) HFD | x | - | - | - | - | - | - | - | - | - | - | - | - | - | - | - | - | - | - | - | → | x |
| 2) HFD + Nutramigen hydrolysate | x | | | | | | | | | | | | | | | | | | | | → | x |
| 3) HFD + Lipil | x | - | - | - | - | - | - | - | - | - | - | - | - | - | - | - | - | - | - | - | → | x |
| 4) HFD + LGG (gavage) | x | - | - | - | - | - | - | - | - | - | - | - | - | - | - | - | - | - | - | - | → | x |
| 5) HFD + Nutramigen hydrolysate + Lipil + LGG | x | - | - | - | - | - | - | - | - | - | - | - | - | - | - | - | - | - | - | - | → | x |
| 6) HFD + peptide fraction Nutramigen | x | - | - | - | - | - | - | - | - | - | - | - | - | - | - | - | - | - | - | - | → | x |
| Body weight and food intake | x | | x | | | x | | | x | | | x | | | x | | | x | | | | x |
| Matching on body weight | x | | | | | | | | | | | | | | | | | | | | | |
| Plasma cholesterol and triglycerides | x | | x | | | x | | | x | | | | | | x | | | | | | | x |
| Blood glucose and plasma insulin | x | | x | | | x | | | x | | | | | | x | | | | | | | x |
| Plasma ALAT (Alanine transaminase) analysis (pool) | x | | | | | | | | x | | | | | | | | | | | | | x |
| 48 h faeces collection | x | | | | | | | | x | | | | | | | | | | | | | x |
| Sacrifice | | | | | | | | | | | | | | | | | | | | | | x |

One control group was fed a low fat control diet (LFD; diet 12450B, research Diets, New Brunswick, USA) containing 19.2% w/w protein, 67.3% w/w carbohydrates and 4.3% w/w fat. The other control group was fed a lard based high fat diet (HFD; diet D12451 Research Diets, New Brunswick, USA) containing 23.7% w/w protein, 41.4% w/w carbohydrates and 23.6% w/w fat. The third group was fed a HFD based diet containing the proprietary products Peptide component, LCPUFA (Docosahexaenoic acid, (DHA) and arachidonic acid (ARA)) and mice received oral gavage Lactobacillus rhamnosus GG (LGG). This group is abbreviated by NHLL. All the casein from HFD was replaced with Peptide component (batch code 0019072), as well as the representative part of carbohydrates. Furthermore, 0.079% w/w DHA and 0.158% w/w ARA were added to the diet in the form of LCPUFA formulation (Batch code 0033636). The composition of the diets is shown in Table 7. Mice were treated with LGG ($1 \times 10^9$ CFU (Batch FR010587) in 200 µL PBS) by oral gavage three times per week (on Monday, Wednesday and Friday). A gavage control group (HFD_PBS gavage) was included to control for the effect of gavage treatment. These mice were fed HFD and treated with PGS gavage (200 µL) three times per week (on Monday, Wednesday and Friday).

TABLE 7

Diet Specifications

| | | Product # | |
|---|---|---|---|
| Ingredient | | D12451 Grams | D12050703 Grams |
| Casein, 3D Mesh | | 200 | 0 |
| L-Cystine | | 3 | 3 |
| Investigational Product | | 0 | 208.5 |
| Corn Starch | | 72.8 | 58.2 |
| Maltodextrin 10 | | 100 | 100 |
| Sucrose | | 172.8 | 172.8 |
| Cellulose, BW200 | | 50 | 50 |
| DHA, EthylEster | | 0 | 0.87 |
| ARA, EthylEster | | 0 | 0.35 |
| Soybean Oil | | 25 | 25 |
| Lard | | 177.5 | 175.64 |
| Mineral Mix, S10026 | | 10 | 10 |
| DiCalcium Phosphate | | 13 | 13 |
| Calcium Carbonate | | 5.5 | 5.5 |
| Potassium Citrate, 1 $H_2O$ | | 16.5 | 16.5 |
| Vitamin Mix V10001 | | 10 | 10 |

TABLE 7-continued

Diet Specifications

| | | Product # | |
|---|---|---|---|
| Ingredient | | D12451 Grams | D12050703 Grams |
| Choline Bitartrate | | 2 | 2 |
| FD&C Yellow Dye #5 | | 0 | 0 |
| FD&C Red Dye #40 | | 0.05 | 0 |
| FD&C Blue Dye #1 | | 0 | 0.05 |
| | TOTAL | 858.15 | 852.21 |
| Gram | Protein | 179 | 179 |
| Gram | Carbohydrate | 355.6 | 355.6 |
| Gram | Fat | 202.5 | 202.5 |
| Gram | Fiber | 50 | 50 |
| Kcal | Protein | 716 | 715.9 |
| Kcal | Carbohydrate | 1422.4 | 1422.4 |
| Kcal | Fat | 1822.5 | 1822.5 |
| | TOTAL | 3960.9 | 3961 |
| Kcal % | Protein | 18.1 | 18.1 |
| Kcal % | Carbohydrate | 35.9 | 35.9 |
| Kcal % | Fat | 46.0 | 46.0 |

Measurements

Body weight (individually) and food intake (at cage level) were monitored over time and blood samples were taken in week 0, 3, 6, 9, 12, 15, 18, and 21 after 5 h fasting. Blood glucose was measured immediately using a hand-held glucometer. The remainder of the plasma was stored at −80° C. for further analysis. Spot urine and faecal samples were obtained in week 0, 9, 15, and 21 and stored at −80° C.

After 21 weeks on the diets, total body fat and lean body mass were assessed non-invasively by EchoMRI. Mice were placed in a constraint tube which was then inserted in the Echo MRI for a period of approximately 30 s. During that time, total body fat and lean body mass were calculated and recorded and the mouse was removed from the apparatus.

The mice were sacrificed (un-fasted) in week 21. After sacrifice, the following samples were isolated for future analysis:

Serum sample by heart puncture

Heart including aortic root for atherosclerosis analysis

Aortic arch (snap freezing)

Total liver weight (one part snap froze, one part formalin fixed)

Adipose tissue (inguinal, omental and epididymal) weight (one part of each depot snap froze, one part of each depot formalin fixed)

Pancreas (snap frozen)

Kidneys (one kidney snap frozen, one kidney formalin fixed)

Colon (snap frozen)

Muscle (snap frozen)

Brain (one part fixed in 4% paraformaldehyde, one part snap frozen)

Blood and Urine Sample Analysis

Blood glucose was measured immediately using handheld glucometer. Total plasma cholesterol and triglyceride levels were measured using kits No. 11489437 and 11488872 (Roche Diagnostics, Almere, The Netherlands), respectively. The plasma levels of insulin (Ultrasensitive mouse insulin ELISA, Mercodia, Uppsala, Sweden), soluble vascular cell adhesion molecule 1 (sVCAM-1; R&D Systems), leptin (R&D Systems), adiponectin (R&D Systems) and Serum Amyloid A (SAA; Biosource) were determined by ELISA.

Metabolic hormone concentrations were determined by Multiplex analysis. The 'Millipore metabolic hormones Multiplex kit' (MMHMAG-44K) was used for analysis of C-peptide, GIP, insulin, leptin, pancreatic polypeptide, PYY and resistin. The beads were read on a LiquiChip 200, (Qiagen, Hombrechtikon, Switzerland), and data was analysed by the fiver parameter curve fitting in Luminex100 IS Software. Because too many leptin data points were out of range, leptin analysis was repeated ELISA (as described above).

To assess glomerular barrier function, urinary albumin (Exocell Inc. Philadelphia, Pa., USA) and creatinine concentrations were determined (Bethyl Laboratories Inc. Montgomery, Tex., USA) according to the instructions of the manufacturers.

In week 20, a glucose tolerance test was performed with n=8 mice per group, randomly selected. After 5 hours of fasting, mice were injected with 1 g/kg body weight of glucose (IP) and blood glucose and plasma insulin were measured at 0, 5, 15, 30, 60, and 120 min post injection.

Adipose Tissue Analysis

From all three adipose tissue depots (inguinal, omental and epididymal), cross-sections were prepared from paraffin-embedded samples and stained with hematoxylin-phloxine-saffron. From each mouse and each fat depot, three cross-sections were evaluated for the presence of crown-like structures. The analysed surface area of each cross-section was 580.000 $\mu m^2$, resulting in an analysed area of in total 1.74 $mm^2$.

Statistical Analysis

SPSS Version 20 was used for statistical evaluation of the data. Two-Way repeated measures ANOVA with factors time and diet were applied to analyse for a diet, time and interaction effect. One-Way ANOVA for individual time points were applied to analyse for differences at specific time points between groups. LDS post hoc test was used to compare groups. For non-parametric comparison, Mann-Whitney U tests were performed.

One mouse in the LFD and one mouse in the NHLL group were excluded from the data set and all analyses because they were statistical and biological outliers. $P<0.05$ was considered significant. All data are presented as mean±SEM.

General Health

Based on visual inspection and daily monitoring of mice, all mice behaved normally and appeared in good health. During the study one mouse in the HFD group was excluded due to overgrown incisors. The data of this particular mouse was not used for the analysis.

Body Weight and Food Intake Results

Twenty-one weeks of HFD feeing resulted in a body weight gain of approx. 25 g relative to the start (t=0), while LFD fed mice gained only approximately 10 g. The body weight of the HFD+PBS gavage control group was comparable to the HFD control. See FIG. 11A. Remarkably, the body weight of mice fed NHLL did not increase and remained as low as LFD fed mice.

Figures 11A, 11B:
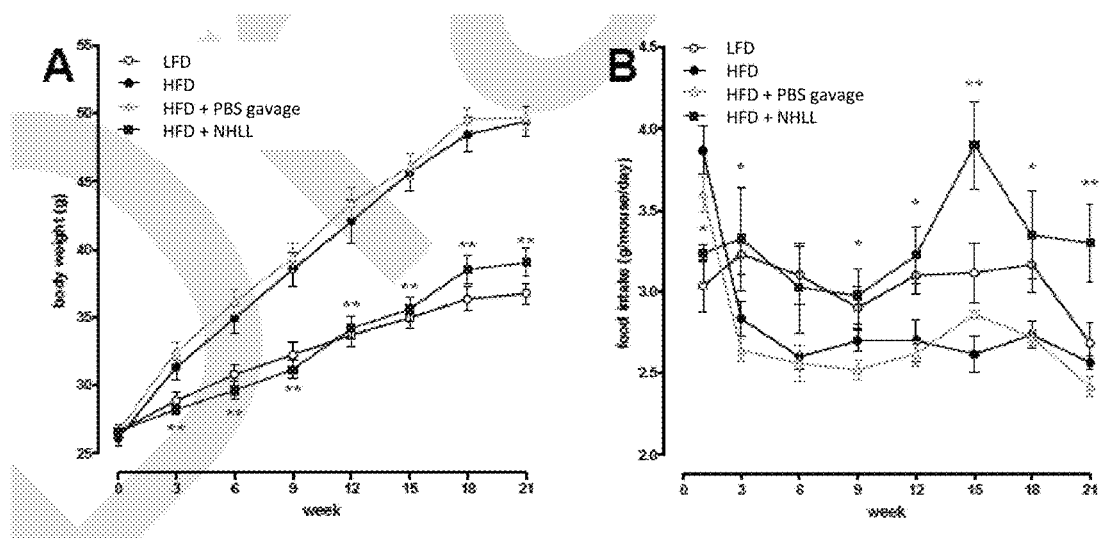
FIG. 11A illustrates body weight over 21 weeks for mice fed a HFD, mice fed a low fat diet ("LFD"), mice fed a HFD+PBS gavage, and mice fed a HFD supplemented with a peptide component, LGG, ARA and DHA (NHLL).
FIG. 11B illustrates food intake over 21 weeks for mice fed a HFD, mice fed a low fat diet ("LFD"), mice fed a HFD+PBS gavage, and mice fed a HFD supplemented with a peptide component, LGG, ARA and DHA (NHLL).

Both the HFD and HFD+PBS gavage control group showed a higher level of food intake in the first week. During the remainder of the experiment, food intake was relatively stable and comparable between the two control groups. The NHLL group did not show a peak in food intake in the first week. At all other time points food intake was elevated compared to the gavage control group (FIG. 11B). Statistical analysis of food intake across the whole study period revealed that food intake in NHLL was significantly increased compared to gavage control. Together these data show that animals treated with the nutritional formulation can maintain a low body weight (comparable to LFD treated mice), despite similar or increased consumption of food.

Blood Glucose and Plasma Insulin

Figure 12A:
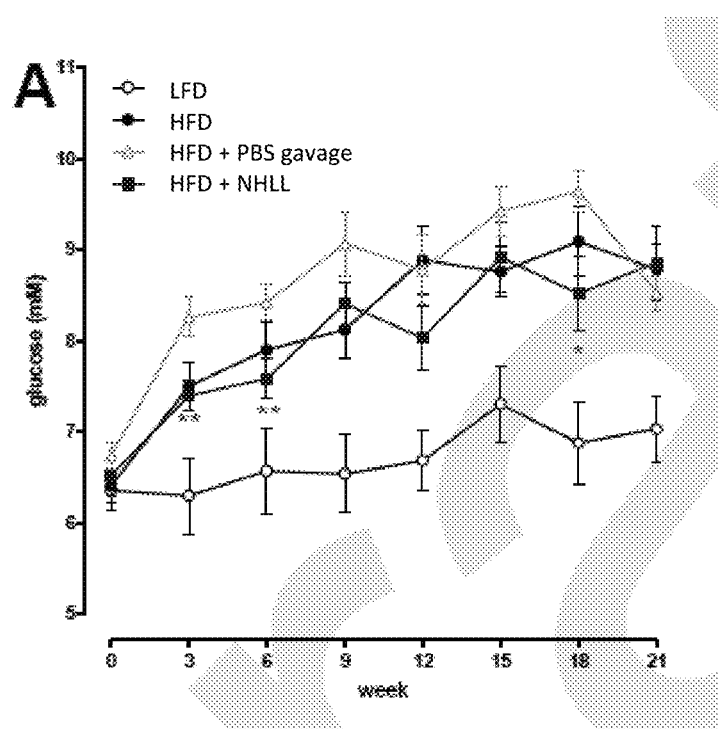
FIG. 12A illustrates fasting blood glucose over 21 weeks for mice fed a HFD, mice fed a low fat diet ("LFD"), mice fed a HFD+PBS gavage, and mice fed a HFD supplemented with a peptide component, LGG, ARA and DHA (NHLL).

HFD feeding resulted in an increase in fasting blood glucose relative to the starting level (6.5 mM on average), an effect which became already significant in week 3. By contrast fasting blood glucose in the LFD group remained low and stable over time. See FIG. 12A. The HFD+PBS gavage control group showed an increase in fasting blood glucose that was comparable to that of the HFD group. Blood glucose in the NHLL group also increased, although at several time points the levels were significantly lower than in the HFD+PBS gavage control group.

Figure 12B:
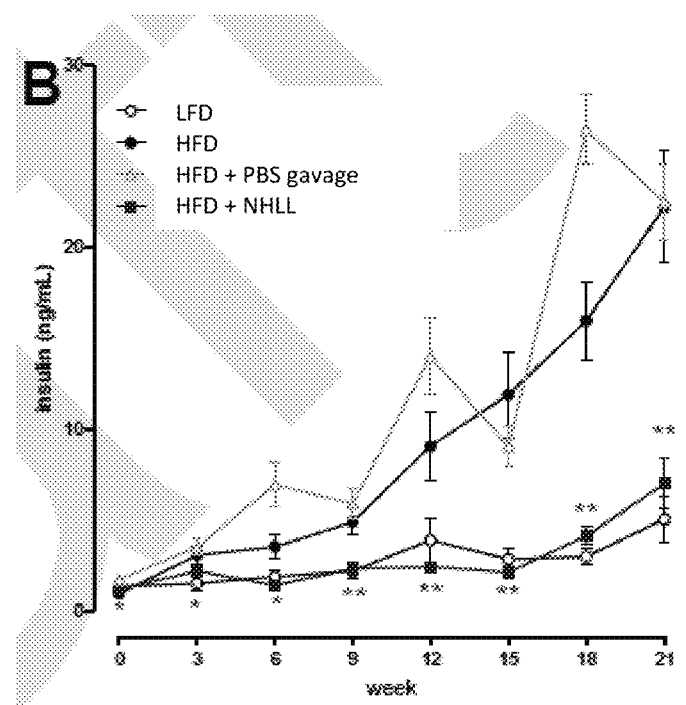
FIG. 12B illustrates fasting plasma insulin over 21 weeks for mice fed a HFD, mice fed a low fat diet ("LFD"), mice fed a HFD+PBS gavage, and mice fed a HFD supplemented with a peptide component, LGG, ARA and DHA (NHLL).

Plasma fasting insulin levels gradually increased over time in the HFD and HFD+PBS gavage control groups (FIG. 12B). The elevation in insulin was comparable between the groups and very pronounced in the second half of the experiment (Week 10 onwards). Insulin levels in the NHLL group remained at low (baseline) levels until week 15. There was a slight increase in week 18 and 21, but a similar increase was seen in the LFD group. The difference between NHLL and HFD+PBS gavage control was significant throughout the entire experiment.

Collectively, these data indicate that mice on HFD (see both control groups) tolerate a moderate increase in fasting glucose (period up to week 10). Thereafter fasting insulin levels increase strongly to keep glucose at the tolerated level. Mice treated with NHLL show low insulin levels throughout the study, indicating that increased insulin secretion is not necessary despite the fact that these animals consumed even more HFD than their controls. Hence, NHLL treated animals require little insulin to keep their glucose within the tolerated range.

Glucose Tolerance Test

Figures 13A, 13B:
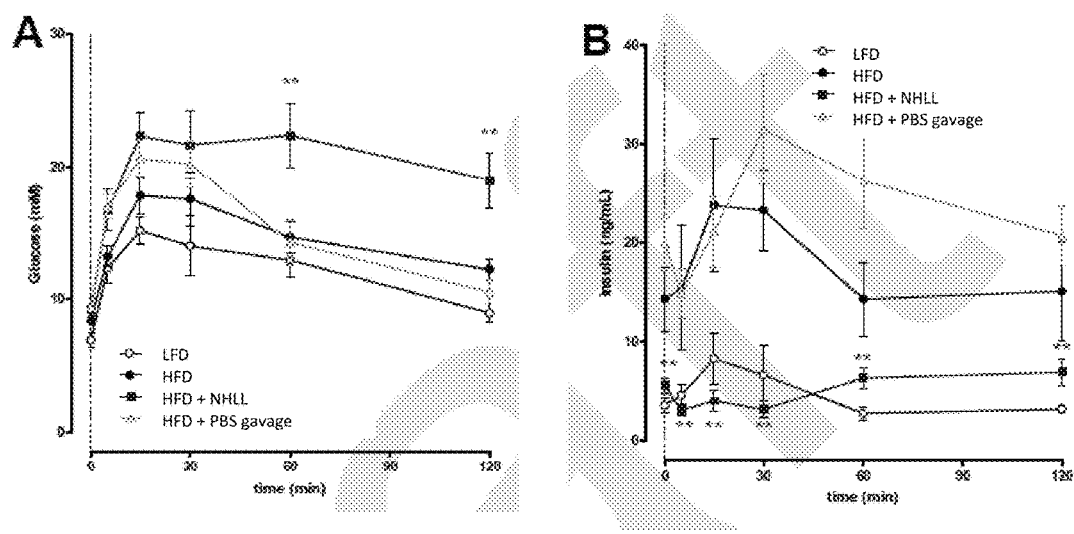
FIG. 13A illustrates blood glucose over 21 weeks for mice fed a HFD, mice fed a low fat diet ("LFD"), mice fed a HFD+PBS gavage, and mice fed a HFD supplemented with a peptide component, LGG, ARA and DHA (NHLL).
FIG. 13B illustrates plasma insulin over 21 weeks for mice fed a HFD, mice fed a low fat diet ("LFD"), mice fed a HFD+PBS gavage, and mice fed a HFD supplemented with a peptide component, LGG, ARA and DHA (NHLL).

At 20 weeks, a glucose tolerance test was performed in n=8 mice per group (n=7 for NHLL due to the exclusion of one outlier mouse from the entire data set). The oral glucose injection resulted in a rapid increase in blood glucose which reached a peak level between 15 and 30 min in all groups (FIG. 13A). The peak levels were lowest in the LFD group and higher in the HFD treated groups. The HFD control and HFD+PBS gavage control showed modest glucose clearance within the period studied (2 h) and the NHLL group had the slowest clearance of glucose suggesting differences in insulin during the glucose tolerance test.

Consistent with the previous measurements, insulin levels were low in the LFD and NHLL groups prior to glucose injection and relative to HFD and HFD+PBS gavage control groups. While HFD and HFD+PBS control groups showed a pronounced increase in insulin as a response to the oral glucose load, the NHLL group did not show such an insulin response. As for the LFD group (representing the most healthy control group), insulin levels remained low in NHLL and comparable to baseline levels throughout the 120 min sampling period. (FIG. 13B).

Thus, the two HFD control groups show a typical and pronounced insulin response during GTT with impaired clearance of glucose while LFD treated lack this insulin response and clear also slowly. Absence of an insulin response suggests that they tolerate a temporal increase in glucose. Similarly as the LFD group, NHLL treated animals do also not respond with an increase in insulin. Of note, these animals are fed HFD for 20 weeks and their metabolism is very likely fully adapted to utilize lipids as a source of energy. As a consequence of both (the lacking insulin response and their metabolic adaption), NHLL treated mice clear glucose very slowly. It is not clear why NHLL treated mice tolerate the high levels of glucose and why glucose is not cleared more rapidly. A possible explanation may be that NHLL treated mice have adapted their metabolism optimally to HFD allowing them to obtain sufficient energy for optimal functioning. Thus, tissues do not require energy (glucose) for fuel or storage.

Plasma Cholesterol and Triglycerides

Figures 14A, 14B:
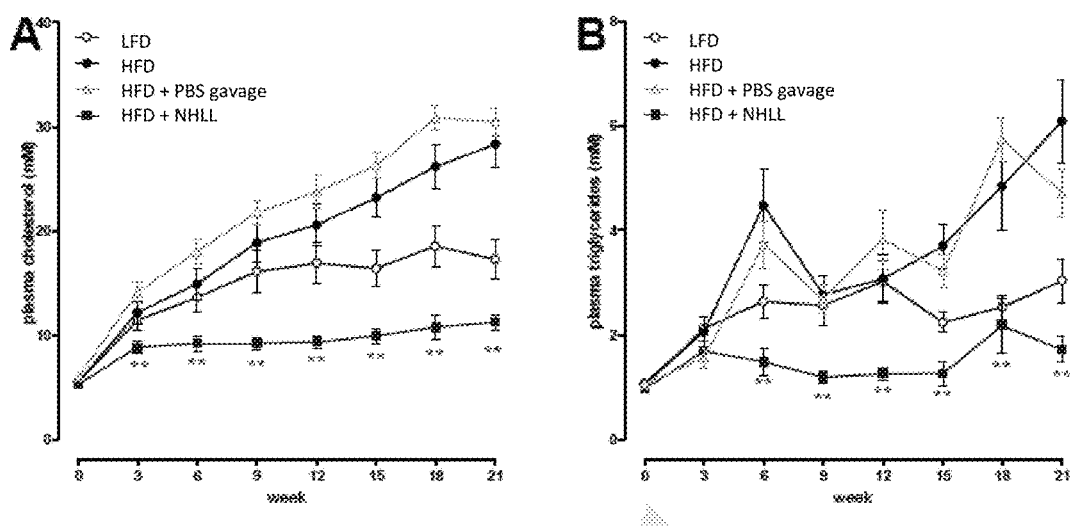
FIG. 14A illustrates fasting plasma cholesterol over 21 weeks for mice fed a HFD, mice fed a low fat diet ("LFD"), mice fed a HFD+PBS gavage, and mice fed a HFD supplemented with a peptide component, LGG, ARA and DHA (NHLL).
FIG. 14B illustrates fasting plasma triglycerides over 21 weeks for mice fed a HFD, mice fed a low fat diet ("LFD"), mice fed a HFD+PBS gavage, and mice fed a HFD supplemented with a peptide component, LGG, ARA and DHA (NHLL).

Plasma cholesterol increased gradually over time in the HFD and HFD+PBS gavage control group (FIG. 14A). Plasma cholesterol in the LFD group increased until approximately week 9 and remained stable for the remainder of the study. The NHLL group showed remarkably lower levels of plasma cholesterol compared to all other groups. Statistical evaluation showed that the cholesterol levels of the NHLL group were even lower than those of the LFD control group.

Plasma triglycerides also gradually increased over time in the HFD control group (FIG. 14B). At t=6 weeks, a transient peak was observed. Plasma triglycerides in the HFD+PBS gavage control group were grosso modo comparable to HFD and did not differ significantly (factor group in Two-Way ANOVA). Importantly, plasma triglycerides remained low in the NHLL group throughout the study.

Together, the NHLL treated mice showed very low total cholesterol and plasma triglyceride levels despite relatively high HFD consumption suggesting that either intestinal food uptake is reduced or more energy (lipids) is absorbed by the metabolically active organs and utilized.

Systemic and Vascular Inflammation

Figures 15A, 15B:
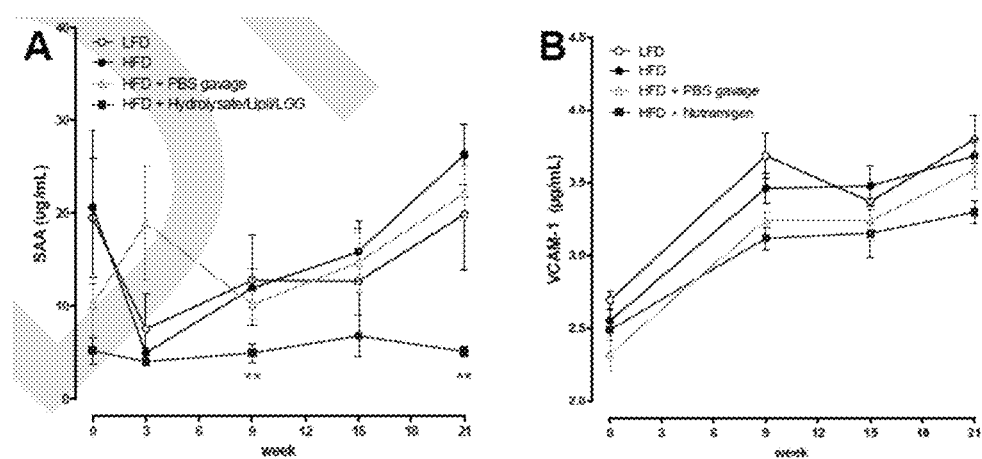
FIG. 15A illustrates fasting plasma serum amyloid A over 21 weeks for mice fed a HFD, mice fed a low fat diet ("LFD"), mice fed a HFD+PBS gavage, and mice fed a HFD supplemented with a peptide component, LGG, ARA and DHA (NHLL).
FIG. 15B illustrates fasting plasma VCAM-1 over 21 weeks for mice fed a HFD, mice fed a low fat diet ("LFD"), mice fed a HFD+PBS gavage, and mice fed a HFD supplemented with a peptide component, LGG, ARA and DHA (NHLL).

The systemic inflammation marker SAA showed large variation at baseline (FIG. 15A). Despite the large variations observed, the NHLL group showed consistently low SAA levels, while all control groups had higher SAA levels at most of the time points analysed. At mid-time (at=9 weeks) and at the end of the study (t=21 weeks), SAA levels were significantly lower in the NHLL group compared to HFD+PBS gavage control indicating that NHLL prevented the development of HFD-induced chronic inflammation ("low-grade metabolic inflammation").

VCAM-1 levels, a marker for vascular activation, were increased over time in all groups and independent of the dietary regimen. (FIG. 15B). Two Way ANOVA indicated that NHLL was not significantly different compared to the HFD+PBS gavage control. The increase in VCAM-1 over time may be related to the switch from a chow-based maintenance diet (on which the animals were kept from birth) to the experimental fat-containing diets.

Multiplex Analysis at End Point

Plasma samples after 21 weeks of experimental diet feeding were analyzed by multiplex technology to quantify humeral factors and cytokines. Multiplex data are shown below in Table 8. Overall, HFD feeding per se resulted in an increase of C-peptide, GIP, resistin and leptin relative to LFD while IL-6 was decreased and MCP-1, PP, PYY, TNF-α were hardly modulated.

TABLE 8

Multiplex analysis of circulating hormones/cytokines related to diabetes.

| Hormone/Cytokine | LFD | HFD | NHLL | Gavage Control |
|---|---|---|---|---|
| C-Peptide (ng/mL) | 6.7 ± 1.6 | 18.9 ± 3.6 | 10.1 ± 2.0** | 38.2 ± 5.2 |
| GIP (pg/mL) | 151 ± 35 | 200 ± 11 | 142 ± 11** | 194 ± 18 |
| IL-g(pg/mL) | 179 ± 52 | 63 ± 12 | 140 ± 51 | 71 ± 16 |
| MCP-1 (pg/mL) | 196 ± 64 | 140 ± 25 | 511 ± 183 | 144 ± 50 |
| PP (pg/mL) | 85 ± 31 | 135 ± 46 | 131 ± 33 | 90 ± 26 |
| PYY (pg/mL) | 153 ± 24 | 168 ± 26 | 173 ± 23 | 156 ± 15 |
| Resistin (ng/mL) | 9.7 ± 1.1 | 21.9 ± 2.8 | 20.1 ± 1.6 | 22.9 ± 1.8 |
| TNF-α (pg/mL) | 42 ± 15 | 34 ± 6 | 139 ± 46 | 49 ± 23 |
| Leptin (ng/mL)# | 12.6 ± 2.0 | 45.4 ± 3.0 | 20.6 ± 2.5** | 52.5 ± 2.7 |
| Adiponectin (μg/mL)# | 6.9 ± 2.6 | 4.4 ± 1.0 | 5.3 ± 1.3$ | 4.4 ± 1.0 |

Per Table 8:

GIP: Glucose-dependent Insulinotropic Polypeptide; MCP-1: Monocyte Chemotactic Protein-1; PP-Pancreatic Polypeptide; PYY: Peptide YY; TNF-α: Tumor Necrosis Factor alpha. LFD: Low Fat Diet; HFD: High Fat Diet; NHLL: Peptide Component, ARA, DHA, and LGG. * $P<0.05$; ** $P<0.01$ compared to gavage control. $ $P=0.07$ compared to gavage control; # Leptin data analysed by ELISA are presented because Leptin levels measured by multiplex were out of range.

C-peptide, GIP and leptin were significantly lower in the NHLL group compared to HFD+PBS gavage control. Adiponectin levels were borderline significantly elevated compared to HFD+PBS gavage control. The effect on C-peptide (which is co-secreted with insulin but more stable) is in line with the effects of NHLL on insulin. The reduced levels of leptin and higher levels of adiponectin seen in the NHLL group are in line with the low body weight and suggest an effect on adiposity and insulin sensitivity. MCP-1 and TNF-α tended to be higher in the NHLL group compared to gavage control (not significant). The other hormones and cytokines were not significantly different.

The observed differences between HFD and HFD+PBS gavage control for a few parameters (C-peptide, PP) may be due to the repeated gavage injections.

Albuminurea and ALAT

Figure 16A:
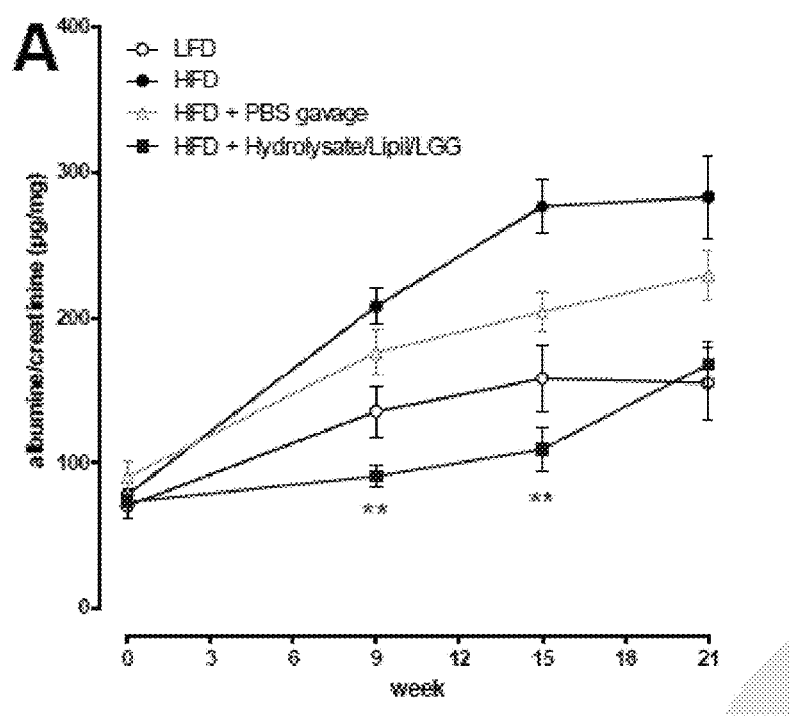
FIG. 16A illustrates albuminurea over 21 weeks for mice fed a HFD, mice fed a low fat diet ("LFD"), mice fed a HFD+PBS gavage, and mice fed a HFD supplemented with a peptide component, LGG, ARA and DHA (NHLL).
Figure 16B:
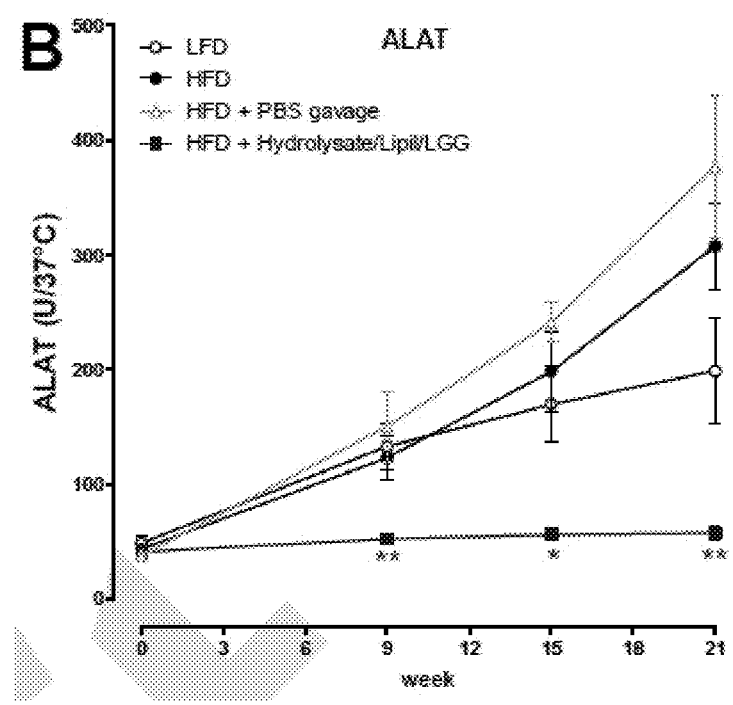
FIG. 16B illustrates circulating ALAT over 21 weeks for mice fed a HFD, mice fed a low fat diet ("LFD"), mice fed a HFD+PBS gavage, and mice fed a HFD supplemented with a peptide component, LGG, ARA and DHA (NHLL).

To assess effects on kidney function, albumin excretion in urine was analysed. See FIG. 16A. Albuminurea increased rapidly and markedly over time in the HFD and HFD+PBS gavage control groups. By contrast, albuminurea remained low until week 15 in the NHLL group and then increased somewhat in week 21. Until week 15 the levels were significantly lower in the NHLL group compared to HFD+PBS gavage control indicating that development of albuminuria was retarded by NHLL. To assess liver function, circulating ALAT levels were analyzed next (FIG. 16B). While all control groups showed a substantial increase in ALAT levels over time indicating liver damage, the ALAT levels of the NHLL group remained low and comparable to the LFD control group throughout the study. ALAT levels of NHLL group were significantly lower when compared to HFD+PBS gavage control at all time points analyzed.

Figure 16C:
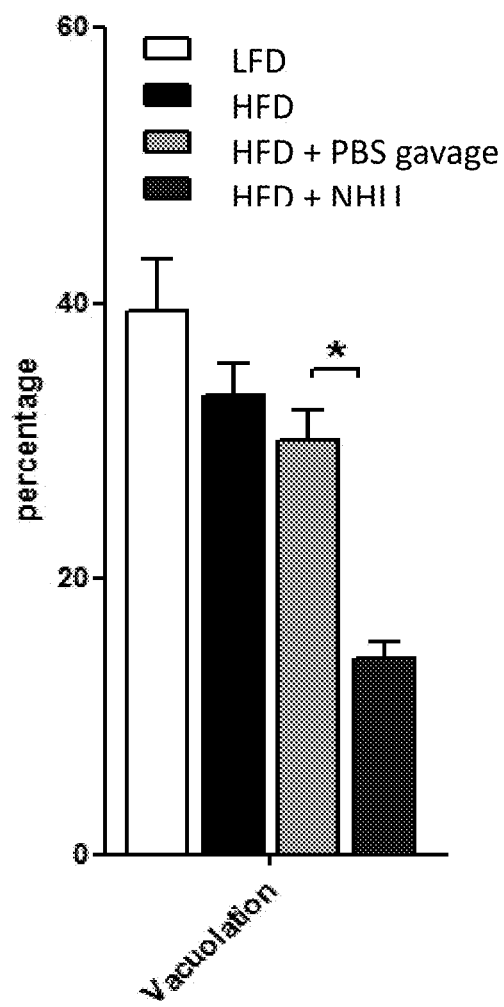
FIG. 16C illustrates vacuolation in the liver for mice fed a low fat diet (LFD), mice fed a HFD, mice fed a HFD+PBS gavage, and mice fed a HFD and supplemented with a peptide component, LGG, ARA, and DHA (NHLL).

In addition, NHLL markedly reduced vacuolation in the liver compared to HFD fed mice, a characteristic for liver steatosis (See FIG. 16C)

Body Composition Analysis and Tissue Weights at Sacrifice

Figure 17:
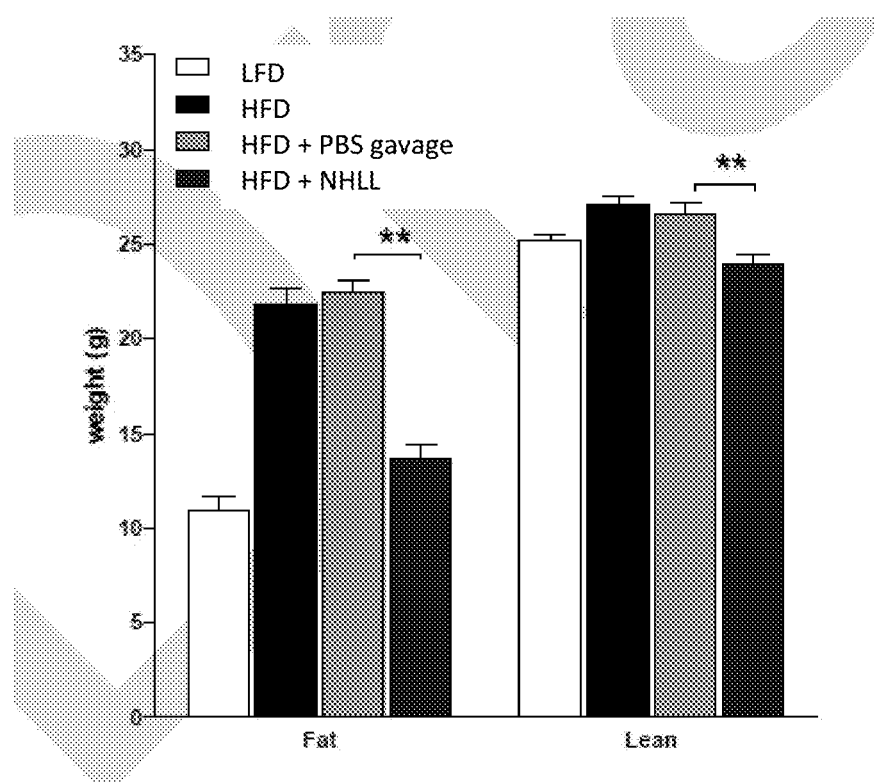
FIG. 17 illustrates total body fat and lean body mass at 21 weeks for mice fed a HFD, mice fed a low fat diet ("LFD"), mice fed a HFD+PBS gavage, and mice fed a HFD supplemented with a peptide component, LGG, ARA and DHA (NHLL).

Total body composition at 21 weeks was analysed non-invasively using the EchoMRI (See. FIG. 17). The differences in body weight can mainly be explained by differences in total body fat. The mice in the NHLL group had 39% less body fat compared to HFD+PBS gavage control and 10% less lean body mass. These data are in line with the effects on plasma leptin.

Figure 18:
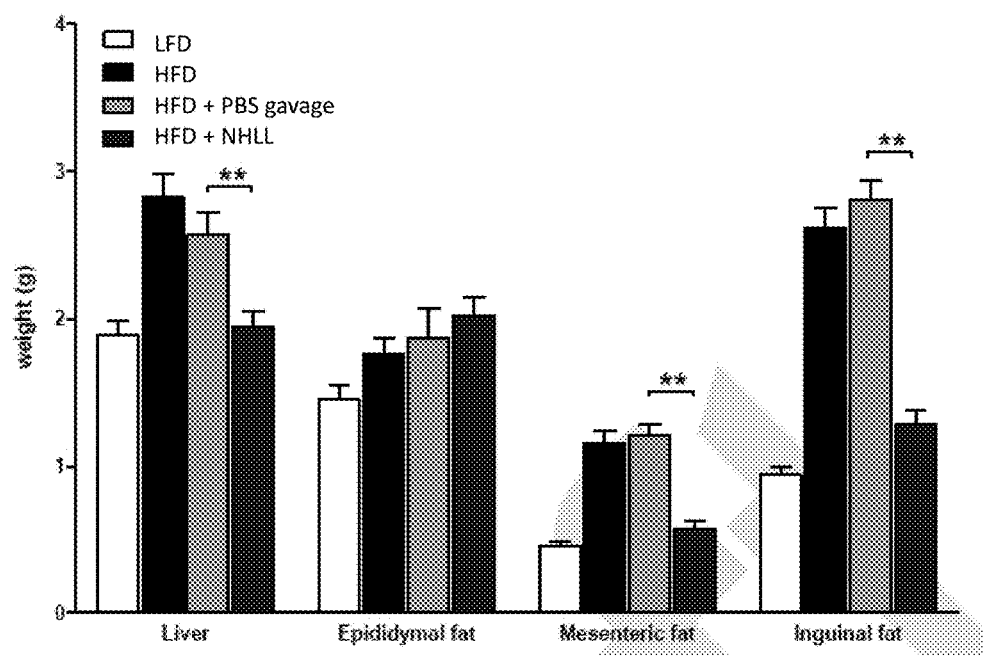
FIG. 18 illustrates tissue weights at sacrifice (t=21 weeks) from the liver, epididymal fat, mesenteric fat and inguinal fat after 21 weeks for mice fed a HFD, mice fed a low fat diet ("LFD"), mice fed a HFD+PBS gavage, and mice fed a HFD supplemented with a peptide component, LGG, ARA and DHA (NHLL).

After 21 weeks of dietary treatment, the mice were sacrificed. Tissues were isolated and weighed (FIG. 18). Liver weight of the two HFD control groups was markedly increased compared to LFD. The weight of livers of animals in the NHLL group was significantly reduced compared to HFD+PBS gavage control animals and LFD control animals.

Three adipose tissue depots were weighed. The epididymal fat depot was comparable between the NHLL and HFD+PBS gavage control group. On the other hand, the mesenteric and inguinal fat depot were strongly reduced compared HFD+PBS gavage control (−52% and −54% respectively) and comparable to LFD.

Adipose Tissue Inflammation

Figure 19A:
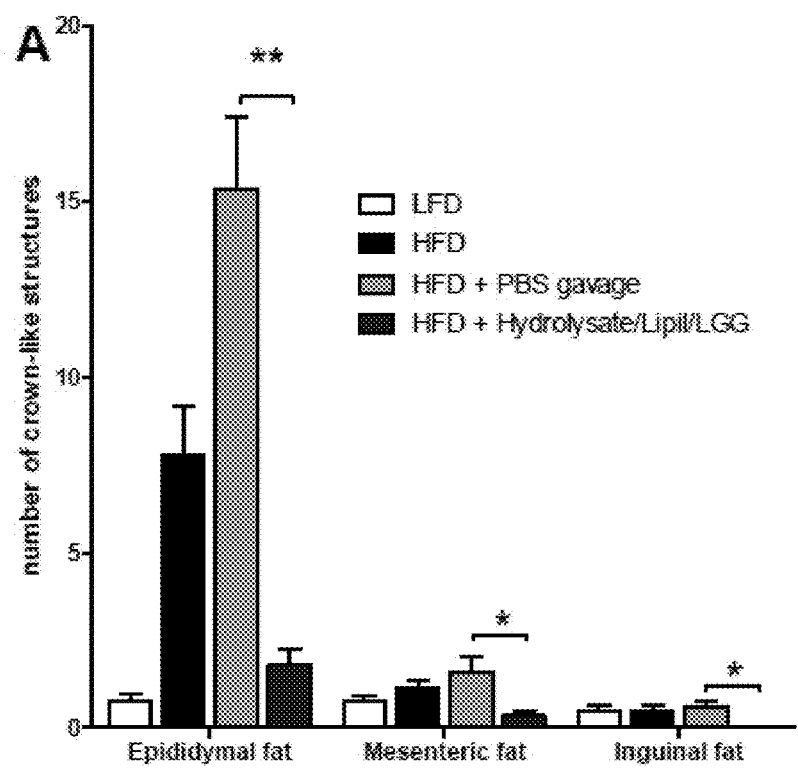
FIG. 19A illustrates the number of crown-like structures in epididymal fat, mesenteric fat, and inguinal fat at 21 weeks for mice fed a HFD, mice fed a low fat diet ("LFD"), mice fed a HFD+PBS gavage, and mice fed a HFD supplemented with a peptide component, LGG, ARA and DHA (NHLL).

Because NHLL had significant effects on obesity and adiposity and adipose tissue-derived factors associated with CVD and IR/T2D, the condition of the adipose tissue was evaluated. To assess inflammatory state of adipose tissue, we quantified the appearance of crown-like structure in an area of defined size. (FIG. 19A). Crown like structures are clusters of macrophages surrounding dying adipocytes or remnants thereof and represent a hallmark of the inflamed adipose tissue.

Figure 19B:
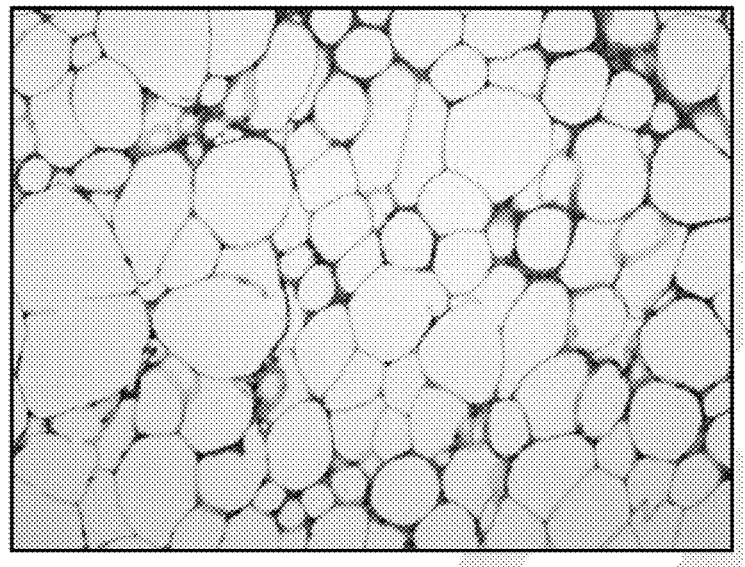
FIG. 19B displays a representative photomicrograph of a cross section of epididymal fat with crown like structures from a HFD+PBS gavage control mouse.
Figure 19C:
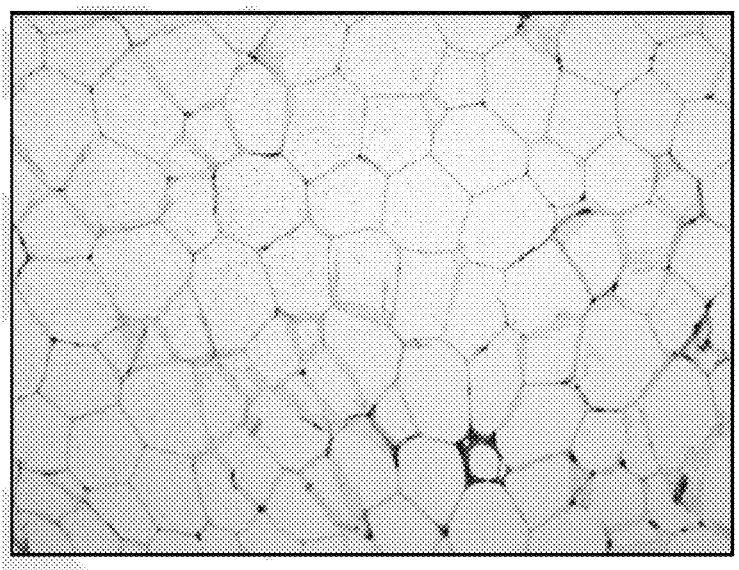
FIG. 19C displays a representative photomicrograph of a cross section of epididymal fat from a NHLL mouse fed a HFD supplemented with a peptide component, LGG, ARA and DHA (NHLL).

The HFD and HFD+PBS gavage control groups developed a considerable number of crown-like structures in the epididymal adipose tissue, while NHLL-treated mice showed hardly any crown-like structures in this depot. In the other adipose tissue depots (mesenteric and inguinal) which are less susceptible to develop inflammation only few crown-like structures were observed in the HFD and HFD+PBS gavage control groups. Also in these depots, a significant reduction of crown like structures was observed in the NHLL group compared to the HFD+PBS gavage control. Representative photomicrographs are shown in FIGS. 19B and 19C.

As such, body adiposity was strongly reduced in the NHLL mice, despite an increased intake of food. This may indicate an effect on energy uptake in the gut and/or energy expenditure. Lower circulating plasma lipids, inflammatory factors and reduced adipose tissue inflammation as well as retarded microalbuminuria in the NHLL mice indicate a reduced risk for development of cardiometabolic disease and vascular complications.

Also notable, the results of Example 3 are similar to those evaluated in Examples 1 and 2, indicating the robustness of the nutritional supplement including a peptide component, LCPUFA and LGG for counteracting HFD-induced cardiometabolic risk factors.

Example 4

Example 4 describes the effect on LDLr−/− mice as specified in Example 3, and the effect on brain influence via investigation of gene expression levels of several genes related to brain inflammation, blood brain barrier, and brain function. The same experimental procedures and methodologies as employed in Example 3 were used in Example 4.

Brain tissue samples as harvested according to Example 3 were utilized in Example 4. The right hemisphere samples were used for RNA isolation, cDNA synthesis and qPCR. The results were corrected for house-keeping genes GAPDH and HPRT as shown below if Table 9.

TABLE 9

| qPCR | |
|---|---|
| Gene Name | Primer Order Number (Life Technologies |
| BDNF | Mm01334047 m1 |
| Hprt (housekeeping gene) | Mm00446968 m1 |
| Gapdh | 4308313 |

Figure 20:
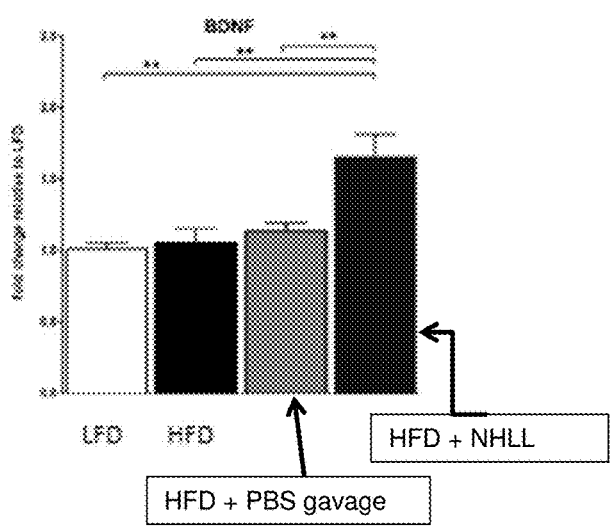
FIG. 20 illustrates qPCR data for one hemisphere of the brain in mice fed a low fat diet (LFD, mice fed a high fat diet (HFD), mice fed a HFD+gavage, and mice fed a HFD and supplemented with a peptide component, LGG, ARA, and DHA (NHLL).

Brain-Derived Neurotrophic Factor (BDNF) gene expression was markedly increased under NHLL supplementation in a HFD context. BDNF is a marker for neurogenesis. BDNF plays a role in survival of neurons, growth and differentiation of new neurons and synapses and is important for long term memory. (See FIG. 20)

Glucose transporter 1 (GLUT-1) immunohistochemistry was performed to elucidate vascular integrity via the number of GLUT-1 protein within blood vessel walls within the brain. Significant effects were found in the number of GLUT-1 positive blood vessel per µm2 and percentage of area covered. The intervention with NHLL decreased the amount of GLUT-1 positive blood vessels in the hippocampus, dentate gyrus (DG) and cornu ammonis area 1 (CA1). This effect suggests that this intervention is able to affect the cerebrovasculature, more specific decrease the amount of GLUT-1 positive blood vessels.

An inflammation process was indicated via an ionized calcium binding adapter molecule-1 antibody, IBA-1, which identifies activated microglia. IBA-1 immunohistochemistry was quantified in two ways, count of positive IBA-1 microglia per µm2 and percentage of area covered by the positive IBA-1 microglia. In both types of quantification significant intervention effects were revealed. The HFD-group revealed an increased number and percentage of IBA-1 positive microglia compared to a LFD, which indicates that a HFD induces an increased grade of inflammation which was to some extent counteracted by the NHLL supplementation.

Formulation Examples

Table 10 provides an example embodiment of a peptide component including 5 peptides from Table 1 and 3 peptides selected from Table 2 that may comprise the peptide component described herein

TABLE 10

Nutrition profile of an example peptide component
Example of Selected Peptides for Peptide Component

SEQ ID NO 5
SEQ ID NO 24
SEQ ID NO 33
SEQ ID NO 56
SEQ ID NO 64
SEQ ID NO 13

TABLE 10-continued

Nutrition profile of an example peptide component
Example of Selected Peptides for Peptide Component

SEQ ID NO 24
SEQ ID NO 60

Table 11 provides an example embodiment of a peptide component including 5 peptides from Table 1, 3 peptides selected from Table 2, and an additional 10 peptides from Table 1 that may comprise the peptide component described herein.

TABLE 11

Nutrition profile of an example peptide component
Example of Selected Peptides for Peptide Component SEQ ID NO 13
SEQ ID NO 24
SEQ ID NO 60
SEQ ID NO 5
SEQ ID NO 11
SEQ ID NO 22
SEQ ID NO 25
SEQ ID NO 33
SEQ ID NO 45
SEQ ID NO 46
SEQ ID NO 47
SEQ ID NO 48
SEQ ID NO 52
SEQ ID NO 34
SEQ ID NO 36
SEQ ID NO 61
SEQ ID NO 62
SEQ ID NO 64

Table 12 provides an example embodiment of a nutritional composition according to the present disclosure including a protein equivalent source and describes the amount of each ingredient to be included per 100 kcal serving.

TABLE 12

Nutrition profile of an example nutritional composition

| Nutrient | per 100 kcal | |
|---|---|---|
| | Minimum | Maximum |
| Protein Equivalent Source (g) | 1.0 | 7.0 |
| Carbohydrates (g) | 6 | 22 |
| Fat (g) | 1.3 | 7.2 |
| Prebiotic (g) | 0.3 | 1.2 |
| DHA (g) | 4 | 22 |
| Beta glucan (mg) | 2.9 | 17 |
| Probiotics (cfu) | 0.5 | 5.0 |
| Vitamin A (IU) | $9.60 \times 10^5$ | $3.80 \times 10^8$ |

TABLE 12-continued

Nutrition profile of an example nutritional composition

| Nutrient | per 100 kcal | |
|---|---|---|
| | Minimum | Maximum |
| Vitamin D (IU) | 134 | 921 |
| Vitamin E (IU) | 22 | 126 |
| Vitamin K (mcg) | 0.8 | 5.4 |
| Thiamin (mcg) | 2.9 | 18 |
| Riboflavin (mcg) | 63 | 328 |
| Vitamin B6 (mcg) | 68 | 420 |
| Vitamin B12 (mcg) | 52 | 397 |
| Niacin (mcg) | 0.2 | 0.9 |
| Folic acid (mcg) | 690 | 5881 |
| Panthothenic acid (mcg) | 8 | 66 |
| Biotin (mcg) | 232 | 1211 |
| Vitamin C (mg) | 1.4 | 5.5 |
| Choline (mg) | 4.9 | 24 |
| Calcium (mg) | 4.9 | 43 |
| Phosphorus (mg) | 68 | 297 |
| Magnesium (mg) | 54 | 210 |
| Sodium (mg) | 4.9 | 34 |
| Potassium (mg) | 24 | 88 |
| Chloride (mg) | 82 | 346 |
| Iodine (mcg) | 53 | 237 |
| Iron (mg) | 8.9 | 79 |
| Zinc (mg) | 0.7 | 2.8 |
| Manganese (mcg) | 0.7 | 2.4 |
| Copper (mcg) | 7.2 | 41 |

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. For example, while methods for the production of a commercially sterile liquid nutritional supplement made according to those methods have been exemplified, other uses are contemplated. Therefore, the spirit and scope of the appended claims should not be limited to the description of the versions contained therein.

What is claimed is:

1. A nutritional supplement comprising:
   (i) a source of long-chain polyunsaturated fatty acid;
   (ii) *Lactobacillus rhamnosus* GG; and
   (iii) a protein equivalent source comprising partially hydrolyzed proteins and intact proteins,
   wherein
   a) 20% to 80% of the protein equivalent source includes a peptide component, wherein the peptide component comprises each of the following individual peptides: SEQ ID NO: 4, SEQ ID NO: 13, SEQ ID NO: 17, SEQ ID NO: 21, SEQ ID NO: 24, SEQ ID NO: 30, SEQ ID NO: 31, SEQ ID NO: 32, SEQ ID NO: 51, SEQ ID NO: 57, SEQ ID NO: 60, and SEQ ID NO: 63; and
   b) 20% to 80% of the protein equivalent source comprises partially hydrolyzed proteins.

2. The nutritional supplement of claim 1, wherein the peptide component is present in an amount from about 0.2 g/100 kcals to about 5.6 g/100 kcals.

3. The nutritional supplement of claim 1, wherein the peptide component further comprises at least 10 additional peptides selected from Table 1.

4. The nutritional supplement of claim 1, wherein the protein equivalent source comprises partially hydrolyzed protein having a degree of hydrolysis of less than 40%.

5. The nutritional supplement of claim 1, further comprising at least one long-chain polyunsaturated fatty acid.

6. The nutritional supplement of claim 5, wherein the at least one long-chain polyunsaturated fatty acid is selected from the group consisting of docosahexaenoic acid and arachidonic acid.

7. The nutritional supplement of claim 1, further comprising a culture supernatant from a late-exponential growth phase of a probiotic batch-cultivation process, for use in the treatment or prevention of infection by a pathogen.

8. The nutritional supplement of claim 1, further comprising a probiotic.

9. The nutritional supplement of claim 1, further comprising a prebiotic.

10. The nutritional supplement of claim 1, wherein when administered to a subject, the nutritional supplement promotes a healthy weight, promotes a healthy body fat mass, lowers plasma cholesterol levels, lowers plasma triglycerides, or any combination thereof.

* * * * *

UNITED STATES PATENT AND TRADEMARK OFFICE
CERTIFICATE OF CORRECTION

PATENT NO.         : 10,251,928 B2
APPLICATION NO.    : 14/535241
DATED              : April 9, 2019
INVENTOR(S)        : Eric A. F. van Tol et al.

Page 1 of 1

It is certified that error appears in the above-identified patent and that said Letters Patent is hereby corrected as shown below:

On the Title Page

Add item (63), Related U.S. Application Data:
Continuation-in-Part of application No. 13/833,094, filed on Mar. 15, 2013, now Pat. No. 8,889,633;
Continuation-in-Part of application No. 13/833,039, filed on Mar. 15, 2013, now Pat. No. 9,345,741;
Continuation-in-Part of application No. 13/832,958, filed on Mar. 15, 2013, now Pat. No. 9,345,727;
Continuation-in-Part of application No. 14/513,584, filed on Oct. 14, 2014, now Pat. No. 9,457,058;

In the Specification

At Column 1, Lines 5-23, please delete the paragraph titled "Related Application" and replace with the below paragraph:
--CROSS-REFERENCE TO RELATED APPLICATIONS
This application claims the benefit of each of, and is a continuation-in-part of each of, U.S. Patent No. 8,889,633 (13/833,094), filed 15 March 2013; U.S. Patent No. 9,345,741 (13/833,039), filed 15 March 2013; U.S. Patent No. 9,345,727 (13/832,958), filed 15 March 2013; and U.S. Patent No. 9,457,058 (14/513,584), filed 14 October 2014, which is a Divisional of 8,889,633, the disclosures of each of which are incorporated by reference in their entirety.--

Signed and Sealed this
Twenty-fifth Day of February, 2020

Andrei Iancu
*Director of the United States Patent and Trademark Office*